United States Patent
Lindsley et al.

(10) Patent No.: US 11,851,428 B2
(45) Date of Patent: Dec. 26, 2023

(54) ACTIVATOR OF TREK (TWIK RELATED K⁺CHANNELS) CHANNELS

(71) Applicants: ONO PHARMACEUTICAL CO., LTD., Osaka (JP); VANDERBILT UNIVERSITY, Nashville, TN (US)

(72) Inventors: Craig W. Lindsley, Brentwood, TN (US); Joshua M. Wieting, Brentwood, TN (US); Kevin M. Mcgowan, Nashville, TN (US); Jerod S. Denton, Nashville, TN (US); Kentaro Yashiro, Osaka (JP); Haruto Kurata, Osaka (JP); Yoko Sekioka, Osaka (JP); Takahiro Mori, Osaka (JP); Yuzo Iwaki, Osaka (JP)

(73) Assignees: ONO PHARMACEUTICAL CO., LTD., Osaka (JP); VANDERBILT UNIVERSITY, Nashville, TN (US)

(*) Notice: Subject to any disclaimer, the term of this patent is extended or adjusted under 35 U.S.C. 154(b) by 191 days.

(21) Appl. No.: 17/328,814

(22) Filed: May 24, 2021

(65) Prior Publication Data

US 2021/0347773 A1    Nov. 11, 2021

Related U.S. Application Data

(62) Division of application No. 16/470,196, filed as application No. PCT/JP2017/044975 on Dec. 14, 2017, now Pat. No. 11,046,683.

(60) Provisional application No. 62/434,524, filed on Dec. 15, 2016.

(51) Int. Cl.
| | |
|---|---|
| C07D 213/36 | (2006.01) |
| C07D 231/12 | (2006.01) |
| C07D 249/08 | (2006.01) |
| C07D 401/04 | (2006.01) |
| A61K 31/454 | (2006.01) |
| C07D 471/04 | (2006.01) |
| C07C 255/57 | (2006.01) |
| C07C 317/28 | (2006.01) |
| C07D 209/30 | (2006.01) |
| C07D 213/89 | (2006.01) |
| C07D 231/56 | (2006.01) |
| C07D 235/16 | (2006.01) |
| C07D 237/24 | (2006.01) |
| C07D 239/47 | (2006.01) |
| C07D 249/18 | (2006.01) |
| C07D 257/04 | (2006.01) |
| C07D 265/36 | (2006.01) |
| C07D 271/10 | (2006.01) |
| C07D 285/14 | (2006.01) |
| C07D 295/04 | (2006.01) |
| C07D 513/04 | (2006.01) |

(52) U.S. Cl.
CPC .......... *C07D 471/04* (2013.01); *C07C 255/57* (2013.01); *C07C 317/28* (2013.01); *C07D 209/30* (2013.01); *C07D 213/89* (2013.01); *C07D 231/56* (2013.01); *C07D 235/16* (2013.01); *C07D 237/24* (2013.01); *C07D 239/47* (2013.01); *C07D 249/08* (2013.01); *C07D 249/18* (2013.01); *C07D 257/04* (2013.01); *C07D 265/36* (2013.01); *C07D 271/10* (2013.01); *C07D 285/14* (2013.01); *C07D 295/04* (2013.01); *C07D 401/04* (2013.01); *C07D 513/04* (2013.01)

(58) Field of Classification Search
CPC .. C07D 213/36; C07D 231/12; C07D 249/08; C07D 401/04; A61K 31/454
See application file for complete search history.

(56) References Cited

U.S. PATENT DOCUMENTS

| | | | |
|---|---|---|---|
| 7,879,893 B2 | 2/2011 | Olsen et al. | |
| 2004/0138286 A1 | 7/2004 | Imazaki et al. | |
| 2006/0160794 A1* | 7/2006 | Amegadzie | C07D 409/14 544/139 |
| 2008/0153802 A1 | 6/2008 | Lessene et al. | |

(Continued)

FOREIGN PATENT DOCUMENTS

| | | |
|---|---|---|
| JP | 2005-514413 A | 5/2005 |
| JP | 2009-525999 A | 7/2009 |

(Continued)

OTHER PUBLICATIONS

Registry(STN) [online], Aug. 30, 2007, date of search Dec. 5, 2021, CAS Registry No. 945892- 81-9, (1 page).

(Continued)

*Primary Examiner* — Bruck Kifle
(74) *Attorney, Agent, or Firm* — Foley & Lardner LLP

(57) ABSTRACT

Disclosed is a compound of formula (I):

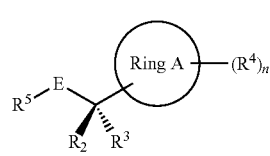

(I)

wherein all symbols are defined in the description. Also disclosed are pharmaceutical compositions comprising the compounds, methods of making the compounds, kits comprising the compounds, and methods of using the compounds, compositions and kits for treatment of disorders associated with TREK-1, TREK-2 or both TREK-1 and TREK-2 dysfunction in a mammal.

4 Claims, 1 Drawing Sheet

(56) References Cited

U.S. PATENT DOCUMENTS

| | | | |
|---|---|---|---|
| 2009/0099184 A1* | 4/2009 | Delombaert | C07D 213/81 546/261 |
| 2009/0181996 A1 | 7/2009 | Fuerstner et al. | |
| 2011/0263424 A1 | 10/2011 | Bretschneider et al. | |
| 2014/0178432 A1 | 6/2014 | Lischka et al. | |
| 2014/0243338 A1 | 8/2014 | Quan et al. | |
| 2015/0038466 A1 | 2/2015 | Ducki et al. | |
| 2015/0166496 A1 | 6/2015 | Roh et al. | |
| 2016/0009704 A1 | 1/2016 | Di Francesco et al. | |
| 2016/0159808 A1 | 6/2016 | Kawasaki et al. | |

FOREIGN PATENT DOCUMENTS

| | | |
|---|---|---|
| JP | 2010-522242 A | 7/2010 |
| JP | 2010-535161 A | 11/2010 |
| JP | 2013-028538 A | 2/2013 |
| JP | 2014-513968 A | 6/2014 |
| JP | 2014-527027 A | 10/2014 |
| WO | WO-99/65897 A1 | 12/1999 |
| WO | WO-00/69810 A1 | 11/2000 |
| WO | WO-01/00601 A1 | 1/2001 |
| WO | WO-02/46162 A1 | 6/2002 |
| WO | WO-02/100833 A1 | 12/2002 |
| WO | WO-03/032986 A1 | 4/2003 |
| WO | WO-03/057225 A2 | 7/2003 |
| WO | WO-2004/076412 A2 | 9/2004 |
| WO | WO-2004/081011 A1 | 9/2004 |
| WO | WO-2006/058905 A1 | 6/2006 |
| WO | WO-2006/066879 A2 | 6/2006 |
| WO | WO-2007/050348 A2 | 5/2007 |
| WO | WO-2007/098352 A2 | 8/2007 |
| WO | WO - 2007/130468 A2 | 11/2007 |
| WO | WO-2007/133637 A2 | 11/2007 |
| WO | WO-2007/138110 A2 | 12/2007 |
| WO | WO-2007/138112 A2 | 12/2007 |
| WO | WO-2008/050199 A2 | 5/2008 |
| WO | WO-2008/118758 A1 | 10/2008 |
| WO | WO-2009/017838 A2 | 2/2009 |
| WO | WO-2009/026254 A1 | 2/2009 |
| WO | WO-2009/036938 A1 | 3/2009 |
| WO | WO-2009/064449 A1 | 5/2009 |
| WO | WO 2009/117421 * | 9/2009 |
| WO | WO-2009/127678 A1 | 10/2009 |
| WO | WO-2009/145719 A1 | 12/2009 |
| WO | WO-2009/145721 A1 | 12/2009 |
| WO | WO-2009/147170 A2 | 12/2009 |
| WO | WO-2010/100606 A1 | 9/2010 |
| WO | WO-2010/102809 A1 | 9/2010 |
| WO | WO-2010/102811 A1 | 9/2010 |
| WO | WO-2011/021645 A1 | 2/2011 |
| WO | WO-2011/059048 A1 | 5/2011 |
| WO | WO-2012/053186 A1 | 4/2012 |
| WO | WO-2012/166951 A1 | 12/2012 |
| WO | WO-2013/156155 A1 | 10/2013 |
| WO | WO-2014/134388 A1 | 9/2014 |
| WO | WO-2015/012328 A1 | 1/2015 |
| WO | WO-2015/163472 A1 | 10/2015 |
| WO | WO-2015/186056 A1 | 12/2015 |

OTHER PUBLICATIONS

Shao, et al., "Discovery of a novel class of isoxazoline voltage gated sodium channel blockers", Bioorganic & Medicinal Chemistry Letters, vol. 19, No. 18, pp. 5329-5333, (2009).

Dadi, et al., "Selective Small Molecule Activators", ACS Chemical Neuroscience, Nov. 2, 2016, 8(3), 558-568.

Danthi, et al., "Caffeic Acid Esters", Molecular Pharmacology, 2004, vol. 65, No. 3, p. 599-610.

International Search Report for PCT/JP2017/044975 dated Jan. 23, 2018.

Lolicato, et al., "K2P2.1(TREK-1):activator complexes", Nature, 2017, vol. 547, p. 364-368.

Registry(STN) [online] RN 298684-44-3, Oct. 24, 2000, . . . , N-[(2,4-dichlorophenyl)methyl].

Prasanna K. Dadi et al: "Selective Small Molecule Activators of TREK-2 Channels Stimulate Dorsal Root Ganglion c-Fiber Nociceptor Two-Pore-Domain Potassium Channel Currents and Limit Calcium Influx", ACS Chemical Neuroscience, vol. 8, No. 3, Nov. 23, 2016 (Nov. 23, 2016), pp. 558-568.

* cited by examiner

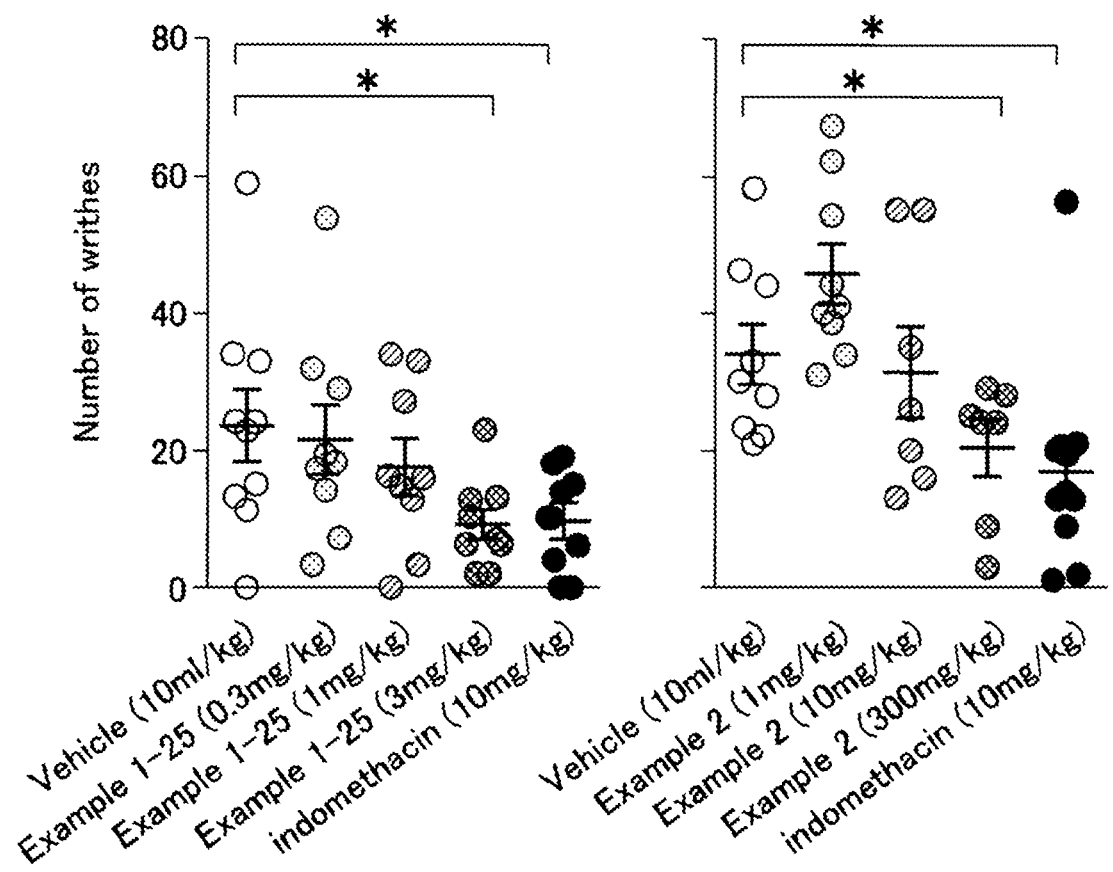

ACTIVATOR OF TREK (TWIK RELATED K⁺CHANNELS) CHANNELS

CROSS-REFERENCE TO RELATED APPLICATIONS

This application is a Divisional of U.S. patent application Ser. No. 16/470,196, filed on Jun. 14, 2019, which is a U.S. National Phase Application of International Patent Application No. PCT/JP2017/044975, filed Dec. 14, 2017, which claims the benefit of priority to U.S. Provisional Patent Application No. 62/434,524, filed Dec. 15, 2016, the disclosures of which are hereby incorporated herein by reference.

TECHNICAL FIELD

The present disclosure relates to compounds, compositions, and methods for treating disorders associated with $K_{2P}$ $K^+$ channels, specifically TREK (TWIK RElated $K^+$ channels) dysfunction for which activators of TREK-1, TREK-2 or both TREK-1 and TREK-2 would offer therapeutic benefit.

BACKGROUND

Potassium ($K^+$) channels are membrane proteins that are expressed in virtually every cell of the organism. $K^+$ channel subunits (~80 genes) can be divided into three main structural classes comprising shaker type voltage-gated (Kv), inward rectifier (Kir) and $K^+$ channels with two-pore domains ($K_{2P}$) (Kubo et al., Pharmacol Rev. 2005, 57, 509, Gutman, et al. Pharmacol Rev. 2005, 57, 473, Goldstein et al. Pharmacol Rev. 2005, 57, 527). The third family of $K^+$ channels was discovered 20 years ago (Leasge et al. EMBO J. 1996, 15, 1004). The 15 human $K_{2P}$ $K^+$ channels have been identified so far and classified into 6 structural subgroups: TWIK, TREK (TWIK RElated $K^+$ channels). TASK (TWIK related Acid-Sensitive $K^+$ channels), TALK (TWIK related ALkaline pH-activated $K^+$ channels), THIK (Tandem pore domain Halothane Inhibited $K^+$ channels) and TRESK (TWIK RElated Spinal cord $K^+$ channel) (Enyedi et al. Physiol. Rev. 2010, 90, 559). $K_{2P}$ $K^+$ channels are responsible for background or 'leak' $K^+$ currents. These channels are regulated by various physical and chemical stimuli, including membrane stretch, temperature, acidosis, lipids and inhalational anaesthetics. Furthermore, channel activity is tightly controlled by membrane receptor stimulation and second messenger phosphorylation pathways. Several members of this novel family of $K^+$ channels are highly expressed in the central and peripheral nervous systems in which they are proposed to play an important physiological role (TRENDs in Neurosci. 2001 June; 24(6):339-46.)

TREK-1, TREK-2, which belong to TREK subgroup, are thermo- and mechano-gated $K^+$ channel that is activated by lysophospholipids and polyunsaturated fatty acids (PUFAs) including arachidonic acid. They are regulated by G-protein-coupled receptors through PKA and PKC phosphorylation (Channels (Austin). 2011 September-October; 5(5):402-9). TREK-1 gene is widely expressed in the CNS with limited distribution in the periphery. In the CNS, TREK-1 expression is highest in the striatal tissues, the caudate and the putamen, as well as in spinal cord, foetal brain, amygdala and thalamus. In the periphery, TREK-1 expression is observed in heart, stomach and small intestine. TREK-2 gene has a similar expression profile compared to TREK-1 with high expression in particularly caudate, putamen and foetal brain. However, in contrast to TREK-1, TREK-2 is also highly expressed in cerebellum and corpus callosum as well as in several peripheral tissues, particularly kidney (Mol. Brain Res. 2001, 86, 101).

TREK-1 and TREK-2 have been shown to be involved in somatosensory perception and nociception. Thus, developing activators of TREK-1, TREK-2 channels may lead to therapeutic treatment of pain by producing hyperpolarizing currents that control cell membrane polarity and neuronal excitability throughout the nervous system (Nat Commun. 2013, 4, 2941, J. Neurosci. 2014, 34, 1494).

TREK-1 is inhibited by the activation of group 1 metabotropic glutamate receptors, known to be involved in brain disorders, including ischemia, epilepsy, neurodegenerative disorders (EMBO J. 2004, 23, 2684). Thus, the activation of TREK-1 should protect the neuronal cell against excessive and deleterious neuronal excitability and $Ca^{2+}$ entry, which leads to the belief that TREK-1 activators may also be useful for the treatment of ischemia, epilepsy, neurodegenerative disorders.

TREK-1 channels are expressed in the heart and implicated in action potential regulation, which leads to the belief that TREK-1 activators may also be useful for the treatment of atrial fibrillation (Life Sci. 2014, 97, 107).

The suppression of TREK-1 channels have been shown to be contributed to the potentiating action of Arginine vasopressin (AVP) on corticotropin-releasing hormone (CRH) evoked adrenocorticotropic hormone (ACTH) secretion. Thus, an increase in the opening of the TREK-1 channel will oppose the stimulatory effect of CRH and AVP on the electrical excitability of corticotropes and will, in turn, reduce the stress-induced ACTH release, which leads to the belief that TREK-1 activators are also useful for the disease with abnormally high levels of cortisol, e.g., Cushing's syndrome (Endocrinology 2015, 156, 3661). TREK-1 activators are also useful for nasal inflammation (Sci Rep. 2015, 5, 9191), acute respiratory distress syndrome (acute lung injury) (Am. J. Physiol. Lung Cell Mol. Physiol. 2015, 308, L731), overactive bladder (J. Pharmacol. Exp. Ther. 2005, 313250), amyotrophic lateral sclerosis (Mol. Pharmacol. 2000, 57, 906), sepsis (J. Surg. Res. 2015,193, 816), pancreatic cancer (Biochim. Biophys. Acta. 2016, 1862, 1994).

TREK-2 channels are expressed in the kidney, proximal convoluted tubule epithelial cells, and that polycystins protect renal epithelial cells against apoptosis in response to mechanical stress, and this function is mediated through the opening of TREK-2 (Cell Rep. 2012, 1, 241). Thus, TREK-2 activators are useful for autosomal dominant polycystic kidney disease. TREK-2 channels are functionally upregulated in astrocytes after ischemia and rescue astrocytic buffering of glutamate, which leads to the belief that TREK-2 activators are also useful for ischemia (Open Neurosci J. 2009, 3, 40). The entorhinal cortex is closely associated with the consolidation and recall of memories, Alzheimer disease, schizophrenia, and temporal lobe epilepsy. Norepinephrine is a neurotransmitter that plays a significant role in these physiological functions and neurological diseases. Norepinephrine activates TREK-2 via alpha 2A adrenergic receptors-mediated inhibition of the protein kinase A pathway, which leads to hyperpolarizes membrane potential and depresses neuronal excitability (J. Biol Chem. 2009, 284, 10980, ACS Chem Neurosci. 2016 Sep. 22 (WEB ASAP)). Thus, TREK-2 activators are useful for Alzheimer disease, schizophrenia and temporal lobe epilepsy.

TREK-2 is involved in stretch-induced PTH-related protein gene expression in osteoblasts, which is suggested as a candidate endogenous mediator of the anabolic effects of mechanical force on bone (*J. Bone Miner Res.* 2005, 20, 1454). Thus, TREK-2 activators are also useful for bone fracture, osteoporosis.

Selective activation of TREK-1, by a small molecule activator, has potential therapeutic benefit for: pain, nasal inflammation, atrial fibrillation, acute respiratory distress syndrome, cerebreal ischemia, overactive bladder, epilepsy, amyotrophic lateral sclerosis, anaesthesia, neuronal degeneration diseases, sepsis, pancreatic cancer and Cushing's syndrome (*Nat. Commun.* 2013, 4, 2941, *Sci. Rep.* 2015, 5, 9191, *Life Sci.* 2014, 97, 107, *EMBO J.* 2004, 23, 2684, *Mol. Pharmacol.* 2000, 57, 906, *Biochim. Biophys. Acta.* 2016, 1862, 1994, *Endocrinology* 2015, 156, 3661).

Selective activation of TREK-2, by a small molecule activator, has potential therapeutic benefit for: pain, ischemia, autosomal dominant polycystic kidney disease, osteoporosis, anaesthesia, temporal lobe epilepsy and schizophrenia (*J. Neurosci.* 2014, 34, 1494, *Open Neurosci J.* 2009, 3, 40, *Cell Rep.* 2012, 1, 41, *J. Bone Miner. Res.* 2005, 20, 1454, *Neurosci. Lett.* 2016, 619, 54, *J. Biol. Chem.* 2009, 284, 10980, *ACS Chem Neurosci.* 2016 WEB ASAP).

All of the above mentioned disorders may also be effectively treated by a dual TREK-1/TREK-2 activator, with varying degrees of TREK-1 and TREK-2 preference.

Despite advances in $K_{2P}$ channel research and TREK-1/TREK-2 pharmacology channel research, there is still a scarcity of compounds that are potent, efficacious, and selective activators of the either TREK-1, TREK-2 or both TREK-1 and TREK-2 and also effective in the treatment of disorders associated with $K_{2P}$ $K^+$ channels, specifically TREK (TWIK RElated $K^+$ channels) dysfunction for which activators of TREK-1, TREK-2 or both TREK-1 and TREK-2 would offer therapeutic benefit.

For example, PTL 1 discloses that the compound represented by formula (A)

[Chem. 1]

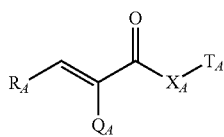

(A)

wherein $R_A$ represents;
a saturated, partially or totally unsaturated, aromatic or non-aromatic, substituted or non-substituted, 5-, 6- or 7-membered carbocycle;
a saturated, partially or totally unsaturated, aromatic or non-aromatic, substituted or non-substituted, 5-, 6- or 7-membered heterocycle; or the like;

$Q_A$ represents a $C_1$-$C_6$ alkyl group, —$NR_1R_2$ or the like;
$Q_A$, $R_A$ and the carbon atoms to which they are bounded, may form a saturated, partially or totally unsaturated, aromatic or non-aromatic, substituted or non-substituted, carbocycle, heterocycle, 9-, 10- or the like membered condensed carbocycle, or 9-, 10- or the like membered condensed heterocycle;

$X_A$ represents $NR^{1A}$ or the like;
$T_A$ represents;
a $C_1$-$C_6$ alkyl-aryl group;
a $C_1$-$C_6$ alkyl-heterocycle group; or the like;
$R^{1A}$ represents a hydrogen atom, or a $C_1$-$C_6$ alkyl group;

as well as an isomor or a pharmaceutically acceptable salt of this compound (the definitions of respective group are abstracted) is useful for treatment of pain.

NPL 1 discloses that the Cinnamyl 1-3,4-dihydroxy-α-cyanocinnamate compound represented by the following formula (B):

[Chem. 2]

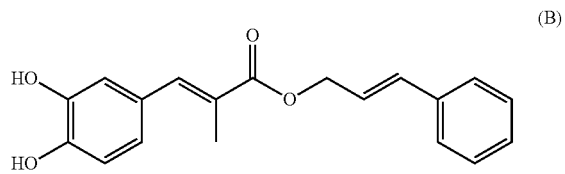

is a TREK-1 activator.

NPL 2 discloses that the N-aryl-sulfonamide compound represented by the following formula (C):

[Chem. 3]

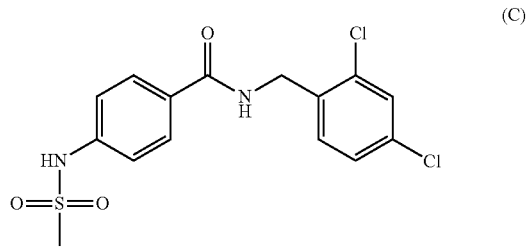

is a TREK-1 and TREK-2 activator.

CITATION LIST

Patent Literature

[PTL 1]
US 2015/0038466

Non Patent Literature

[NPL 1]
Molecular Pharmacology, 2004, Vol. 65, No. 3, p. 599-610
[NPL 2]
Nature, 2017, Vol. 547, p. 364-368

SUMMARY

In one aspect, disclosed is a compound of formula (I);

[Chem. 4]

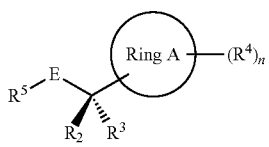

wherein; all symbols are defined as below.

Also disclosed are pharmaceutical compositions comprising the compounds, methods of making the compounds, kits comprising the compounds, and methods of using the compounds, compositions and kits for treatment of disorders associated with TREK-1, TREK-2 or both TREK-1 and TREK-2 dysfunction in a mammal.

BRIEF DESCRIPTION OF DRAWINGS

[The FIGURE]

The FIGURE; Shows that the compounds of Example 1-25 and Example 2 inhibit the number of writhes induced by acetic acid in the mouse. The vertical axis shows the number of writhes, and the horizontal axis shows the group to which vehicle, the test compounds or indomethacin was administered. (*$p<0.05$ compared to vehicle-treated group (Student's t-test)).

DETAILED DESCRIPTION

Disclosed herein are activators of the TREK (TWIK RElated K$^+$ channels)—subtypes 1 and/or 2 (TREK-1 and/or TREK-2) That is, the invention relates to;
1. A compound of formula (I):

[Chem. 5]

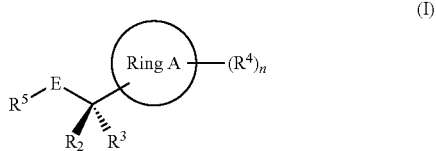

wherein
E is —C(O)NR$^1$—, or —NR$^1$C(O)—;
R$^1$ is hydrogen, or C$_1$-C$_4$-alkyl;
R$^2$ is hydrogen, or C$_1$-C$_4$-alkyl;
R$^3$ is hydrogen, or C$_1$-C$_4$-alkyl;
Ring A is aryl or heteroaryl;
R$^4$ is (1) halogen, (2) SF$_5$, (3) alkyl, (4) alkenyl, (5) alkynyl, (6) aryl, (7) heteroaryl, (8) cycloalkyl, (9) heterocycle, (10) —OR$^{11}$, (11) —SR$^{12}$, (12) —C(O)R$^{13}$, (13) —C(O)OR$^{14}$, (14) —S(O)R$^{15}$, (15) —SO$_2$R$^{16}$, (16) —NR$^{17}$R$^{18}$, (17) —C(O)NR$^{19}$R$^{20}$, (18) —NR$^{21}$C(O)R$^{22}$, (19) —S(O)$_2$NR$^{23}$R$^{24}$, (20) —(CR$^6$R$^7$)$_p$—W, or (21) —CN; each of which may be optionally substituted;
R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$ and R$^{24}$ are independently hydrogen, alkyl, alkenyl, alkynyl, aryl, arylalkyl, cycloalkyl, cycloalkylalkyl, heterocycle, heterocyclealkyl, heteroaryl, or heteroarylalkyl; each of which may be optionally substituted;
R$^6$ and R$^7$ are independently hydrogen, halogen, C$_1$-C$_4$-alkyl, C$_1$-C$_4$-haloalkyl, aryl, heteroaryl, cycloalkyl, or heterocycle;
W is hydrogen, halogen, —OR$^{31}$, —SR$^{32}$, —C(O)R$^{33}$, —C(O)OR$^{34}$, —S(O)R$^{35}$, —SO$_2$R$^{36}$, —NR$^{37}$R$^{38}$, —C(O)NR$^{39}$R$^{40}$, —NR$^{41}$C(O)R$^{42}$, —S(O)$_2$NR$^{43}$R$^{44}$, aryl, heteroaryl, cycloalkyl, or heterocycle; each of which may be optionally substituted;
R$^{31}$, R$^{32}$, R$^{33}$, R$^{34}$, R$^{35}$, R$^{36}$, R$^{37}$, R$^{38}$, R$^{39}$, R$^{40}$, R$^{41}$, R$^{42}$, R$^{43}$ and R$^{44}$ are independently hydrogen, alkyl, alkenyl, alkynyl, aryl, arylalkyl, cycloalkyl, cycloalkylalkyl, heterocycle, heterocyclealkyl, heteroaryl, or heteroarylalkyl; each of which may be optionally substituted;
p is 1, 2, 3, 4, or 5;
n is 0, 1, 2, 3, 4, or 5; wherein multiple R$^4$ may be the same as or different from each other when n is 2 or more;

R$^5$ is aryl, arylalkyl, heteroaryl, heteroarylalkyl, heterocycle, or heterocyclealkyl; each of which may be optionally substituted; or a pharmaceutically acceptable salt thereof.

2. The compound according to 1, wherein Ring A is benzene, pyridine, pyridazine, pyrimidine, or pyrazine; or a pharmaceutically acceptable salt thereof.

3. The compound according to 1 or 2, which is a compound of formula (Ia):

[Chem. 6]

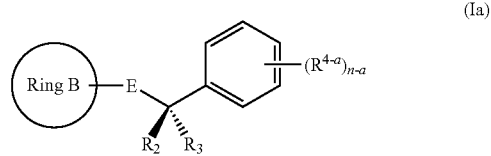

wherein
Ring B is benzene, naphthalene, or 5-10 membered heteroaryl;
Ring B may be optionally substituted with 1 to 3 R$^8$; wherein multiple R$^8$ may be the same as or different from each other;
R$^8$ is halogen, C$_1$-C$_4$-alkyl, C$_1$-C$_4$-haloalkyl, C$_1$-C$_4$-alkoxy, C$_1$-C$_4$-haloalkoxy, C$_1$-C$_4$-alkyl-SO$_2$—, C$_1$-C$_4$-alkyl-SO$_2$NH—, amino, or cycloalkyl;
R$^{4-a}$ is halo, SF$_5$, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio, or C$_1$-C$_4$-haloalkylthio;
n-a is 1, 2, 3, or 4; wherein multiple R$^{4-a}$ may be the same as or different from each other when n-a is 2 or more;
the other symbols are as defined in 1; or
a pharmaceutically acceptable salt thereof.

4. The compound according to any one of the 1 to 3, which is a compound of formula (Ic):

[Chem. 7]

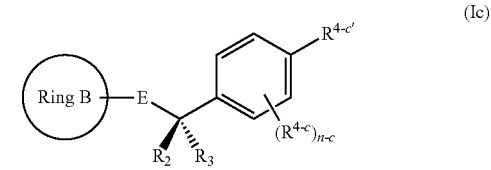

wherein
R$^{4-c}$ and R$^{4-c'}$ are independently halo, SF$_5$, C$_1$-C$_4$-alkyl, C$_1$-C$_4$-haloalkyl, C$_1$-C$_4$-alkoxy, C$_1$-C$_4$-haloalkoxy, C$_1$-C$_4$ alkylthio, or C$_1$-C$_4$ haloalkylthio;
multiple R$^{4-c}$ may be the same as or different from each other when n-c is 2 or more;
n-c is 0, 1, 2, or 3;
the other symbols are as defined in 1 or 3; or
a pharmaceutically acceptable salt thereof.

5. The compound according to any one of the 1 to 4, which is a compound of formula (Ic-1):

[Chem. 8]

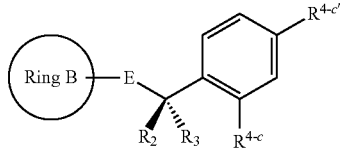

(Ic-1)

all symbols are as defined in any one of the 1, 3 or 4; or a pharmaceutically acceptable salt thereof.

6. The compound according to the 1 or 2, which is a compound of formula (If):

[Chem. 9]

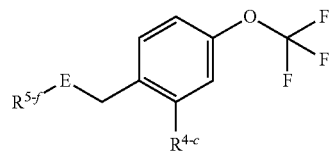

(If)

wherein $R^{5-f}$ is Ring B, Ring B may be optionally substituted with 1 to 3 $R^8$, or

[Chem. 10]

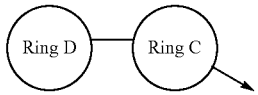

arrow represents connecting position with E;

Ring C is benzene or 5-6 membered heteroaryl, which may be optionally substituted with 1 to 3 $R^9$; wherein multiple $R^9$ may be the same as or different from each other;

$R^9$ is halogen, hydroxyl, $C_1$-$C_4$-alkyl, $C_1$-$C_4$-haloalkyl, $C_1$-$C_4$-alkoxy, or $C_1$-$C_4$-haloalkoxy;

Ring D represents benzene, 5-6 membered heterocycle or 5-6 membered heteroaryl, which may be optionally substituted with 1 to 3 $R^{10}$; wherein multiple $R^{10}$ may be the same as or different from each other;

$R^{10}$ is halogen, hydroxyl, oxo, $C_1$-$C_4$-alkyl, $C_1$-$C_4$-haloalkyl, $C_1$-$C_4$-alkoxy, or $C_1$-$C_4$-haloalkoxy;

the other symbols are as defined in 1, 3 or 4; or a pharmaceutically acceptable salt thereof.

7. The compound according to any one of the 1 to 6, which is a compound of formula (Ic-1-1):

[Chem. 11]

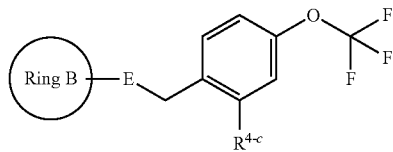

(Ic-1-1)

all symbols are as defined in any one of the 1, 3 or 4; or a pharmaceutically acceptable salt thereof.

8. The compound according to any one of the 1 to 7, wherein Ring B is

[Chem. 12]

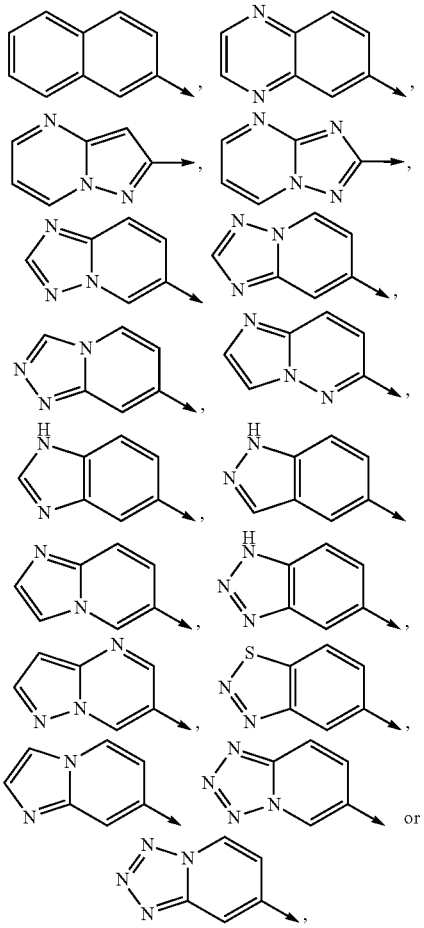

wherein arrow represents connecting position with E, each of which may be optionally substituted with 1 to 3 $R^8$; or a pharmaceutically acceptable salt thereof.

9. The compound according to any one of the 1 to 8, wherein;

Ring B is

[Chem. 13]

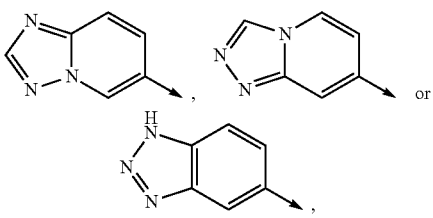

wherein arrow represents connecting position with E, each of which may be optionally substituted with 1 to 3 $R^8$; or a pharmaceutically acceptable salt thereof.

10. The compound according to 1 or 2, which is a compound of formula (Ib):

[Chem. 14]

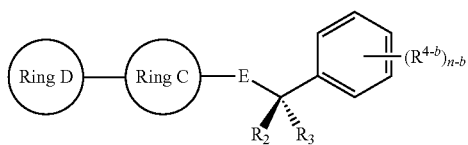

(Ib)

wherein
R$^{4-b}$ is halo, SF$_5$, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio, or C$_1$-C$_4$-haloalkylthio;
n-b is 1, 2, 3 or 4; wherein multiple R$^{4-b}$ may be the same as or different each other when n-b is 2 or more;
Ring C is benzene or 5-6 membered heteroaryl, which may be optionally substituted with 1 to 3 R$^9$; wherein multiple R$^9$ may be the same as or different from each other;
R$^9$ is halogen, hydroxyl, C$_1$-C$_4$-alkyl, C$_1$-C$_4$-haloalkyl, C$_1$-C$_4$-alkoxy, or C$_1$-C$_4$-haloalkoxy;
Ring D represents benzene, 5-6 membered heterocycle or 5-6 membered heteroaryl, which may be optionally substituted with 1 to 3 R$^{10}$; wherein multiple R$^{10}$ may be the same as or different from each other;
R$^{10}$ is halogen, hydroxyl, oxo, C$_1$-C$_4$-alkyl, C$_1$-C$_4$-haloalkyl, C$_1$-C$_4$-alkoxy, or C$_1$-C$_4$-haloalkoxy;
the other symbols are as defined in 1; or
a pharmaceutically acceptable salt thereof.

11. The compound according to any one of the 1, 2 and 10, which is a compound of formula (Id):

[Chem. 15]

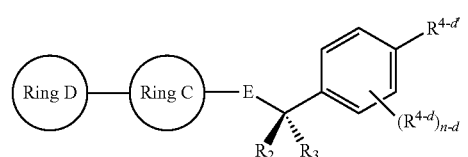

(Id)

wherein R$^{4-d}$ and R$^{4-d'}$ are independently halo, SF$_5$, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio, or C$_1$-C$_4$-haloalkylthio;
multiple R$^{4-d}$ may be the same as or different from each other when n-d is 2 or 3;
n-d is 0, 1, 2 or 3;
the other symbols are as defined in the 1 or 10; or
a pharmaceutically acceptable salt thereof.

12. The compound according to any one of the 1, 2, 10 and 11, which is a compound of formula (Id-1):

[Chem. 16]

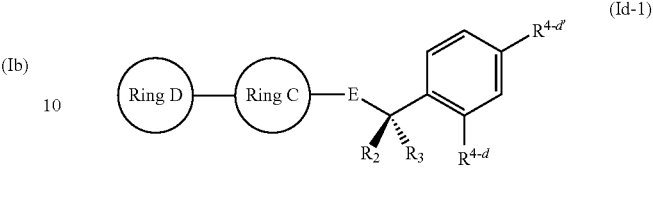

(Id-1)

all symbols are as defined in any one of the 1, 10 or 11; or
a pharmaceutically acceptable salt thereof.

13. The compound according to any one of the 1, 2, 6 and 10 to 12, which is a compound of formula (Id-1-1):

[Chem. 17]

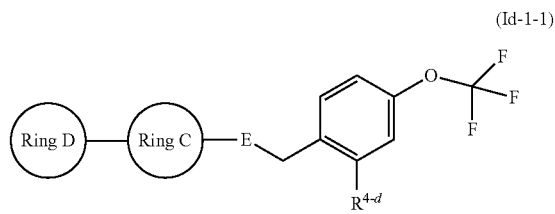

(Id-1-1)

all symbols are as defined in any one of the 1, 10 or 11; or
a pharmaceutically acceptable salt thereof.

14. The compound according to any one of the 1, 2, 6 and 10 to 13, wherein

[Chem. 18]

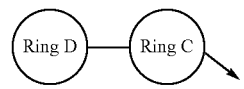

is

[Chem. 19]

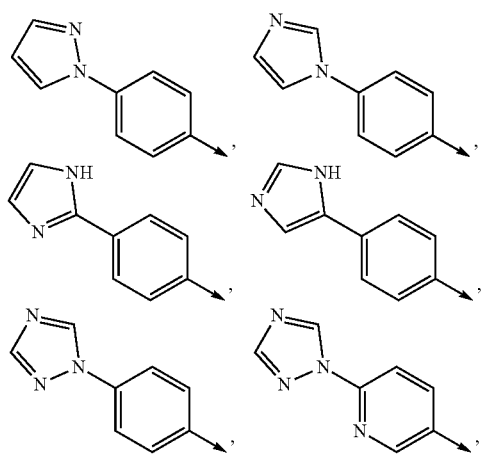

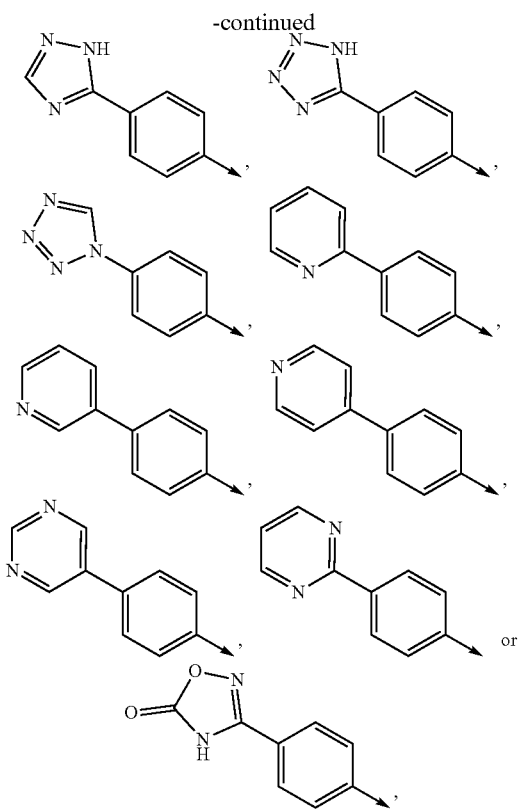

wherein arrow represents connecting position with E, each of ring corresponding to ring C may be optionally substituted with 1 to 3 R⁹, each of ring corresponding to ring D may be optionally substituted with 1 to 3 R¹⁰; or a pharmaceutically acceptable salt thereof.

15. The compound according to any one of the 1, 2, 6 and 10 to 14, wherein

[Chem. 20]

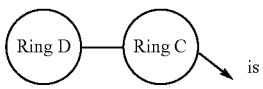 is

[Chem. 21]

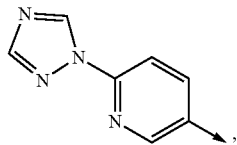

wherein arrow represents connecting position with E, each of ring corresponding to ring C may be optionally substituted with 1 to 3 R⁹, each of ring corresponding to ring D may be optionally substituted with 1 to 3 R¹⁰; or a pharmaceutically acceptable salt thereof.

16. The compound according to 1, wherein the compound is
(1) N-[2-methoxy-4-(trifluoromethoxy)benzyl][1,2,4]triazolo[4,3-a]pyridine-7-carboxamide,
(2) N-[2-methyl-4-(trifluoromethoxy)benzyl][1,2,4]triazolo[1,5-a]pyridine-6-carboxamide,
(3) N-[2-fluoro-4-(trifluoromethoxy)benzyl][1,2,4]triazolo[1,5-a]pyridine-6-carboxamide,
(4) N-[2-methyl-4-(trifluoromethoxy)benzyl]-6-(1H-1,2,4-triazol-1-yl)nicotinamide,
(5) N-[2-methoxy-4-(trifluoromethoxy)benzyl]-4-(5-oxo-4,5-dihydro-1,2,4-oxadiazol-3-yl)benzamide,
(6) N-[[2-chloro-4-(trifluoromethoxy)phenyl]methyl]-[1,2,4]triazolo[4,3-a]pyridine-7-carboxamide,
(7) N-[[2-chloro-4-(trifluoromethoxy)phenyl]methyl]-[1,2,4]triazolo[1,5-a]pyridine-6-carboxamide, or
(8) N-[[2-chloro-4-(trifluoromethoxy)phenyl]methyl]-1-methylbenzotriazole-5-carboxamide, or a pharmaceutically acceptable salt thereof.

17. A pharmaceutical composition comprising a therapeutically effective amount of a compound of formula (I), or a pharmaceutically acceptable salt thereof, and a pharmaceutically acceptable carrier.

18. The pharmaceutical composition according to 17, for treating and/or preventing a disorder associated with TREK-1, TREK-2 or both TREK-1 and TREK-2 channels dysfunction.

19. The pharmaceutical composition according to 17 or 18, which is a pharmaceutical composition comprising a therapeutically effective amount of a compound of formula (1c-1-1):

[Chem. 22]

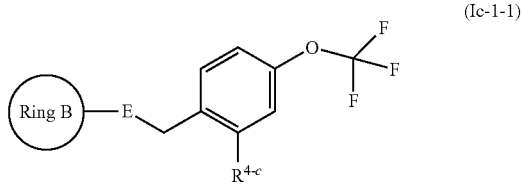

wherein all symbols are as defined in 1, 3 or 4; or a pharmaceutically acceptable salt thereof, and a pharmaceutically acceptable carrier.

20. The pharmaceutical composition according to 19, wherein
Ring B is

[Chem. 23]

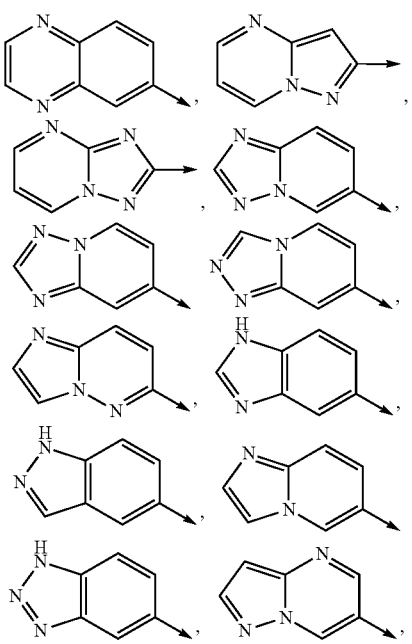

-continued

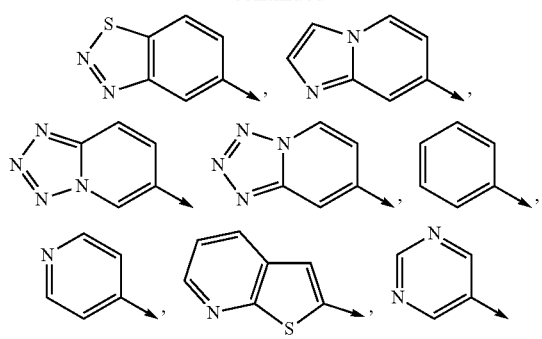

wherein arrow represents connecting position with E, each of which may be optionally substituted with 1 to 3 $R^8$.

21. The pharmaceutical composition according to 19 or 20, wherein

Ring B is

[Chem. 24]

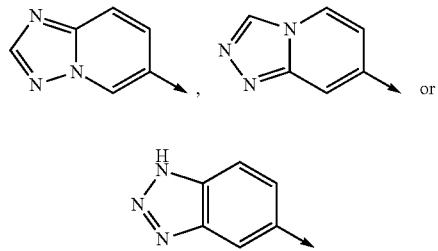

wherein arrow represents connecting position with E, each of which may be optionally substituted with 1 to 3 $R^8$.

22. The pharmaceutical composition according to 17 or 18, which is a pharmaceutical composition comprising a therapeutically effective amount of a compound of formula (1d-1-1):

[Chem. 25]

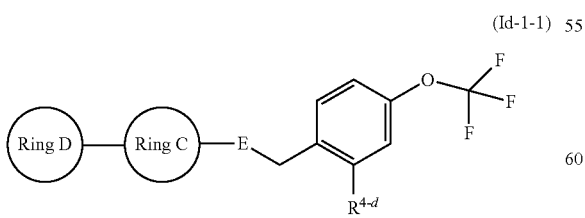

wherein all symbols are as defined in 1, 10 or 11; or a pharmaceutically acceptable salt thereof, and a pharmaceutically acceptable carrier.

23. The pharmaceutical composition according to 22, wherein

[Chem. 26]

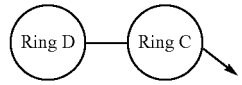

is

[Chem. 27]

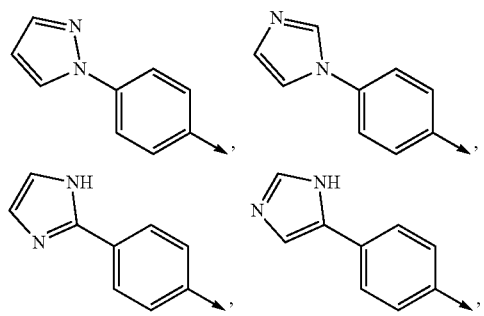

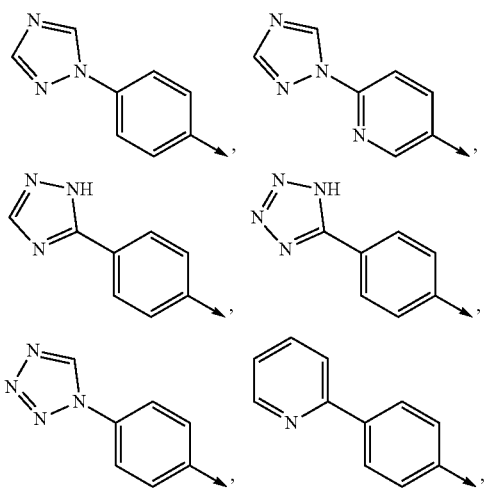

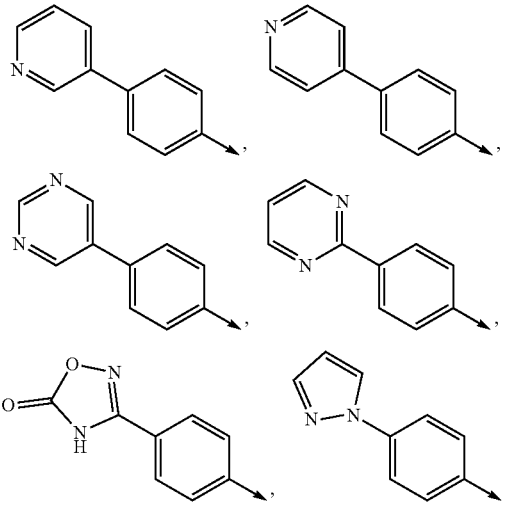

-continued

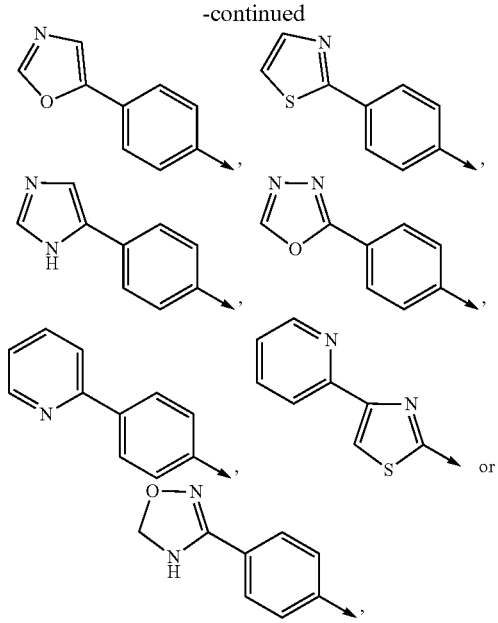

wherein arrow represents connecting position with E, each of ring corresponding to ring C may be optionally substituted with 1 to 3 $R^9$, each of ring corresponding to ring D may be optionally substituted with 1 to 3 $R^{10}$.

24. The pharmaceutical composition according to 22 or 23, wherein

[Chem. 28]

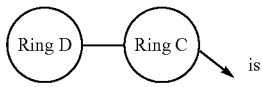

[Chem. 29]

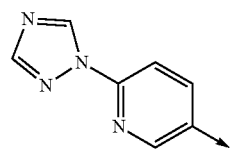

wherein arrow represents connecting position with E, each of ring corresponding to ring C may be optionally substituted with 1 to 3 $R^9$, each of ring corresponding to ring D may be optionally substituted with 1 to 3 $R^{10}$.

25. The pharmaceutical composition according to 17 or 18, which is a pharmaceutical composition comprising a therapeutically effective amount of a compound of formula (1e-1):

[Chem. 30]

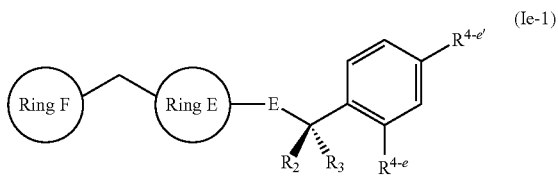

wherein
$R^{4-e}$ and $R^{4-e'}$ are independently halo, $SF_5$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, or $C_1$-$C_4$-haloalkylthio;
Ring E is benzene or 5-6 membered heteroaryl, which may be optionally substituted with 1 to 3 $R^{9-e}$; wherein multiple $R^{9-e}$ may be the same as or different from each other;
$R^{9-e}$ is halogen, hydroxyl, $C_1$-$C_4$-alkyl, $C_1$-$C_4$-haloalkyl, $C_1$-$C_4$-alkoxy, or $C_1$-$C_4$-haloalkoxy;
Ring F represents benzene, 5-6 membered heterocycle or 5-6 membered heteroaryl, which may be optionally substituted with 1 to 3 $R^{10-e}$; wherein multiple $R^{10-e}$ may be the same as or different from each other;
$R^{10-e}$ is halogen, hydroxyl, oxo, $C_1$-$C_4$-alkyl, $C_1$-$C_4$-haloalkyl, $C_1$-$C_4$-alkoxy, or $C_1$-$C_4$-haloalkoxy,
the other symbols are as defined in 1; or
a pharmaceutically acceptable salt thereof, and a pharmaceutically acceptable carrier.

26. The pharmaceutical composition according to 25, which is a pharmaceutical composition comprising a therapeutically effective amount of a compound of formula (1e-1), wherein

[Chem. 31]

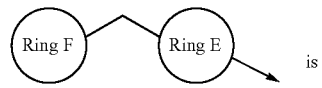

[Chem. 32]

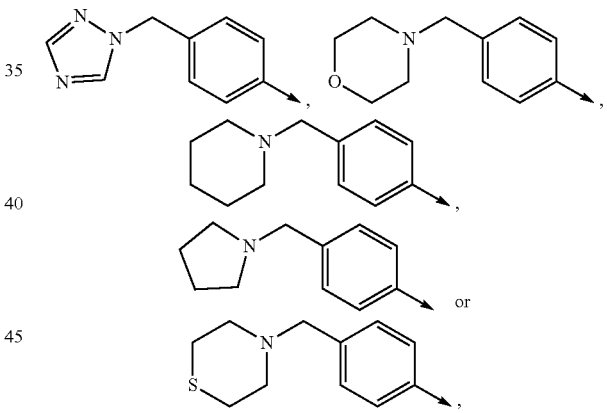

wherein arrow represents connecting position with E, each of ring corresponding to ring E may be optionally substituted with 1 to 3 $R^{9-e}$, each of ring corresponding to ring F may be optionally substituted with 1 to 3 $R^{10-e}$; or a pharmaceutically acceptable salt thereof, and a pharmaceutically acceptable carrier.

27. The pharmaceutical composition according to 17 or 18, which is a pharmaceutical composition comprising a therapeutically effective amount of a compound which is selected from
(1) N-[2-(4-chloro-2-methylphenoxy)ethyl]-2-thiophenecarboxamide,
(2) N-(2,4-dichlorobenzyl)-4-[(methylsulfonyl)amino]benzamide,
(3) N-(4-bromo-2-chlorobenzyl)-4-(1H-1,2,4-triazol-5-yl) benzamide,
(4) N-(2,4-dichlorobenzyl)-4-(1H-1,2,4-triazol-1-yl)benzamide, (5) N-(4-bromo-2-chlorobenzyl)-4-(1H-pyrazol-1-yl)benzamide,
(6) 4-(1H-tetrazol-1-yl)-N-[4-(trifluoromethoxy)benzyl]benzamide,
(7) N-[4-(trifluoromethoxy)benzyl]-1H-benzimidazole-5-carboxamide, or
(8) 4-(1H-1,2,4-triazol-1-yl)-N-[4-(trifluoromethoxy)benzyl]benzamide, or a pharmaceutically acceptable salt thereof, and a pharmaceutically acceptable carrier.

28. A pharmaceutical composition for treating and/or preventing a disorder associated with TREK-1, TREK-2 or both TREK-1 and TREK-2 channels dysfunction comprising a therapeutically effective amount of a compound which is selected from
(1) N-(2,4-dichlorobenzyl)-1H-benzimidazole-5-carboxamide, or
(2) N-[4-(trifluoromethoxy)benzyl]-1H-indazole-5-carboxamide, or
a pharmaceutically acceptable salt thereof, and a pharmaceutically acceptable carrier.

29. A method for treating and/or preventing a disorder associated with TREK-1, TREK-2 or both TREK-1 and TREK-2 channels dysfunction, comprising administering to the mammal a therapeutically effective amount of a compound of any one of the 1 to 16, or a pharmaceutically acceptable salt thereof.

30. The method of 29, wherein the disorder associated with TREK-1, TREK-2 or both TREK-1 and TREK-2 channels dysfunction is pain, nasal inflammation, atrial fibrillation, acute respiratory distress syndrome, acute lung injury, overactive bladder, cerebral ischemia, epilepsy, amyotrophic lateral sclerosis, neuronal degenerative diseases (e.g. Alzheimer's disease), sepsis, pancreatic cancer, Cushing's syndrome, autosomal dominant polycystic kidney disease, bone fracture, osteoporosis, temporal lobe epilepsy, schizophrenia, colitis, or addiction.

31. A therapeutic and/or prophylactic agent for atrial fibrillation, the agent comprising a compound of formula (I) or a pharmaceutically acceptable salt thereof, which is administered in combination with at least an agent selected from the group consisting of β-blockers and digoxin.

32. A therapeutic and/or prophylactic agent for pain, the agent comprising a compound of formula (I) or a pharmaceutically acceptable salt thereof, which is administered in combination with at least an agent selected from the group consisting of acetaminophen, nonsteroid antiinflammatory drug, opioid, antidepressant, antiepileptic agent, N-methyl-D-aspartate antagonist, muscle relaxant, antiarrhythmic agent, steroid and bisphosphonate.

33. A kit comprising (a) a compound of any one of the 1 to 16 or a pharmaceutically acceptable salt thereof, and (b) instructions for treating and/or preventing a disorder associated with TREK-1, TREK-2 or both TREK-1 and TREK-2 channels dysfunction.

34. A therapeutic and/or prophylactic agent for a disorder associated with TREK-1, TREK-2 or both TREK-1 and TREK-2 channels dysfunction, the agent comprising a compound of any one of the 1 to 16, or a pharmaceutically acceptable salt thereof.

35. Use of a compound of any one of the 1 to 16, or a pharmaceutically acceptable salt thereof, for producting of a therapeutic and/or prophylactic agent for a disorder associated with TREK-1, TREK-2 or both TREK-1 and TREK-2 channels dysfunction.

36. A compound of any one of the 1 to 16, or a pharmaceutically acceptable salt thereof for use in treating and/or preventing of a disorder associated with TREK-1, TREK-2 or both TREK-1 and TREK-2 channels dysfunction.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise.

The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* 3$^{rd}$ Edition, Cambridge University Press, Cambridge, 1987; the entire contents of each of which are incorporated herein by reference.

The term "alkoxy," as used herein, refers to an alkyl group, as defined herein, appended to the parent molecular moiety through an oxygen atom. Representative examples of alkoxy include, but are not limited to, methoxy, ethoxy, n-propoxy, iso-propoxy, n-butoxy, sec-butoxy, iso-butoxy, and tert-butoxy.

The term "$C_1$-$C_4$-alkoxy" as used herein, refers to an $C_1$-$C_4$-alkyl group, as defined herein, appended to the parent molecular moiety through an oxygen atom. Representative examples of $C_1$-$C_4$-alkoxy include, but are not limited to, methoxy, ethoxy, n-propoxy, iso-propoxy, n-butoxy, sec-butoxy, iso-butoxy, and tert-butoxy.

The term "alkyl," as used herein, means a straight or branched, saturated hydrocarbon chain containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "$C_1$-$C_4$-alkyl" means a straight or branched chain hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl.

The term "alkenyl," as used herein, means a straight or branched, hydrocarbon chain containing at least one carbon-carbon double bond and from 2 to 10 carbon atoms.

The term "alkynyl," as used herein, means a straight or branched, hydrocarbon chain containing at least one carbon-carbon triple bond and from 2 to 10 carbon atoms.

The term "$C_1$-$C_4$-alkylthio," as used herein, means a $C_1$-$C_4$-alkyl group, as defined herein, is appended to the parent molecular moiety through a sulfer atom, as defined herein.

The term "$C_1$-$C_4$-haloalkylthio," as used herein, means a $C_1$-$C_4$-haloalkyl group, as defined herein, is appended to the parent molecular moiety through a sulfer atom.

The term "aryl," as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, tetrahydroquinolinyl, indazolyl, benzimidazolyl, benzo[1,2,3]triazolyl, benzo[1,2,3]thiadiazolyl, 2,3-dihydro-1H-indolyl, benzomorpholinyl and quinoxalinyl.

The term "arylalkyl," as used herein, means a aryl group, as defined herein, is appended to the parent molecular moiety through a $C_1$-$C_4$-alkyl group, as defined herein.

The term "cycloalkyl," as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl. "Cycloalkyl" also includes carbocyclic ring systems in which a cycloalkyl group is appended to the parent molecular moiety and is fused to an aryl group as defined herein (e.g., a phenyl group), a heteroaryl group as defined herein, or a heterocycle as defined herein.

The term "cycloalkylalkyl," as used herein, means a cycloalkyl group, as defined herein, is appended to the parent molecular moiety through a $C_1$-$C_4$-alkyl group, as defined herein.

The term "halogen" or "halo," as used herein, means Cl, Br, I, or F.

The term "$C_1$-$C_4$-haloalkyl," as used herein, means a $C_1$-$C_4$-alkyl group, as defined herein, in which one, two, three, four, five, six, seven or eight hydrogen atoms are replaced by a halogen.

The term "$C_1$-$C_4$-haloalkoxy," as used herein, means a $C_1$-$C_4$-haloalkyl group, as defined herein, is appended to the parent molecular moiety through an oxygen atom.

The term "halocycloalkyl," as used herein, means a cycloalkyl group, as defined herein, in which one or more hydrogen atoms are replaced by a halogen.

The term "heteroalkyl," as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl," as used herein, refers to an aromatic monocyclic ring or an aromatic bicyclic ring system. The aromatic monocyclic rings are five or six membered rings containing at least one heteroatom independently selected from the group consisting of N, O and S (e.g. 1, 2, 3, or 4 heteroatoms independently selected from O, S, and N), and are appended to the parent molecular moiety through any carbon atom or any nitrogen atom. The five membered aromatic monocyclic rings have two double bonds and the six membered aromatic monocyclic rings have three double bonds. The bicyclic heteroaryl groups are exemplified by a monocyclic heteroaryl ring appended to the parent molecular moiety through any carbon atom or any nitrogen atom and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl, benzopyrazolyl, 1,2,3-triazolyl, 1,3,4-thiadiazolyl, tetrazolyl, 1,2,4-thiadiazolyl, 1,3,4-oxadiazolyl, 1,2,4-oxadiazolyl, imidazolyl, thiazolyl, isothiazolyl, triazolyl, thienyl, benzimidazolyl, benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl, quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl, imidazo[1,2-b]pyridazinyl, naphthyridinyl, pyridoimidazolyl, thiazolo[5,4-b]pyridin-2-yl, thiazolo[5,4-d]pyrimidin-2-yl, [1,2,4]triazolo[1,5-a]pyridinyl, [1,2,4]triazolo[4,3-a]pyridinyl, [1,2,4]triazolo[1,5-a]pyrimidinyl, pyrazolo[1,5-a]pyrimidinyl, 1,2,4-triazolyl, benzo[1,2,3]thiadiazolyl, tetrazolo[1,5-a]pyridinyl, benzo[1,2,3]triazolyl, or thieno[2,3-b]pyridinyl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, benzomorpholinyl, 2,3-dihydroisoquinolinyl, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0] hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, tetrahydroisoquinolinyl, [1,2,4]triazolo[1,5-a]pyridinyl or [1,2,4]triazolo[4,3-a] pyridinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalenyl, hexahydro-2H-2,5-methanocyclopenta[b]furanyl, hexahydro-1H-1,4-methanocyclopenta[c]furanyl, aza-adamantanyl (1-azatricyclo[3.3.1.13,7]decanyl), and oxa-adamantanyl (2-oxatricyclo[3.3.1.13,7]decanyl). The monocyclic, bicyclic, and tricyclic heterocycles are connected to the parent molecular moiety through any carbon atom or any nitrogen atom contained within the rings.

The term "hydroxyl" or "hydroxy", as used herein, means an —OH group.

The term "alkoxy" of "alkoxyfluoroalkyl", as used herein, represents the same meanings as the "alkoxy" described above. The term "alkyl" of "alkoxyfluoroalkyl", as used herein, represents the same meanings as the "alkyl" described above.

The term "heteroaryl" of "heteroarylalkyl", as used herein, represents the same meanings as the "heteroaryl" described above. The term "alkyl" of "heteroarylalkyl", as used herein, represents the same meanings as the "alkyl" described above.

The term "alkyl" of "hydroxyalkyl", as used herein, represents the same meanings as the "alkyl" described above.

The term "alkoxy" of "alkoxyalkyl", as used herein, represents the same meanings as the "alkoxy" described above. The term "alkyl" of "alkoxyalkyl", as used herein, represents the same meanings as the "alkyl" described above.

The term "aryl" of "aryloxy", as used herein, represents the same meanings as the "aryl" described above.

The term "alkyl" of "alkylamino", as used herein, represents the same meanings as the "alkyl" described above.

The term "alkyl" of "aminoalkyl", as used herein, represents the same meanings as the "alkyl" described above.

The term "aryl" of "arylamino", as used herein, represents the same meanings as the "aryl" described above.

The term "alkyl" of "alkylsulfonyl", as used herein, represents the same meanings as the "alkyl" described above.

The term "aryl" of "arylsulfonyl", as used herein, represents the same meanings as the "aryl" described above.

The term "cycloalkenyl", as used herein, refers to a carbocyclic ring system containing three to ten carbon atoms, zero heteroatoms, at least one carbon-carbon double bond and from 2 to 10 carbon atoms.

The term "aryl" of "arylalkyl", as used herein, represents the same meanings as the "aryl" described above. The term "alkyl" of "arylalkyl", as used herein, represents the same meanings as the "alkyl" described above.

The term "heterocycle" of "heterocyclealkyl", as used herein, represents the same meanings as the "heterocycle" described above. The term "alkyl" of "heterocyclealkyl", as used herein, represents the same meanings as the "alkyl" described above.

The term "alkyl" of "alkylsulfonylamino", as used herein, represents the same meanings as the "alkyl" described above.

The term "substituents" refers to a group "substituted" on other group. Any atom can be substituted.

The term "substituted" refers to a group that may be further substituted with one or more non-hydrogen substituent groups. Substituent groups include, but are not limited to, halogen, =O (oxo), =S (thioxo), cyano, nitro, alkoxyfluoroalkyl, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, heterocyclealkyl, arylalkyl, hydroxy, hydroxyalkyl, alkoxy, alkoxyalkyl, alkylene, aryloxy, phenoxy, benzyloxy, amino, alkylamino, alkylaminocarbonyl, acylamino, aminoalkyl, arylamino, sulfonylamino, sulfinylamino, sulfonyl, alkylsulfonyl, arylsulfonyl, aminosulfonyl, alkylsulfonylamino, sulfinyl, —COOH, ketone, amide, carbamate, and acyl. For example, if a group is described as being "optionally substituted" (such as an alkyl, alkenyl, alkynyl, aryl, heteroaryl, cycloalkyl, heteroalkyl, heterocycle or other group such as an R group), it may have 0, 1, 2, 3, 4 or 5 substituents independently selected from halogen, =O (oxo), =S (thioxo), cyano, nitro, alkoxyfluoroalkyl, alkyl, alkenyl, alkynyl, haloalkyl, haloalkoxy, heteroalkyl, cycloalkyl which may be substituted with 0, 1, 2, 3, 4 or 5 substituents selected from the groups consisting of fluoro, chloro, bromo, methyl, ethyl, n-propyl, iso-propyl, cyclopropyl, amino and =O (oxo), cycloalkenyl which may be substituted with 0, 1, 2, 3, 4 or 5 substituents selected from the groups consisting of fluoro, chloro, bromo, methyl, ethyl, n-propyl, iso-propyl, cyclopropyl, amino and =O (oxo), aryl which may be substituted with 0, 1, 2, 3, 4 or 5 substituents selected from the groups consisting of fluoro, chloro, bromo, methyl, ethyl, n-propyl, iso-propyl, cyclopropyl, amino and =O (oxo), heteroaryl which may be substituted with 0, 1, 2, 3, 4 or 5 substituents selected from the groups consisting of fluoro, chloro, bromo, methyl, ethyl, n-propyl, iso-propyl, cyclopropyl, amino and =O (oxo), heterocycle which may be substituted with 0, 1, 2, 3, 4 or 5 substituents selected from the groups consisting of fluoro, chloro, bromo, methyl, ethyl, n-propyl, iso-propyl, cyclopropyl, amino and =O (oxo), cycloalkylalkyl which may be substituted with 0, 1, 2, 3, 4 or 5 substituents selected from the groups consisting of fluoro, chloro, bromo, methyl, ethyl, n-propyl, iso-propyl, cyclopropyl, amino and =O (oxo), heteroarylalkyl which may be substituted with 0, 1, 2, 3, 4 or 5 substituents selected from the groups consisting of fluoro, chloro, bromo, methyl, ethyl, n-propyl, iso-propyl, cyclopropyl, amino and =O (oxo), heterocyclealkyl which may be substituted with 0, 1, 2, 3, 4 or 5 substituents selected from the groups consisting of fluoro, chloro, bromo, methyl, ethyl, n-propyl, iso-propyl, cyclopropyl, amino and =O (oxo), arylalkyl which may be substituted with 0, 1, 2, 3, 4 or 5 substituents selected from the groups consisting of fluoro, chloro, bromo, methyl, ethyl, n-propyl, iso-propyl, cyclopropyl, amino and =O (oxo), hydroxy, hydroxyalkyl, alkoxy, alkoxyalkyl, alkylene, aryloxy, phenoxy, benzyloxy, amino, alkylamino, alkylaminocarbonyl, acylamino, aminoalkyl, arylamino, sulfonylamino, sulfinylamino, sulfonyl, alkylsulfonyl, arylsulfonyl, aminosulfonyl, alkylsulfonylamino, sulfinyl, —COOH, ketone, amide, alkylamide, carbamate, and acyl.

The term "substituted or optionally substituted acylamino" refers to a heterocyclecarbonylamino (e.g. piperidinylcarbonylamino, pyrrolidinylcarbonylamino, pyridinylcarbonylamino, tetrahydrothienylcarbonylamino), an acetylamino, a propyloxyamino, or a butyloxyamino which may be substituted with 1, 2 or 3 substituents selected from the groups consisting of methyl, ethyl, propyl, or =O (oxo). The term "heterocycle" of "heterocyclecarbonylamino", as used herein, represents the same meanings as the "heterocycle" described above.

The term "substituted or optionally substituted alkoxyl" refers to an alkoxyl which may be substituted with hydroxyl and amino. The term "alkoxyl", as used herein, represents the same meanings as the "alkoxyl" described above.

The term "substituted or optionally substituted alkylamino" refers to an alkylamino which may be substituted with hydroxyl and amino. The term "alkylamino", as used herein, represents the same meanings as the "alkylamino" described above.

The term "substituted or optionally substituted alkylaminocarbonyl" refers to an alkylaminocarbonyl which may be substituted with hydroxyl and amino. The term "alkyl" of "alkylaminocarbonyl", as used herein, represents the same meanings as the "alkyl" described above.

The term "activator" as used herein refers to a molecular entity (e.g., but not limited to, a ligand and a disclosed compound) that enhances the activity of the target receptor protein.

The term "ligand" as used herein refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

The term "thallium flux assay" herein refers to a fluorescence-based assay used to monitor the activity of TREK channels. Thallium is a congener of potassium that readily fluxes through the pore of TREK channels. Thallium flux is measured using a commercially available, thallium-sensitive fluorescent dye called Thallos. The detail method is described below.

The term "patch clamp technique" herein refers to the "gold standard" technique for evaluating TREK channel pharmacology. The detail method is described below.

The term "TREK activator" as used herein refers to any exogenously administered compound or agent that directly or indirectly activates the channel (TREK-1, TREK-2 or both TREK-1 and TREK-2) in an animal, in particular a mammal, for example a human.

2. Compounds

In one aspect, disclosed is a compound of formula (I):

[Chem. 33]

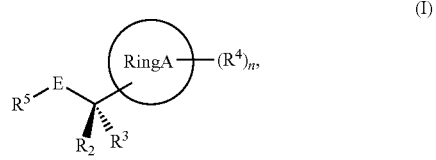

(I)

or a pharmaceutically acceptable salt thereof.

In some embodiments, the compound is a compound of formula (Ia):

[Chem. 34]

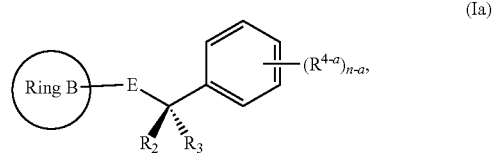

(Ia)

or a pharmaceutically acceptable salt thereof.

In some embodiments, the compound is a compound of formula (Ib):

[Chem. 35]

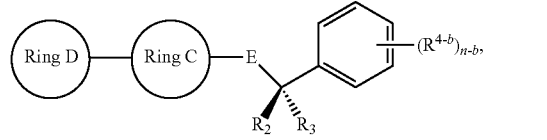

(Ib)

or a pharmaceutically acceptable salt thereof.

In some embodiments, the compound is a compound of formula (Ic):

[Chem. 36]

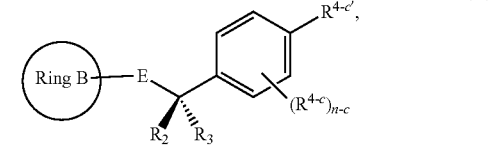

(Ic)

or a pharmaceutically acceptable salt thereof.

In some embodiments, the compound is a compound of formula (Id):

[Chem. 37]

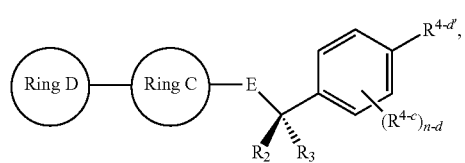

or a pharmaceutically acceptable salt thereof.

In some embodiments, the compound is a compound of formula (Ic-1):

[Chem. 38]

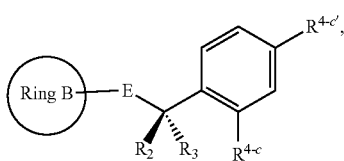

or a pharmaceutically acceptable salt thereof.

More preferable formula (I) is

[Chem. 39]

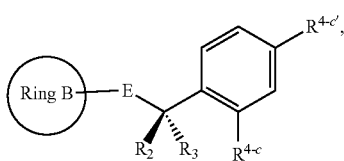

wherein Ring B is

[Chem. 40]

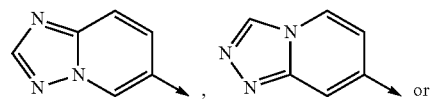,

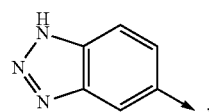, each of which may be optionally substituted with 1 to 3 $R^8$.

Far more preferable formula (I) is also

[Chem. 41]

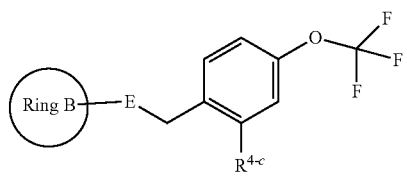

wherein Ring B is

[Chem. 42]

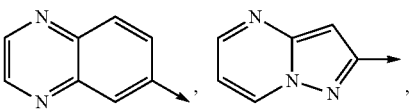

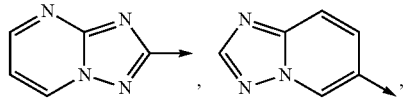

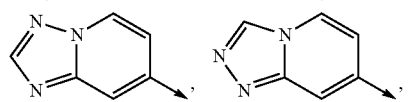

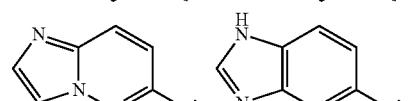

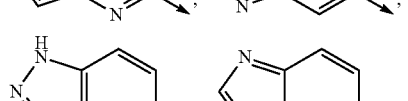

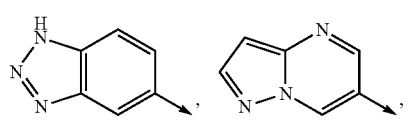

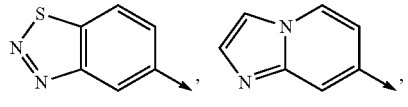

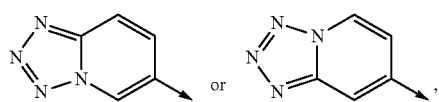

each of which may be optionally substituted with 1 to 3 $R^8$.

Most preferable formula (I) is also

[Chem. 43]

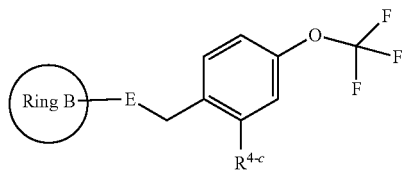
(Ic-1-1)

wherein Ring B is

[Chem. 44]

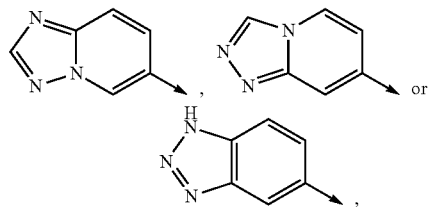

each of which may be optionally substituted with 1 to 3 $R^8$.

In some embodiments, the compound is a compound of formula (Id-1):

[Chem. 45]

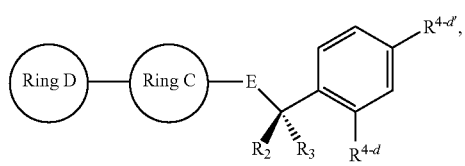
(Id-1)

or a pharmaceutically acceptable salt thereof.

More preferable formula (I) is

[Chem. 46]

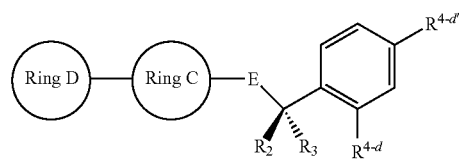
(Id-1)

wherein;

[Chem. 47]

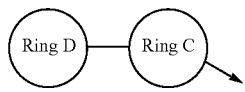

is

[Chem. 48]

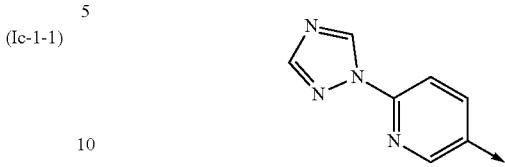

each of ring corresponding to ring C may be optionally substituted with 1 to 3 $R^9$, each of ring corresponding to ring D may be optionally substituted with 1 to 3 $R^{10}$.

Far more preferable formula (I) is also

[Chem. 49]

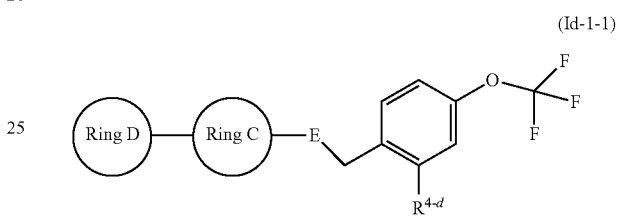
(Id-1-1)

wherein;

[Chem. 50]

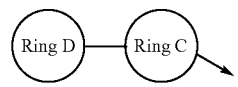

is

[Chem. 51]

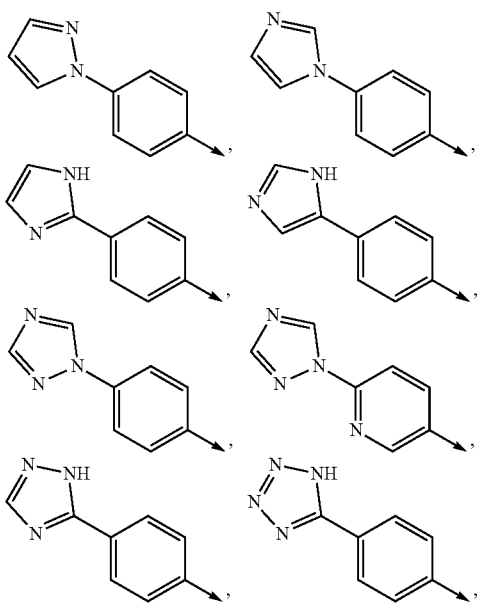

-continued

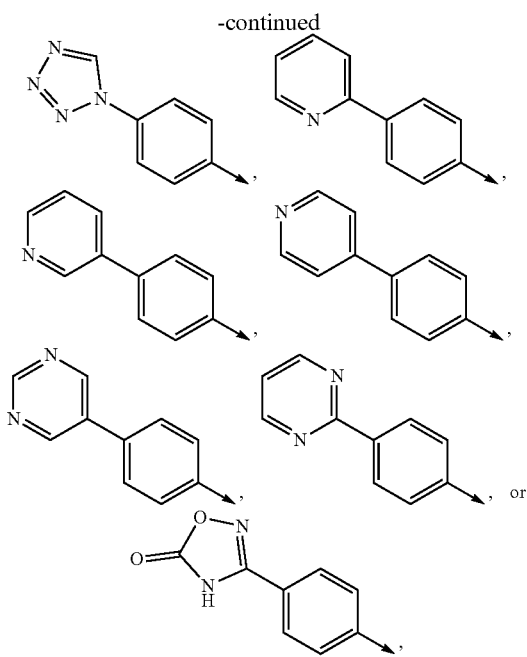

each of ring corresponding to ring C may be optionally substituted with 1 to 3 $R^9$, each of ring corresponding to ring D may be optionally substituted with 1 to 3 $R^{10}$.

Most preferable formula (I) is also

[Chem. 52]

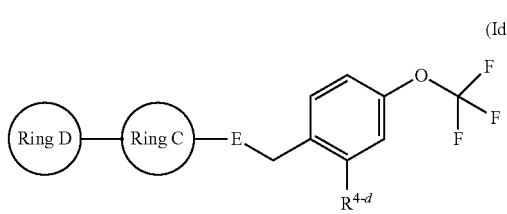
(Id-1-1)

wherein;

[Chem. 53]

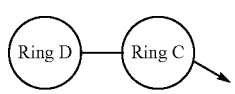

is

[Chem. 54]

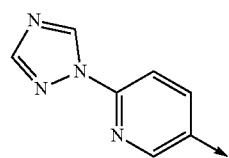

each of ring corresponding to ring C may be optionally substituted with 1 to 3 $R^9$, each of ring corresponding to ring D may be optionally substituted with 1 to 3 $R^{10}$.

More preferable formula (I) is also

[Chem. 55]

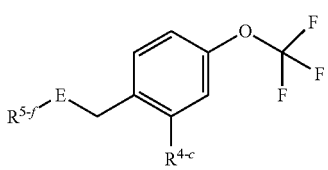
(If)

wherein $R^5$-1 is Ring B which may be optionally substituted with 1 to 3 $R^8$, or

[Chem. 56]

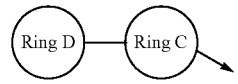

wherein Ring C may be optionally substituted with 1 to 3 $R^9$;
Ring D may be optionally substituted with 1 to 3 $R^{10}$;
arrow represents connecting position with E.

E in formula (I), (Ia), (Ib), (Ic), (Ic-1), (Ic-1-1), (Id) (Id-1), (Id-1-1), (Ie-1) and (If) is preferably —C(O)NR$^1$—. More preferable E is —C(O)NH—.

$R^2$ in formula (I), (Ia), (Ib), (Ic), (Ic-1), (Id) (Id-1) and (Ie-1) is preferably methyl or hydrogen. More preferable $R^2$ is hydrogen.

$R^3$ in formula (I), (Ia), (Ib), (Ic), (Ic-1), (Id), (Id-1) and (Ie-1) is preferably methyl or hydrogen. More preferable $R^3$ is hydrogen.

$R^2$ and $R^3$ in formula (I), (Ia), (Ib), (Ic), (Ic-1), (Id), (Id-1) and (Ie-1) are preferably hydrogen together.

Ring A in formula (I) is preferably benzene or 5-6 membered heteroaryl. More preferable Ring A is benzene.

$R^4$ in formula (I) is preferably halogen, SF$_5$, C$_1$-C$_4$-alkyl optionally substituted with halogen (C$_1$-C$_4$-alkyl or C$_1$-C$_4$-haloalkyl), —OR$^{11}$, or —SR$^{12}$. More preferable $R^4$ is halogen, SF$_5$, methyl, —CHF$_2$, —CF$_3$, —OCF$_3$, —OCHF$_2$, —SCF$_3$, or —SCHF$_2$.

$R^{4-a}$ in formula (Ia) is preferably halogen, SF$_5$, C$_1$-C$_4$-alkyl optionally substituted with halogen (C$_1$-C$_4$-alkyl or C$_1$-C$_4$-haloalkyl), —OR$^{11}$, or —SR$^{12}$. More preferable $R^{4-a}$ is halogen, SF$_5$, methyl, —OCH$_3$, —CHF$_2$, —CF$_3$, —OCF$_3$, —OCHF$_2$, —SCF$_3$, or —SCHF$_2$.

$R^{4-b}$ in formula (Ib) is preferably halogen, SF$_5$, C$_1$-C$_4$-alkyl optionally substituted with halogen (C$_1$-C$_4$-alkyl or C$_1$-C$_4$-haloalkyl), —OR$^{11}$, or —SR$^{12}$. More preferable $R^{4-b}$ is halogen, SF$_5$, methyl, —OCH$_3$, —CHF$_2$, —CF$_3$, —OCF$_3$, —OCHF$_2$, —SCF$_3$, or —SCHF$_2$.

$R^{4-c}$ in formula (Ic), (Ic-1), (Ic-1-1) and (If) is preferably halogen, SF$_5$, C$_1$-C$_4$-alkyl optionally substituted with halogen (C$_1$-C$_4$-alkyl or C$_1$-C$_4$-haloalkyl), —OR$^{11}$, or —SR$^{12}$. More preferable $R^{4-c}$ is halogen, SF$_5$, methyl, —OCH$_3$, —CHF$_2$, —CF$_3$, —OCF$_3$, —OCHF$_2$, —SCF$_3$, or —SCHF$_2$. Far more preferable $R^{4-c}$ is F, Cl, methyl, —OCH$_3$.

$R^{4-c'}$ in formula (Ic) and (Ic-1) is preferably halogen, SF$_5$, C$_1$-C$_4$-alkyl optionally substituted with halogen (C$_1$-C$_4$-alkyl or C$_1$-C$_4$-haloalkyl), —OR$^{11}$, or —SR$^{12}$. More preferable $R^{4-c'}$ is halogen, SF$_5$, methyl, —CHF$_2$, —CF$_3$, —OCF$_3$, —OCHF$_2$, —SCF$_3$, or —SCHF$_2$. Far more preferable $R^{4-c'}$ is Cl, Br, SF$_5$, —OCHF$_2$, —OCF$_3$, —SCF$_3$. Most preferable $R^{4-c'}$ is —OCF$_3$.

R$^{4\text{-}d}$ in formula (Id), (Id-1) and (Id-1-1) is preferably halogen, SF$_5$, C$_1$-C$_4$-alkyl optionally substituted with halogen (C$_1$-C$_4$-alkyl or C$_1$-C$_4$-haloalkyl), —OR$^1$, or —SR$^{12}$. More preferable R$^{4\text{-}d}$ is halogen, SF$_5$, methyl, —OCH$_3$, —CHF$_2$, —CF$_3$, —OCF$_3$, —OCHF$_2$, —SCF$_3$, or —SCHF$_2$. Far more preferable R$^{4\text{-}d}$ is F, Cl, methyl, —OCH$_3$.

R$^{4\text{-}d'}$ in formula (Id) and (Id-1) is preferably halogen, SF$_5$, C$_1$-C$_4$-alkyl optionally substituted with halogen (C$_1$-C$_4$-alkyl or C$_1$-C$_4$-haloalkyl), —OR$^1$, or —SR$^{12}$. More preferable R$^{4\text{-}d'}$ is halogen, SF$_5$, methyl, —CHF$_2$, —CF$_3$, —OCF$_3$, —OCHF$_2$, —SCF$_3$, or —SCHF$_2$. Far more preferable R$^{4\text{-}d'}$ is Cl, Br, SF$_5$, —OCHF$_2$, —OCF$_3$, —SCF$_3$. Most preferable R$^{4\text{-}d'}$ is —OCF$_3$.

R$^{4\text{-}e}$ in formula (Ie-1) is preferably halogen, SF$_5$, C$_1$-C$_4$-alkyl optionally substituted with halogen (C$_1$-C$_4$-alkyl or C$_1$-C$_4$-haloalkyl), —OR$^{11}$, or —SR$^{12}$. More preferable R$^{4\text{-}e}$ is halogen, SF$_5$, methyl, —OCH$_3$, —CHF$_2$, —CF$_3$, —OCF$_3$, —OCHF$_2$, —SCF$_3$, or —SCHF$_2$. Far more preferable R$^{4\text{-}e}$ is F, Cl, methyl, —OCH$_3$.

R$^{4\text{-}e'}$ in formula (Ie-1) is preferably halogen, SF$_5$, C$_1$-C$_4$-alkyl optionally substituted with halogen (C$_1$-C$_4$-alkyl or C$_1$-C$_4$-haloalkyl), —OR$^{11}$, or —SR$^{12}$. More preferable R$^{4\text{-}e'}$ is halogen, SF$_5$, methyl, —CHF$_2$, —CF$_3$, —OCF$_3$, —OCHF$_2$, —SCF$_3$, or —SCHF$_2$. Far more preferable R$^{4\text{-}e'}$ is Cl, Br, SF$_5$, —OCHF$_2$, —OCF$_3$, —SCF$_3$. Most preferable R$^{4\text{-}e'}$ is —OCF$_3$.

R$^{4\text{-}d'}$ in formula (Id) and (Id-1) is preferably halogen, SF$_5$, C$_1$-C$_4$-alkyl optionally substituted with halogen (C$_1$-C$_4$-alkyl or C$_1$-C$_4$-haloalkyl), —OR$^1$, or —SR$^{12}$. More preferable R$^{4\text{-}d'}$ is halogen, SF$_5$, methyl, —CHF$_2$, —CF$_3$, —OCF$_3$, —OCHF$_2$, —SCF$_3$, or —SCHF$_2$. Far more preferable R$^{4\text{-}d'}$ is Cl, Br, SF$_5$, —OCHF$_2$, —OCF$_3$, —SCF$_3$. Most preferable R$^{4\text{-}d'}$ is —OCF$_3$.

Preferable R$^{11}$ is methyl, ethyl, CHF$_2$, CF$_3$.

Preferable R$^{12}$ is methyl, ethyl, CHF$_2$, CF$_3$.

R$^5$ in formula (I) is preferably aryl or heteroaryl; each of which may be optionally substituted. More preferable R$^5$ is benzene, naphthalene, 5-10 membered heteroaryl, 5-6 membered heteroaryl-benzene-, or 5-6 membered heteroaryl-pyridine-; each of which may be optionally substituted. Far more preferable R$^5$ is

[Chem. 57]

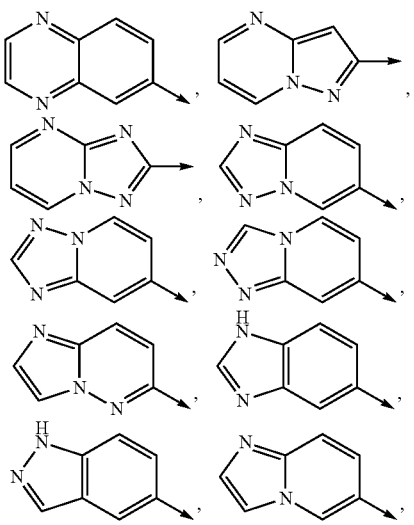

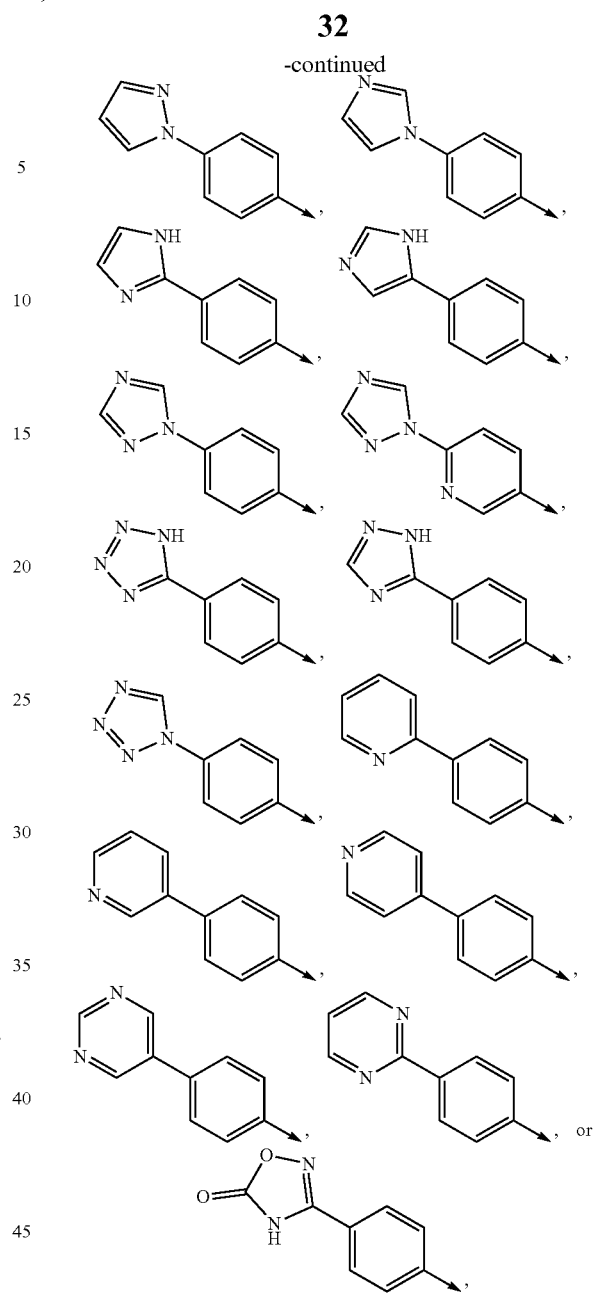

each of which may be optionally substituted.
Far more preferable R$^5$ is also

[Chem. 58]

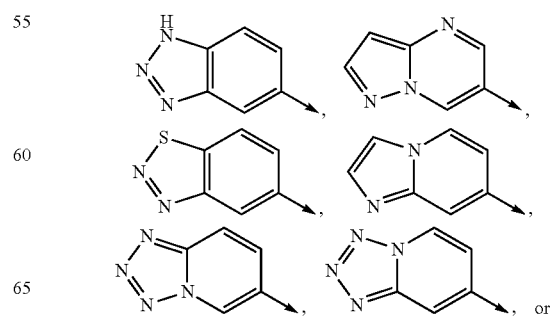

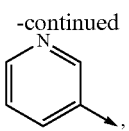

each of which may be optionally substituted.

Ring B in formula (Ia), (Ic), (Ic-1) and (Ic-1-1) is preferably benzene or 5-10 membered heteroaryl which may be optionally substituted with 1 to 3 $R^8$. More preferable Ring B is 9-10 membered heteroaryl which may be optionally substituted with 1 to 3 $R^8$. Far more preferable Ring B is

[Chem. 59]

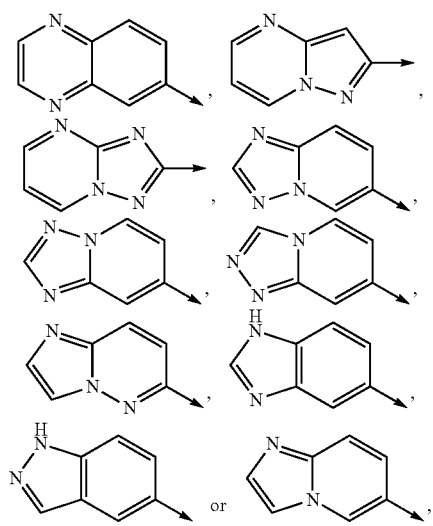

each of which may be optionally substituted with 1 to 3 $R^8$.
Far more preferable Ring B is also

[Chem. 60]

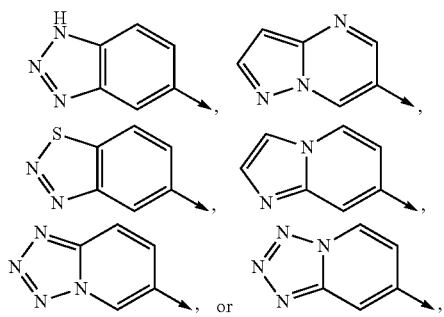

each of which may be optionally substituted with 1 to 3 $R^8$.
One example of more preferable Ring B is

[Chem. 61]

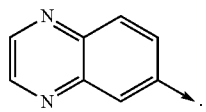

One example of more preferable Ring B is

[Chem. 62]

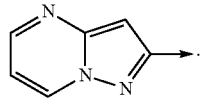

One example of more preferable Ring B is

[Chem. 63]

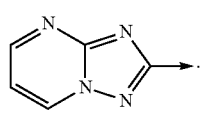

One example of more preferable Ring B is

[Chem. 64]

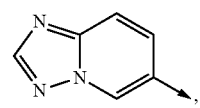

which may be optionally substituted with 1 to 3 $R^8$.
One example of more preferable Ring B is

[Chem. 65]

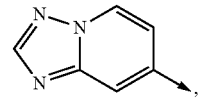

which may be optionally substituted with 1 to 3 $R^8$.
One example of more preferable Ring B is

[Chem. 66]

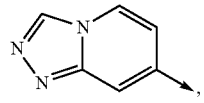

which may be optionally substituted with 1 to 3 $R^8$.
One example of more preferable Ring B is

[Chem. 67]

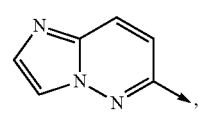

which may be optionally substituted with 1 to 3 $R^8$.

One example of more preferable Ring B is

[Chem. 68]

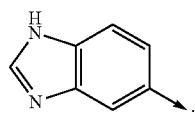

One example of more preferable Ring B is

[Chem. 69]

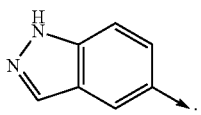

One example of more preferable Ring B is

[Chem. 70]

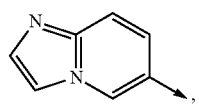

which may be optionally substituted with 1 to 3 R⁸.
One example of more preferable Ring B is

[Chem. 71]

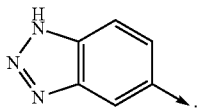

One example of more preferable Ring B is

[Chem. 72]

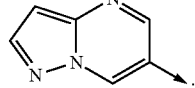

One example of more preferable Ring B is

[Chem. 73]

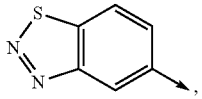

which may be optionally substituted with 1 to 3 $R^8$.

One example of more preferable Ring B is

[Chem. 74]

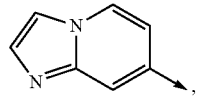

which may be optionally substituted with 1 to 3 $R^8$.
One example of more preferable Ring B is

[Chem. 75]

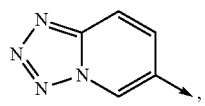

which may be optionally substituted with 1 to 3 $R^8$.
One example of more preferable Ring B is

[Chem. 76]

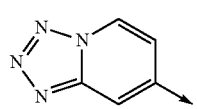

which may be optionally substituted with 1 to 3 $R^8$.
Most preferable Ring B is

[Chem. 77]

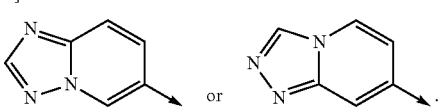

Most preferable Ring B is also

[Chem. 78]

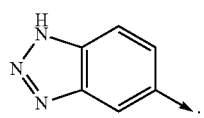

$R^8$ in Formula (Ia), (Ic), (Ic-1) and (Ic-1-1) is preferably none, or methyl. $R^8$ in Formula (Ia), (Ic), (Ic-1) and (Ic-1-1) is also preferably amino, halogen, cycloalkyl or $C_1$-$C_4$-haloalkoxy. More preferable $R^8$ is none. More preferable $R^8$ is also amino, Br, F, cyclopropyl and —OCF₃.

n-a in Formula (Ia) is preferably 1, 2, or 3. More preferable n-a is 1 or 2. Most preferable n-a is 2.

n-c in Formula (Ic) is preferably 1 or 2. More preferable n-c is 1.

Ring C in formula (Ib), (Id), (Id-1) and (Id-1-1) is preferably benzene or 5-6 membered heteroaryl, each of which may be optionally substituted with 1 to 3 $R^9$. More preferable Ring C is benzene which may be optionally substituted with 1 to 3 $R^9$. More preferable Ring C is also pyridine which may be optionally substituted with 1 to 3 $R^9$.

Ring D in formula (Ib), (Id), (Id-1) and (Id-1-1) is preferably benzene or 5-6 membered heteroaryl, each of which may be optionally substituted with 1 to 3 $R^{10}$. More preferable Ring D is 5-6 membered heteroaryl which may be optionally substituted with 1 to 3 $R^{10}$. Far more preferable Ring D is imidazole, triazole, tetrazole, pyridine, thiazole, oxazole, oxadiazole, pyrimidine, each of which may be optionally substituted with 1 to 3 $R^{10}$.

One example of far more preferable Ring D is imidazole which may be optionally substituted with 1 to 3 $R^{10}$.

One example of far more preferable Ring D is triazole which may be optionally substituted with 1 to 3 $R^{10}$.

One example of far more preferable Ring D is tetrazole which may be optionally substituted with 1 to 3 $R^{10}$.

One example of far more preferable Ring D is pyridine which may be optionally substituted with 1 to 3 $R^{10}$.

One example of far more preferable Ring D is thiazole which may be optionally substituted with 1 to 3 $R^{10}$.

One example of far more preferable Ring D is oxazole which may be optionally substituted with 1 to 3 $R^{10}$.

One example of far more preferable Ring D is oxadiazole which may be optionally substituted with 1 to 3 $R^{10}$.

One example of far more preferable Ring D is pyrimidine which may be optionally substituted with 1 to 3 $R^{10}$.

[Chem. 79]

in formula (Ib), (Id) and (Id-1) is preferably

[Chem. 80]

each of ring corresponding to ring C may be optionally substituted with 1 to 3 $R^9$, each of ring corresponding to ring D may be optionally substituted with 1 to 3 $R^{10}$.

One example of preferable

[Chem. 81]

is

[Chem. 82]

One example of preferable

[Chem. 83]

is

[Chem. 84]

One example of preferable

[Chem. 85]

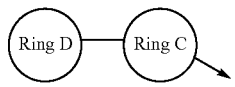

is

[Chem. 86]

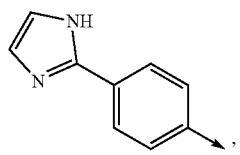

wherein imidazole ring may be optionally substituted with 1 to 3 $R^{10}$.

One example of preferable

[Chem. 87]

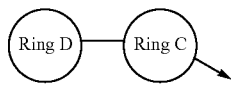

is

[Chem. 88]

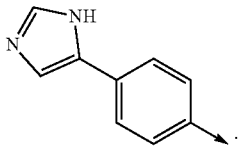

One example of preferable

[Chem. 89]

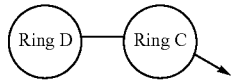

is

[Chem. 90]

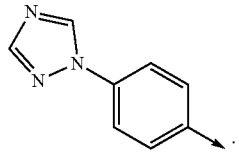

One example of preferable

[Chem. 91]

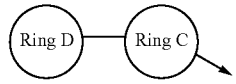

is

[Chem. 92]

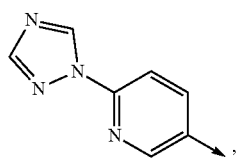

wherein triazole ring may be optionally substituted with 1 to 3 $R^{10}$.

One example of preferable

[Chem. 93]

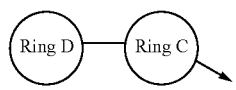

is

[Chem. 94]

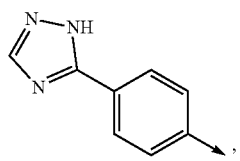

wherein triazole ring may be optionally substituted with 1 to 3 $R^{10}$.

One example of preferable

[Chem. 95]

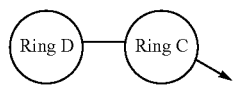

is

[Chem. 96]

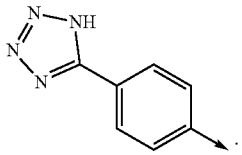

One example of preferable
[Chem. 97]
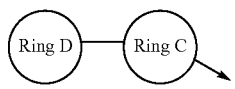
[Chem. 98]
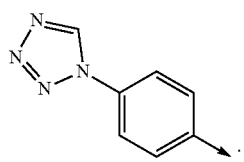
One example of preferable
[Chem. 99]
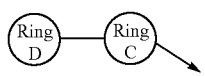
is
[Chem. 100]
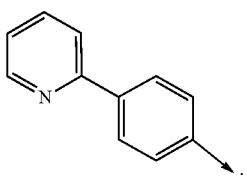
One example of preferable
[Chem. 101]
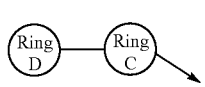
is
[Chem. 102]
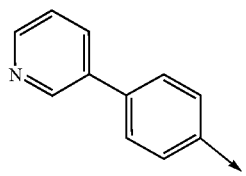
One example of preferable
[Chem. 103]
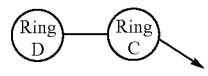
is
[Chem. 104]
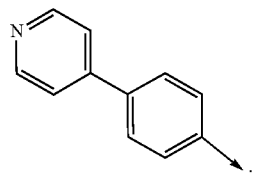
One example of preferable
[Chem. 105]
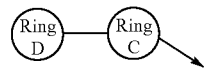
is
[Chem. 106]
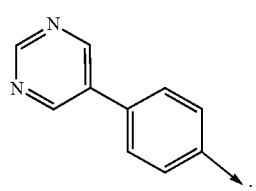
One example of preferable
[Chem. 107]
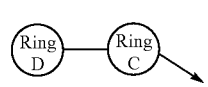
is
[Chem. 108]
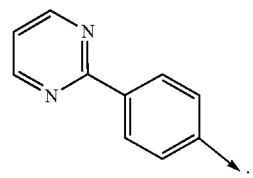

One example of preferable

[Chem. 109]

Ring D—Ring C → is

[Chem. 110]

(3-(4-substituted-phenyl)-1,2,4-oxadiazol-5(4H)-one structure)

Most preferable

[Chem. 111]

Ring D—Ring C → is

[Chem. 112]

(2-(1,2,4-triazol-1-yl)-5-substituted-pyridine structure)

$R^9$ in Formula (Id), (Id-1) and (Id-1-1) is preferably none, halogen or methyl. More preferable $R^9$ is none, Br or methyl.

$R^{10}$ in Formula (Id), (Id-1) and (Id-1-1) is preferably none, halogen or methyl. More preferable $R^{10}$ is none, Br or methyl.

Ring E in Formula (Ie-1) is preferably benzene which may be optionally substituted with 1 to 3 $R^{9\text{-}e}$.

Ring F in Formula (Ie-1) is preferably 1,2,4-triazole, morpholine, piperidine, pyrrolidine or thiomorpholine, each of which may be optionally substituted with 1 to 3 $R^{10\text{-}e}$.

$R^{9\text{-}e}$ in Formula (Ie-1) is preferably none.

$R^{10\text{-}e}$ in Formula (Ie-1) is preferably none, halogen, methyl or oxo.

n-b in Formula (Ib) is preferably 1, 2, or 3. More preferable n-b is 1 or 2. Most preferable n-b is 2.

n-d in Formula (Id) is preferably 1, or 2. More preferable n-d is 1.

The compound of formula (I) is preferably such a compound that some or all of the above-mentioned preferred examples for Ring A, E, $R^1$, $R^2$, $R^3$, $R^4$, $R^1$, and n are combined.

The compound of formula (Ia) is preferably such a compound that some or all of the above-mentioned preferred examples for Ring B, E, $R^1$, $R^2$, $R^3$, $R^{4\text{-}a}$, and n-a are combined.

The compound of formula (Ib) is preferably such a compound that some or all of the above-mentioned preferred examples for Ring C, Ring D, E, $R^1$, $R^2$, $R^3$, $R^{4\text{-}b}$, and n-b are combined.

The compound of formula (Ic) is preferably such a compound that some or all of the above-mentioned preferred examples for Ring B, E, $R^1$, $R^2$, $R^3$, $R^{4\text{-}c}$, $R^{4\text{-}c'}$, and n-c are combined.

The compound of formula (Ic-1) is preferably such a compound that some or all of the above-mentioned preferred examples for Ring B, E, $R^1$, $R^2$, $R^3$, $R^{4\text{-}c}$, and $R^{4\text{-}c'}$ are combined.

The compound of formula (Ic-1-1) is preferably such a compound that some or all of the above-mentioned preferred examples for Ring B, E, $R^1$, and $R^{4\text{-}c}$ are combined.

The compound of formula (Id) is preferably such a compound that some or all of the above-mentioned preferred examples for Ring C, Ring D, E, $R^1$, $R^2$, $R^3$, $R^{4\text{-}d}$, $R^{4\text{-}d'}$, and n-d are combined.

The compound of formula (Id-1) is preferably such a compound that some or all of the above-mentioned preferred examples for Ring C, Ring D, E, $R^1$, $R^2$, $R^3$, $R^{4\text{-}d}$, and $R^{4\text{-}d'}$ are combined.

The compound of formula (Id-1-1) is preferably such a compound that some or all of the above-mentioned preferred examples for Ring C, Ring D, E, $R^1$, and $R^{4\text{-}d}$ are combined.

The compound of formula (Ie-1) is preferably such a compound that some or all of the above-mentioned preferred examples for Ring E, Ring F, E, $R^1$, $R^2$, $R^3$, $R^{4\text{-}e}$, and $R^{4\text{-}e'}$ are combined.

In addition, all of compounds mentioned in section "Examples" are preferred.

Compound names are assigned by using the Struct=Name naming algorithm as part of CHEMDRAW (registered trademark) ULTRA v. 15.0 or ACD/Name Batch (registered trademark).

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

It should be understood that the compound may possess tautomeric forms, as well as geometric isomers, and that these also constitute embodiments of the disclosure.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

a. Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, ethanesulfonate, glucuronate, gluconate, glycerophosphate, hemisulfate, heptanoate, hexanoate, formate, isethionate, fumarate, lactate, malate, maleate, malonate, methanesulfonate, naphthylenesulfonate, nicotinate, nitrate, oxalate, pamoate, pectinate, persulfate, 3-phenylpropionate, picrate, oxalate, pivalate, propionate, succinate, tartrate, trichloroacetate, trifluoroacetate, glutamate, para-toluenesulfonate, undecanoate, hydrochloric, hydrobromic, hydroiodic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

In the present invention, all the mentions of the compound of the present invention include a compound represented by formula (I), or a salt, a solvate, or a cocrystal thereof.

The compound represented by formula (I) and a salt thereof may be present in a not-solvation form, or in a solvation form with pharmaceutically acceptable solvent such as water or ethanol. Preferable solvates include hydrate. The compound represented by formula (I) and a salt thereof can be converted into a solvate by a well-known method.

The compound represented by formula (I) can form a cocrystal with an appropriate cocrystal former. As the cocrystal, pharmaceutically acceptable cocrystal that is formed with a pharmaceutically acceptable cocrystal former is preferable. The cocrystal is typically defined as a crystal that is formed of two or more different molecules by intermolecular interaction that is different from ionic bond. Furthermore, the cocrystal may be a composite of a neutral molecule and a salt. The cocrystal can be prepared by recrystallization from a solvent by a well-known method, for example, melting crystallization, or physically pulverizing the components together. Appropriate cocrystal formers include ones described in WO2006/007448.

The prodrug of the compound represented by the formula (I) refers to a compound which is converted in vivo to the compound represented by the formula (I) by the reaction with enzymes, gastric acid and the like. Examples of the prodrug of the compound represented by the formula (I) include, when the compound represented by the formula (I) has an amino group, compounds in which the amino group is acylated, alkylated or phosphorylated (e.g. compounds represented by the formula (I) in which the amino group thereof is converted to eicosanoyl, aranyl, pentylaminocarbonyl, (5-methyl-2-oxo-1,3-dioxolen-4-yl)methoxycarbonyl, tetrahydrofuranyl, pyrrolidylmethyl, pivaloyloxymethyl, acetoxymethyl, tert-butyl or the like); when the compound represented by the formula (I) has a hydroxy group, compounds in which the hydroxy group is acylated, alkylated, phosphorylated or converted to borate (e.g. compounds represented by the formula (I) in which the hydroxy group thereof is converted to acetyl, palmitoyl, propanoyl, pivaloyl, succinyl, fumaryl, alanyl, dimethylaminomethylcarbonyl or the like); when the compound represented by the formula (I) has a carboxy group, compounds in which the carboxy group is esterified or amidated (e.g. compounds represented by the formula (I) in which the carboxy group thereof is converted to methyl ester, ethyl ester, isopropyl ester, phenyl ester, carboxymethyl ester, dimethylaminomethyl ester, pivaloyloxymethyl ester, phthalidyl ester, 1-{(ethoxycarbonyl)oxy}ethyl ester, (5-methyl-2-oxo-1,3-dioxolen-4-yl)methyl ester, 1-{[(cyclohexyloxy)carbonyl]oxy}ethyl ester, methylamide or the like) and the like. The prodrug of the compound represented by the formula (I) may be the one which is converted to the compound represented by the formula (I) under the physiological condition such as those disclosed in "Iyakuhin no Kaihatsu", vol. 7 "Bunshi Sekkei", p. 163-198, 1990, Hirokawa Shoten Co.

b. General Synthesis

Compounds of formula (I) may be prepared by synthetic processes or by metabolic processes. Preparation of the compounds by metabolic processes includes those occurring in the human or animal body (in vivo) or processes occurring in vitro.

Abbreviations which have been used in the descriptions of the Schemes that follow are: DIPEA is N,N-diisopropylethylamine; CO is carbon monoxide; Pd(dppf)Cl$_2$·CH$_2$Cl$_2$ is [1,1'-Bis(diphenylphosphino)ferrocene]dichloropalladium (II) complex with dichloromethane; DMF is N,N-dimethylformamide; DME is dimethoxyethane; HATU is 1-[Bis(dimethylamino)methylene]-1H-1,2,3-triazolo[4,5-b]pyridinium 3-oxid hexafluorophosphate; CDI is carbonyldiimidazole; EDC is 1-ethyl-3-(3-dimethylaminopropyl)carbodiimide; DBU is 1,8-diazabicyclo[5.4.0]undec-7-ene; TEA is triethylamine; PyClU is 1-(Chloro-1-pyrrolidinylmethylene)pyrrolidinium hexafluorophosphate and MW is microwave (referring to a microwave reactor).

Compounds of formula (I) wherein E is —CONR$^1$—, specifically compounds of formula (Ia-1), can be synthesized as shown in Scheme 1.

Scheme 1

[Chem. 113]

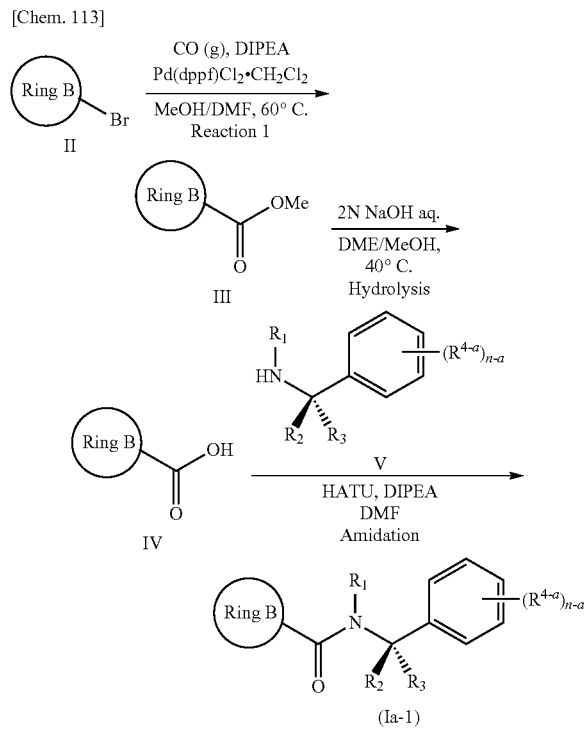

As shown in Scheme 1, reaction of a compound (II) with Pd (II) and CO (g) affords the methyl ester (III) (Reaction 1). Hydrolysis provides a compound (IV). Amidation of compound (IV) with a functionalized benzyl amine (V) provides a compound of formula (Ia-1). Reaction 1 in Scheme 1 is known, and carried out by, for example, at a temperature of 25 to 60° C. in a combination of organic solvents (e.g., dichloromethane, acetonitrile, DMF, etc.) and methanol, in the presence of a catalyst (e.g., Pd(dppf)Cl$_2$·CH$_2$Cl$_2$, etc.), under CO (g) and a base (e.g., DIPEA, TEA, etc.). Hydrolysis in Scheme 1 may be carried out, for example, in an organic solvent (e.g. methanol, tetrahydrofuran, dioxane, DME etc.) or in a combination thereof, using an alkali metal hydroxide (e.g. sodium hydroxide, potassium hydroxide or lithium hydroxide, etc.), an alkaline earth metal hydroxide (e.g. barium hydroxide or calcium hydroxide, etc.) or a carbonate (e.g. sodium carbonate or potassium carbonate, etc.) or an aqueous solution thereof or a mixture thereof at 0-40° C. Amidation in Scheme 1 is known and carried out by, for example, at a temperature of 0 to 35° C. in an organic solvent (e.g., dichloromethane, acetonitrile, DMF, etc.), in the presence of a condensing agent (e.g., HATU, EDC, PyClU, etc.), in the presence of a base (e.g., DIPEA, TEA, etc.).

Compounds of formula (I), wherein E is —NR$^1$CO—, specifically compounds of formula (Ia-2), can be synthesized as shown in Scheme 2.

Scheme 2

[Chem. 114]

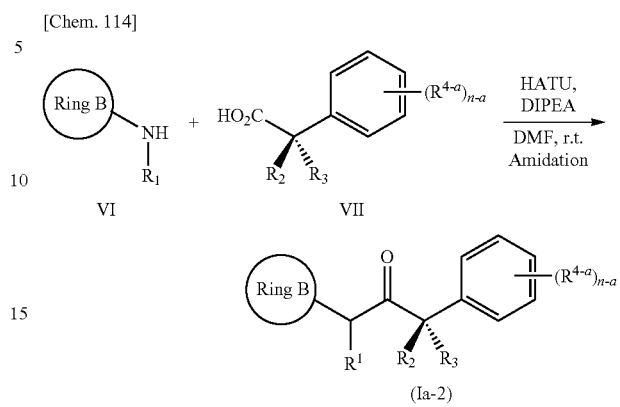

As shown in Scheme 2, amidation of a compound (VI) with a functionalized phenylacetic acid (VII) provides compound of formula (Ia-2). Amidation in Scheme 2 is known and carried out in the same way as amidation in Scheme 1.

Compounds of formula (I) wherein E is —CONR$^1$—, specifically compounds of formula (Ib-1), can be synthesized as shown in Scheme 3.

Scheme 3

[Chem. 115]

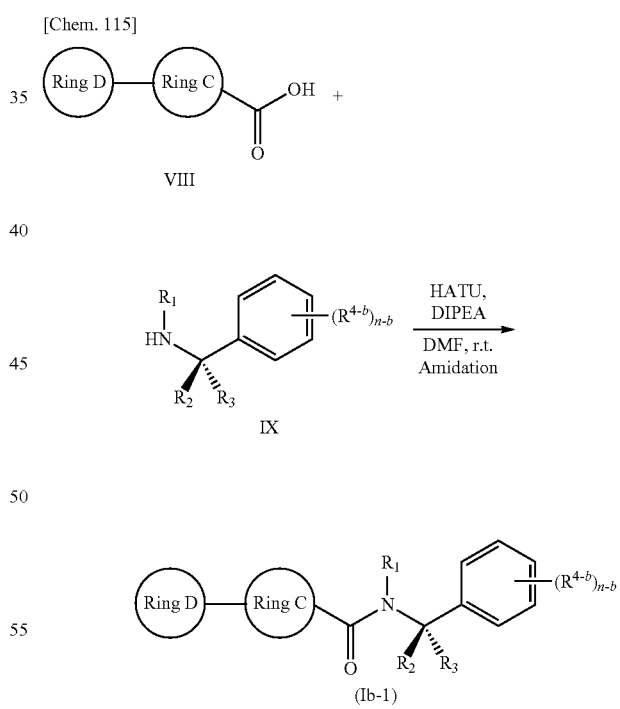

As shown in Scheme 3, amidation of a compound (VIII) with a functionalized benzyl amine (IX) provides compound of formula (Ib-1). Amidation in Scheme 3 is known and carried out in the same way as amidation in Scheme 1.

Compounds of formula (I) wherein E is —NR$^1$CO—, specifically compounds of formula (Ib-2), can be synthesized as shown in Scheme 4.

Scheme 4

[Chem. 116]

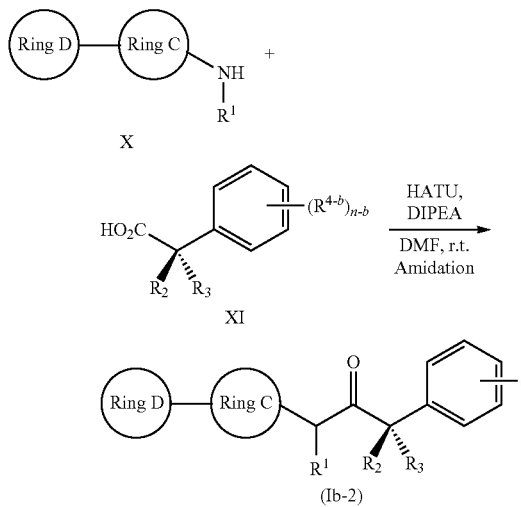

As shown in Scheme 4, amidation of a compound (X) with a functionalized phenylacetic acid (XI) provides compound of formula (Ib-2). Amidation in Scheme 4 is known and carried out in the same way as amidation in Scheme 1.

Compounds of formula (I) wherein Ring D is

[Chem. 117]

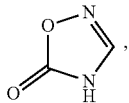

specifically compounds of formula (XV), can be synthesized as shown in Scheme 5.

Scheme 5

[Chem. 118]

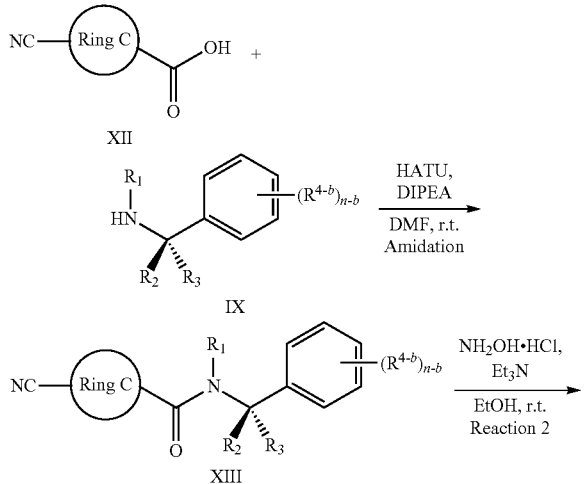

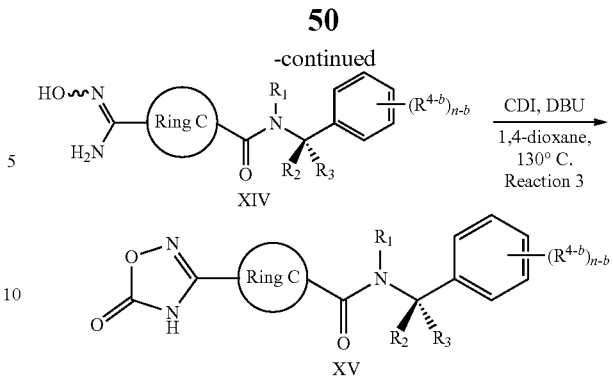

As shown in Scheme 5, amidation of a compound (XII) and (IX) affords the compound (XIII). Reaction of a compound (XIII) with hydroxyamine provides the compound (XIV) (Reaction 2). Cyclization of compound (XIV) with a CDI provides compound (XV) (Reaction 3). Amidation in Scheme 5 is known and carried out in the same way as amidation in Scheme 1. Reaction 2 in Scheme 5 is known and carried out by, for example, at a temperature of 0 to 25° C. in an organic solvent (e.g. methanol, ethanol, etc.), in the presence of hydroxylamine and a bace (e.g., DIPEA, TEA etc.). Reaction 3 in Scheme 5 is known and carried out by, for example, at a temperature of 25 to 130° C. in an organic solvent (e.g. 1,4-dioxane, etc.), in the presence of CDI, in the presence of bace (e.g., DBU etc.).

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

The compounds represented by the general formula (II), (V), (VI), (VII), (VIII), (IX), (X), (XI) or (XII) using as starting material are well-known in itself, or can be prepared easily by the known methods, for example, the methods described in Comprehensive Organic Transformations: A Guide to Functional Group Preparations, 2nd Edition (Richard C. Larock, John Wiley & Sons Inc., 1999), which may be combined.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

c. TREK-1 and TREK-2 Activator Activity

Method 1 (Thallium Flux Assay);

CHO-K1 cells stably expressing human TREK-1 or HEK293 cells stably expressing human TREK-2 are plated in 384-well plates, cultured overnight, loaded with Thallos dye the following day, treated with test compounds for 10 min, and then treated with thallium stimulus buffer to initiate thallium flux. The change in fluorescence at 25 seconds after thallium addition is normalized to baseline fluorescence (fluorescent intensity at 25 sec after $Tl^+$ addition)/(average of fluorescent intensity at pre-read). To compare the efficacy and potency of evaluated compounds, thallium flux data for each compound are normalized to that observe with the positive control activator BL-1249 ($R_{BL-1249}$(%)=100× (ΔRatio of evaluated compound−ΔRatio of 0.3% DMSO)/ (ΔRatio of 10 μM BL-1249−ΔRatio of 0.3% DMSO).

Method 2 (Patch Clamp Technique):

CHO-K1 cells stably expressing human TREK-1 or HEK293 cells stably expressing human TREK-2 are plated on glass coverslips, and voltage clamped in the whole-cell configuration of the patch clamp technique. The effects of test compounds on TREK-1 or TREK-2-mediated currents are evaluated at 0 mV and normalized to that activated by the control activator BL-1249 at a concentration of 10 μM.

In some embodiments, the disclosed compounds activate TREK-1 channel response as an increase in thallium fluorescence or increase in current measured at 0 mV in patch clamp electrophysiology assays.

The disclosed compounds may activate TREK-1 and/or TREK-2 via an activate mechanism or through an allosteric modualtion mechanism.

d. Analgesic Effect in Acetic Acid Writhing Assay

Method:

ICR mice were pretreated with vehicle (0.5 w/v % methyl cellulose, p.o.) or Example 1-25 compounds (0.3, 1, 3 mg/kg, p.o.) or Example 2 compounds (1, 10, 300 mg/kg, p.o.) or indomethacin (10 mg/kg, p.o.). Compounds were suspended in 0.5 w/v % methyl cellulose and indomethacin was dissolved in 0.7% sodium bicarbonate. All drugs were administered in a volume of 10 mL/kg. Two hours after administration of the disclosed compounds and vehicle, or one hour after administration of indomethacin, the animals were injected with acetic acid (0.7% v/v in saline, 10 mL/kg, i.p.). The number of writhes (characterized by contraction of the abdominal musculature and extension of the limbs) was then counted for 30 min. Analgesic effect was evaluated by comparing the number of writhes between the rest compounds group and the vehicle group.

3. Pharmaceutical Compositions and Formulations

The disclosed compounds may be incorporated into pharmaceutical compositions suitable for administration to a subject (such as a patient, which may be a human or non-human). The disclosed compounds may also be provided as formulations, such as spray-dried dispersion formulations.

The pharmaceutical compositions and formulations may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention (e.g., a compound of formula (I)) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 0.1 mg to about 1000 mg per person at a time, or about 1 mg to about 100 mg per person at a time, and it may be administered to patients once to several times per day.

The pharmaceutical compositions and formulations may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Compositions for oral administration can have various dosage forms. For example, solid forms include tablets, capsules, granules, and bulk powders.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I)), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT (registered trademark) coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I)), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979);

Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

a. Spray-Dried Dispersion Formulations

The disclosed compounds may be formulated as a spray-dried dispersion (SDD). An SDD is a single-phase, amorphous molecular dispersion of a drug in a polymer matrix. It is a solid solution with the compound molecularly "dissolved" in a solid matrix. SDDs are obtained by dissolving drug and a polymer in an organic solvent and then spray-drying the solution. The use of spray drying for pharmaceutical applications can result in amorphous dispersions with increased solubility of Biopharmaceutics Classification System (BCS) class II (high permeability, low solubility) and class IV (low permeability, low solubility) drugs. Formulation and process conditions are selected so that the solvent quickly evaporates from the droplets, thus allowing insufficient time for phase separation or crystallization. SDDs have demonstrated long-term stability and manufacturability. For example, shelf lives of more than 2 years have been demonstrated with SDDs. Advantages of SDDs include, but are not limited to, enhanced oral bioavailability of poorly water-soluble compounds, delivery using traditional solid dosage forms (e.g., tablets and capsules), a reproducible, controllable and scalable manufacturing process and broad applicability to structurally diverse insoluble compounds with a wide range of physical properties.

This in one embodiment, the disclosure may provide a spray-dried dispersion formulation comprising a compound of formula (I).

4. Methods of Use

The disclosed compounds, pharmaceutical compositions and formulations may be used in methods for treatment and/or prevention of disorders associated with $K_{2P}$ $K^+$ channels, specifically TREK (TWIK RElated $K^+$ channels) dysfunction for which activators of TREK-1, TREK-2 or both TREK-1 and TREK-2 would offer therapeutic benefit.

a. Treating Disorders

The disclosed compounds, pharmaceutical compositions and formulations may be used in methods for treatment and/or prevention of disorders associated with TREK channel dysfunction. The methods of treatment may comprise administering to a subject in need of such treatment a therapeutically effective amount of the compound of formula (I), or a pharmaceutical composition comprising a therapeutically effective amount of a compound of formula (I).

In some embodiments, the disclosure provides to a method for enhancing cognition in a mammal comprising the step of administering to the mammal a therapeutically effective amount of the compound of formula (I), or a pharmaceutical composition comprising a therapeutically effective amount of a compound of formula (I).

The compounds and compositions disclosed herein may be useful for treating, preventing, ameliorating, controlling or reducing the risk of a variety of disorders associated with TREK channel dysfunction. Thus, provided is a method of treating and/or preventing a disorder in a subject comprising the step of administering to the subject at least one disclosed compound or at least one disclosed pharmaceutical composition, in an amount effective to treat the disorder in the subject.

Also provided is a method for the treatment of one or more disorders associated with TREK channel dysfunction in a subject comprising the step of administering to the subject a therapeutically effective amount of the compound of formula (I), or a pharmaceutical composition comprising a therapeutically effective amount of a compound of formula (I).

In some embodiments, the disclosure provides a method for the treatment of a disorder associated with TREK channel dysfunction in a mammal, comprising the step of administering to the mammal an effective amount of at least one disclosed compound or a pharmaceutically acceptable salt thereof, or a pharmaceutical composition comprising at least one disclosed compound or pharmaceutically acceptable salt thereof.

In the treatment of conditions which require activation of a TREK channel (TREK-1, TREK-2 or dual TREK-1 and 2), an appropriate dosage level may be about 0.1 to 1000 mg per patient per day, which can be administered in single or multiple doses. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In some embodiments, the disorder can be selected from pain, nasal inflammation, atrial fibrillation, acute respiratory distress syndrome, acute lung injury, overactive bladder, cerebral ischemia, epilepsy, amyotrophic lateral sclerosis, neuronal degenerative diseases (e.g. Alzheimer's disease), sepsis, pancreatic cancer, Cushing's syndrome, autosomal dominant polycystic kidney disease, bone fracture, osteoporosis, temporal lobe epilepsy, schizophrenia, colitis, or addiction.

b. Combination Therapies

In the methods of use described herein, additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula (I). The above combinations include combinations of a compound of the present invention not only with one other active compound, but also with two or more other active compounds.

The disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefor, contemporaneously or sequentially with a disclosed compound. When a disclosed compound is used contemporaneously with one or more other drugs, a pharmaceutical composition in unit dosage form containing such drugs and the disclosed compound may be used. However, the combination therapy can also be administered on overlapping schedules. It is also envisioned that the combination of one or more active ingredients and a disclosed compound can be more efficacious than either as a single agent. Thus, when used in combination with one or more other active ingredients, the disclosed compounds and the other active ingredients can be used in lower doses than when each is used singly.

The pharmaceutical compositions and methods of the present invention can further comprise other therapeutically active compounds as noted herein which are usually applied in the treatment of the above mentioned pathological conditions.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the disclosed compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

When the present compound is used for treating and/or preventing artrial fibrillation, examples of the drugs which may be used with the present compound in combination include β-blockers, digoxin and the like.

When the present compound is used for treating and/or preventing pain, examples of the drugs which may be used with the present compound in combination include acetaminophen, a nonsteroid antiinflammatory drug, an opioid, an antidepressant, an antiepileptic agent, an N-methyl-D-aspartate antagonist, a muscle relaxant, an antiarrhythmic agent, a steroid, a bisphosphonate and the like.

The β-blockers may include, for example, alprenolol hydrochloride, bupranolol hydrochloride, bufetolol hydrochloride, oxprenolol hydrochloride, atenolol, bisoprolol fumarate, betaxolol hydrochloride, bevantolol hydrochloride, metoprolol succinate, metoprolol tartrate, acebutolol hydrochloride, celiprolol hydrochloride, nipradilol, tilisolol hydrochloride, nadorol, propranolol hydrochloride, indenolol hydrochloride, carteolol hydrochloride, pindolol, bunitrolol hydrochloride, landiolol hydrochloride, esmolol hydrochloride, arotinolol hydrochloride, carvedilol, timolol maleate and the like.

The antiarrhythmic agent may include, for example, lidocaine, mexiletine and the like.

The nonsteroid antiinflammatory drug may include, for example, sasapyrine, sodium salicylate, aspirin, aspirin formulations such as those containing aspirin-dialuminate, diflunisal, indomethacin, suprofen, ufenamate, dimethylisopropylazulene, bufexamac, felbinac, diclofenac, tolmetin sodium, Clinoril, fenbufen, nabumetone, proglumetacin, indomethacin farnesil, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, tiaprofen, oxaprozin, pranoprofen, loxoprofen sodium, alminoprofen, zaltoprofen, mefenamic acid, aluminium mefenamate, tolfenamic acid, floctafenine, ketophenylbutazone, oxyphenbutazone, piroxicam, tenoxicam, ampiroxicam, Napageln ointment, epirizole, tiaramide hydrochloride, tinoridine hydrochloride, emorfazone, sulpyrine, Migrenin, Saridon, Sedes G, Amipylo-N, Sorbon, pilin cold remedies, acetaminophen, phenacetin, dimetotiazine mesilate, meloxicam, celecoxib, rofecoxib, valdecoxib, simetride-containing formulations and non-pilin cold remedies and the like.

The opioid may include, for example, codeine, fentanyl, hydromorphone, levorphanol, meperidine, methadone, morphine, oxycodone, oxymorphone, propoxyphene and the like.

The antidepressant may include, for example, tricyclic antidepressants (e.g., imipramine hydrochloride, clomipramine hydrochloride, dosulepin hydrochloride, nortriptyline hydrochloride, lofepramine hydrochloride, trimipramine maleate, amoxapine), tetracyclic antidepressants (e.g., maprotiline hydrochloride, mianserin hydrochloride, setiptiline maleate), monoamine oxidase (MAO) inhibitors (safrazine hydrochloride), serotonin and noradrenaline reuptake inhibitors (SNRIs) (e.g., milnacipran hydrochloride, venlafaxine hydrochloride), selective serotonin reuptake inhibitors (SSRIs) (e.g., fluvoxamine maleate, paroxetine hydrochloride), serotonin reuptake inhibitors (e.g., trazodone hydrochloride) and the like.

The antiepileptic agent may include, for example, phenobarbital, Puridomin, phenytoin, ethosuximide, zonisamide, nitrazepam, clonazepam, carbamazepine, sodium valproate, acetazolamide, sulthiame, gabapentin, pregabalin and the like.

The N-methyl-D-aspartate antagonist may include, for example, ketamine hydrochloride, amantadine hydrochloride, memantine hydrochloride, dextromethorphan, methadone and the like.

The muscle relaxant may include, for example, succinylcholine, suxamethonium, vecuronium bromide, pancronium bromide, dantrolene sodium and the like.

The steroid may include, for example, as topical agents, clobetasol propionate, diflorasone diacetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclometasone propionate, triamcinolone acetonide, flumetasone pivalate, alclometasone dipropionate, clobetasone butyrate, prednisolone, beclometasone propionate, fludroxycortide and the like.

The bisphosphonate may include, for example, etidronate, pamidronate, alendronate, risedronate, zoledronate, minodronate and the like.

The present compound has low toxicity and thus can be safely used as a medicament.

c. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

5. Kits

In one aspect, the disclosure provides kits comprising at least one disclosed compound or a pharmaceutically acceptable salt thereof, and one or more of:
  (a) at least one agent known to increase TREK-1 activity;
  (b) at least one agent known to increase TREK-2 activity;
  (c) at least one agent known to treat a disorder associated with TREK dysfunction;
  (d) instructions for treating a disorder associated with TREK dysfunction; or
  (e) instructions for preventing a disorder associated with TREK dysfunction;

In some embodiments, the at least one disclosed compound and the at least one agent are co-formulated. In some embodiments, the at least one disclosed compound and the at least one agent are co-packaged. The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

That the disclosed kits can be employed in connection with disclosed methods of use.

The kits may include information, instructions, or both that use of the kit will provide treatment for medical conditions in mammals (particularly humans). The information and instructions may be in the form of words, pictures, or both, and the like. In addition or in the alternative, the kit may include the compound, a composition, or both; and information, instructions, or both, regarding methods of application of compound, or of composition, preferably with the benefit of treating or preventing medical conditions in mammals (e.g., humans).

The compounds and processes of the invention will be better understood by reference to the following examples, which are intended as an illustration of and not a limitation upon the scope of the invention.

6. Examples

All NMR spectra were recorded on a 400 MHz AMX or AVANCE III HD Bruker NMR spectrometer. $^1$H chemical shifts are reported in δ values in ppm downfield with the deuterated solvent as the internal standard. Data are reported as follows: chemical shift, multiplicity (s=singlet, bs=broad singlet, d=doublet, t=triplet, q=quartet, dd=doublet of doublets, m=multiplet, ABq=AB quartet), coupling constant, and integration or chemical shift only.

LCMS analysis conditions are as below. The MS data in Examples were measured by Acidic standard LCMS method (1-1) unless otherwise specified.

Acidic Standard LCMS Method (1-1):

Low resolution mass spectra were obtained on an Agilent 6120 or 6150 with ESI source. MS parameters were as follows: fragmentor: 70, capillary voltage: 3000 V, nebulizer pressure: 30 psig, drying gas flow: 13 L/min, drying gas temperature: 350° C. Samples were introduced via an Agilent 1290 UHPLC comprised of a G4220A binary pump, G4226A ALS, G1316C TCC, and G4212A DAD with ULD flow cell. UV absorption was generally observed at 215 nm and 254 nm with a 4 nm bandwidth. Column: Waters Acquity BEH C18, 1.0 mm×50 mm, 1.7 m. Gradient conditions: 5% to 95% $CH_3CN$ in $H_2O$ (0.1% TFA) over 1.4 min, hold at 95% $CH_3CN$ for 0.1 min, 0.5 mL/min, 55° C.
Acidic standard LCMS method (1-2):

Low resolution mass spectra were obtained on a Waters Acquity UPLC I-Class or H-Class system with photodiode array (PDA) detector, MS and ELSD via the following conditions. Column: YMC Triart C18 2.0 mm×30 mm, 1.9 m. Mobile phase A: 0.10% TFA in water (v/v). Mobile phase B: 0.10% TFA in MeCN (v/v). Gradient: 95.0% water/5.0% MeCN linear to 5% water/95% MeCN in 1.2 min, HOLD at 5% water/95% MeCN to 1.5 min. Flow: 1.0 mL/min.

Basic (High pH) LCMS Method (2):

Low resolution mass spectra were obtained on an Agilent 6120 mass spectrometer with ESI source. MS parameters were as follows: fragmentor: 100, capillary voltage: 3000 V, nebulizer pressure: 60 psig, drying gas flow: 13 L/min, drying gas temperature: 350° C. Samples were introduced via an Agilent 1200 HPLC comprised of a degasser, G1312A binary pump, G1367B HP-ALS, G1316A TCC, G1315D DAD, and a Varian 380 ELSD. UV absorption was generally observed at 215 nm and 254 nm with a 4 nm bandwidth. Column: Phenomenex Kinetex EVO C18, 2.1 mm×50 mm, 5 m. Gradient conditions: 5% to 95% $CH_3CN$ in $H_2O$ (10 mM Ammonium Bicarbonate) over 1.8 min, hold at 95% $CH_3CN$ for 0.2 min, 2 mL/min, 45° C.

Reversed-phase LCMS method (3):

Reversed-phase LCMS analysis was performed using a Waters Acquity UPLC I-Class System comprised of a binary pump, high-performance autosampler, thermostatted column compartment, C18 column, diode-array detector (DAD), ELSD and SQD2 with the following parameters. Samples were separated on a YMC Triart C18 column (1.9 m, 2.0 mm×30 mm) at 1.0 mL/min, with column and solvent temperatures maintained at 30° C. The gradient conditions were mobile phase: A) 0.1% TFA in water, B) 0.1% TFA in acetonitrile, gradient condition (Acetonitrile %); 0.00-0.10 min. 5%, 0.10-1.20 min. 5-95%, 1.20-1.40 min. 95%. The DAD was set to scan from 210 to 400 nm, and the signals used were 220 nm and 254 nm (both with a band width of 1.2 nm). The MS detector was configured with an electrospray ionization source, and the low-resolution mass spectra were acquired by scanning from 140 to 700 AMU at 2 cycles/second. The drying gas flow was set to 650 liters per hour at 350° C. and the cone gas flow was set to 50 liters per hour. The capillary needle voltage was set at 2200 V, and the cone voltage was set at 30V. Data acquisition was performed with Waters MassLynx and OpenLynx software.

Abbreviations which have been used in the descriptions of following examples are: IPA is isopropyl alcohol; AcOH is acetic acid; BOP is (benzotriazol-1-yloxy)tris(dimethylamino)phosphonium hexafluorophosphate; DBU is 1,8-diazabicyclo(5.4.0)undec-7-ene; DCM is dichloromethane; DIPEA is N,N-diisopropylethylamine; DMF is N,N-dimethylformamide; DMSO is dimethyl sulfoxide; EtOAc is ethyl acetate; NMP is N-methyl-2-pyrrolidone; $Et_2O$ is diethylether; $NaBH(OAc)_3$ is sodium triacetoxyborohydride; MW is microwave (referring to a microwave reactor); and $R_T$ is retention time; THF is tetrahydrofuran.

Example 1

N-[2-Methyl-4-(trifluoromethoxy)benzyl]-[1,2,4]triazolo[1,5-a]pyridine-6-carboxamide

[Chem. 119]

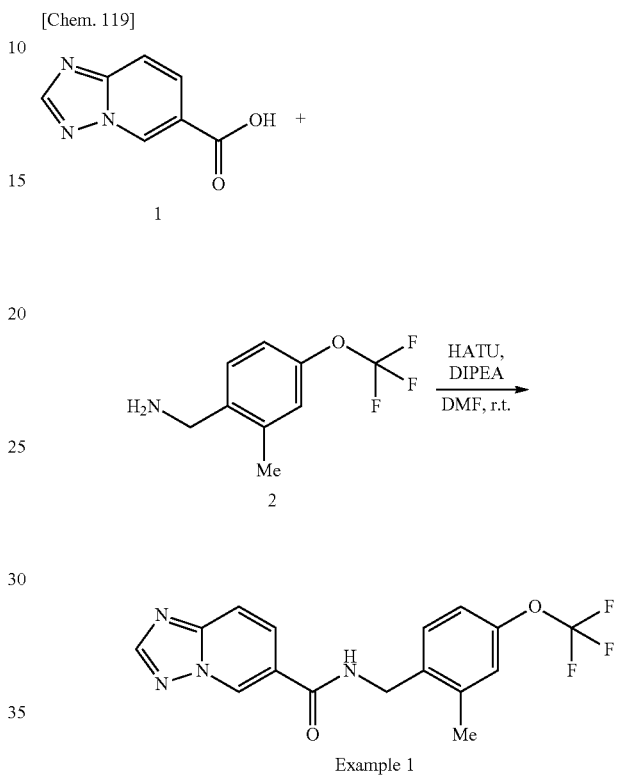

Example 1

To a screw-capped vial equipped with a magnetic stir bar were added [1,2,4]triazolo[1,5-a]pyridine-6-carboxylic acid (CAS Number: 1043903-19-0) (100 mg, 0.61 mmol), HATU (CAS Number: 148893-10-1) (232 mg, 0.61 mmol), N,N-diisopropylethylamine (213 μL, 1.22 mmol) and DMF (1 mL), followed by a solution of (2-methyl-4-(trifluoromethoxy)phenyl)methanamine (CAS Number: 771572-39-5) (125 mg, 0.61 mmol) in DMF (1 mL). This mixture was allowed to stir at room temperature for 7 hours. The reaction mixture was diluted with saturated aqueous sodium bicarbonate solution and extracted with EtOAc. The combined organic extracts were concentrated under a stream of air. The crude residue was purified by reverse-phase HPLC (eluting with 0.1% trifluoroacetic acid and acetonitrile) to afford the present invention compound (166 mg). LCMS: $R_T$=0.87 min; m/z (M+1)$^+$=351. $^1$H NMR (400 MHz, $d_6$-DMSO) δ 9.50 (s, 1H), 9.18 (t, J=5.4 Hz, 1H), 8.63 (s, 1H), 8.10 (d, J=9.3 Hz, 1H), 7.93 (d, J=9.3 Hz, 1H), 7.42 (d, J=8.5 Hz, 1H), 7.22 (s, 1H), 7.17 (d, J=8.5 Hz, 1H), 4.51 (d, J=5.4 Hz, 2H), 2.39 (s, 3H).

Example 1-1 to 1-92

The following compounds in Table 1 were prepared in same procedure as in Example 1 with the appropriate starting materials.

TABLE 1

| Example No. | Compound name (NMR data) | Retention Time(min) | MS [M + 1]+ |
|---|---|---|---|
| 1-1 | N-(2,4-dichlorobenzyl)-3-fluoro-4-[(methylsulfonyl)amino]benzamide<br>($^1$H NMR (400 MHz, d$_6$-DMSO) δ 3.12, 4.51, 7.36-7.44, 7.53, 7.64, 7.74-7.82, 9.13, 9.97.) | 1.03 | 391 |
| 1-2 | N-[4-(trifluoromethoxy)benzyl][1,2,4]triazolo[1,5-a]pyridine-6-carboxamide<br>($^1$H NMR (400 MHz, d$_6$-DMSO) δ 4.56, 7.36, 7.50, 7.94, 8.10, 8.64, 9.35, 9.50.) | 0.88 | 337 |
| 1-3 | N-[4-(trifluoromethoxy)benzyl][1,2,4]triazolo(4,3-a]pyridine-7-carboxamide<br>($^1$H NMR (400 MHz, d$_6$-DMSO) δ 4.54, 7.33-7.39, 7.49, 8.34, 8.64, 9.37, 9.42.) | 0.79 | 337 |
| 1-4 | N-(2,4-dichlorobenzyl)[1,2,4]triazolo[4,3-a]pyridine-7-carboxamide<br>($^1$H NMR (400 MHz, d$_6$-DMSO) δ 4.55, 7.37, 7.42-7.48, 7.63, 8.37, 8.65, 9.35-9.44.) | 0.77 | 321 |
| 1-5 | N-(2,4-dichlorobenzyl)[1,2,4]triazolo[1,5-a]pyridine-6-carboxamide<br>($^1$H NMR (400 MHz, d$_6$-DMSO) δ 4.57. 7.42-7.-51, 7.66, 7.95, 8.10, 8.65, 9.32, 9.53.) | 0.87 | 321 |
| 1-6 | N-(2,4-dichlorobenzyl)-1H-indazole-5-carboxamide | 0.92 | 320 |
| 1-7 | N-[4-(trifluoromethoxy)benzyl]imidazo[1,2-b]pyridazine-6-carboxamide<br>($^1$H NMR (400 MHz, d$_6$-DMSO) δ 4.54, 7.34, 7.48, 7.72, 7.96, 8.27, 8.35, 9.54.) | 0.78 | 337 |
| 1-8 | 4-(1H-1,2,4-triazol-1-ylmethyl)-N-[4-(trifluoromethoxy)benzyl]benzamide<br>($^1$H NMR (400 MHz, d$_6$-DMSO) δ 4.49, 5.49, 7.30-7.45, 7.88, 8.01, 8.70, 9.10.) | 0.87 | 377 |
| 1-9 | N-(4-bromo-2-chlorobenzyl)-4-[(methylsulfonyl)amino]benzamide<br>($^1$H NMR (400 MHz, d$_6$-DMSO) δ 3.08, 4.48, 7.24-7.31, 7.55, 7.74, 7.89, 8.99, 10.16.) | 1.01 | 419 |
| 1-10 | 4-[(methylsulfonyl)amino]-N-{[5-(trifluoromethyl)-2-pyridinyl]methyl}benzamide<br>($^1$H NMR (400 MHz, d$_6$-DMSO) δ 3.08, 4.65, 7.25-7.30, 7.54, 7.91, 8.18, 8.90-8.94, 9.15, 10.16.) | 0.73 | 374 |
| 1-11 | N-(2,4-dichlorobenzyl)-2-fluoro-4-[(methylsulfonyl)amino]benzamide<br>($^1$H NMR (400 MHz, d$_6$-DMSO) δ 3.13, 4.49, 7.06, 7.09, 7.38, 7.44, 7.63, 7.69, 8.73-8.78, 10.39.) | 0.98 | 391 |
| 1-12 | 2-fluoro-N-[2-fluoro-4-(trifluoromethoxy)benzyl]isonicotinamide<br>($^1$H NMR (400 MHz, d$_6$-DMSO) δ 4.54, 7.25, 7.41, 7.51-7.61, 7.77, 8.42, 9.44.) | 1.04 | 333 |
| 1-13 | 6-fluoro-N-[2-fluoro-4-(trifluoromethoxy)benzyl]nicotinamide<br>($^1$H NMR (400 MHz, d$_6$-DMSO) δ 4.54, 7.24, 7.33, 7.41, 7.55, 8.43, 8.75, 9.28.) | 1.02 | 333 |
| 1-14 | N-[2-fluoro-4-(trifluoromethoxy)benzyl]isonicotinamide<br>($^1$H NMR (400 MHz, d$_6$-DMSO) δ 4.54, 7.24, 7.41, 7.53, 7.79, 8.75, 9.36.) | 0.80 | 315 |
| 1-15 | N-[2-fluoro-4-(trifluoromethyl)benzyl]-4-[(methylsulfonyl)amino]benzamide<br>($^1$H NMR (400 MHz, d$_6$-DMSO) δ 3.08, 4.56, 7.26, 7.54-7.60, 7.68, 7.88, 9.05, 10.16.) | 0.89 | 391 |
| 1-16 | N-[2-chloro-4-(trifluoromethyl)benzyl]-4-[(methylsulfonyl)amino]benzamide<br>($^1$H NMR (400 MHz, d$_6$-DMSO) δ 3.09, 4.59, 7.28, 7.55, 7.72, 7.87-7.93, 9.08, 10.17.) | 0.95 | 407 |
| 1-17 | 4-[(methylsulfonyl)amino]-N-[4-(trifluoromethoxy)benzyl]benzamide<br>($^1$H NMR (400 MHz, d$_6$-DMSO) δ 3.07, 4.49, 7.24-7.28, 7.31-7.35, 7.41-7.45, 7.85-7.90, 9.01, 10.14.) | 0.98 | 389 |
| 1-18 | N-(2,4-dichlorobenzyl)-4-(methylsulfonyl)benzamide<br>($^1$H NMR (400 MHz, d$_6$-DMSO) δ 3.28, 4.55, 7.39-7.45, 7.65, 8.04-8.08, 8.11-8.16, 9.34.) | 0.94 | 358 |
| 1-19 | N-[2-methoxy-4-(trifluoromethyl)benzyl]-4-[(methylsulfonyl)amino]benzamide<br>($^1$H NMR (400 MHz, d$_6$-DMSO) δ 3.08, 3.93, 4.47, 7.25-7.37, 7.90, 8.90, 10.15.) | 0.98 | 403 |
| 1-20 | N-[4-(difluoromethoxy)benzyl]-4-[(methylsulfonyl)amino]benzamide<br>($^1$H NMR (400 MHz, d$_6$-DMSO) δ 3.07, 4.45, 7.01-7.39, 7.87, 8.97, 10.13.) | 0.86 | 371 |

TABLE 1-continued

| Example No. | Compound name (NMR data) | Retention Time(min) | MS [M + 1]+ |
|---|---|---|---|
| 1-21 | N-[4-(trifluoromethoxy)benzyl][1,2,4]triazolo[1,5-a]pyridine-7-carboxamide<br>($^1$H NMR (400 MHz, d$_6$-DMSO) δ 4.56, 7.35, 7.49, 7.61, 8.39, 8.64, 9.08, 9.48.) | 0.87 | 337 |
| 1-22 | 4-[(methylsulfonyl)amino]-N-[2-methyl-4-(trifluoromethyl)benzyl]benzamide<br>($^1$H NMR (400 MHz, d$_6$-DMSO) δ 2.42, 3.08, 4.50, 7.27, 7.42, 7.50-7.56, 7.87-7.92, 8.95, 10.14.) | 0.99 | 387 |
| 1-23 | N-[3-fluoro-4-trifluoromethozy)benzyl][1,2,4]triazolo[1,5-a]pyridine-6-carboxamide<br>($^1$H NMR (400 MHz, d$_6$-DMSO) δ 4.54, 7.30-7.32, 7.48-7.56, 7.91-7.94, 8.07-8.09, 8.62, 9.34, 9.50.) | 0.89 | 355 |
| 1-24 | N-{[5-(trifluoromethyl)-2-pyridinyl]methyl}[1,2,4]triazolo[1,5-a]pyridine-6-carboxamide | 0.69 | 322 |
| 1-25 | N-[2-fluoro-4-(trifluoromethoxy)benzyl][1,2,4]triazolo[1,5-a]pyridine-6-carboxamide;<br>($^1$H NMR (400 MHz, d$_6$-DMSO) δ 9.48 (dd, J = 1.7, 0.9 Hz, 1H), 9.30 (d, J = 5.6 Hz, 1H), 8.62 (s, 1H), 8.07 (dd, J = 9.3, 1.7 Hz, 1H), 7.92 (dd, J = 9.3, 0.9 Hz, 1H), 7.55-7.60 (m, 1H), 7.38-7.41 (m, 1H), 7.22-7.24 (m, 1H), 4.55 (d, J = 5.6 Hz, 1H)) | 0.93 | 355 |
| 1-26 | N-[2-methoxy-4-(trifluoromethoxy)benzyl][1,2,4]triazolo[1,5-a]pyridine-6-carboxamide<br>($^1$H NMR (400 MHz, d$_6$-DMSO) δ 3.88, 4.48, 6.93, 7.03, 7.38, 7.94, 8.11, 8.64, 9.16, 9.51.) | 0.93 | 367 |
| 1-27 | N-[2-chloro-4-(trifluoromethyl)benzyl][1,2,4]triazolo[1,5-a]pyridine-5-carboxamide<br>($^1$H NMR (400 MHz, d$_6$-DMSO) δ 4.66, 7.67-7.75, 7.91, 7.96, 8.11, 8.66, 9.42, 9.55.) | 0.94 | 355 |
| 1-28 | N-4-bromo-2-chlorobenzyl)[1,2,4]triazolo[1,5-a]pyridine-6-carboxamide<br>($^1$H NMR (400 MHz, d$_6$-DMSO) δ 4.55, 7.42, 7.56, 7.77, 7.95, 8.10, 8.65, 9.32, 9.52.) | 0.93 | 365 |
| 1-29 | N-[2-fluoro-4-(trifluoromethoxy)benzyl][1,2,4]triazolo[4,3-a]pyridine-7-carboxamide | 0.85 | 355 |
| 1-30 | N-[2-methoxy-4-(trifluoromethoxy)benzyl][1,2,4]triazolo[4,3-a]pyridine-7-carboxamide;<br>($^1$H NMR (400 MHz, d$_6$-DMSO) δ 9.36 (s, 1H), 9.21 (t, J = 5.7 Hz, 1H), 8.63 (d, J = 7.2 Hz, 1H), 8.35 (s, 1H), 7.37 (d, J = 7.2 Hz, 1H), 7.33 (d, J = 8.3 Hz, 1H), 7.00 (s, 1H), 6.91 (d, J = 8.3 Hz, 1H), 4.44 (d, J = 5.7 Hz, 2H), 3.86 (s, 3H)) | 0.86 | 367 |
| 1-31 | N-[2-chloro-4-(trifluoromethyl)benzyl][1,2,4]triazolo[4,3-a]pyridine-7-carboxamide<br>($^1$H NMR (400 MHz, d$_6$-DMSO) δ 4.64, 7.38, 7.66, 7.74, 7.91, 8.40, 8.66, 9.39, 9.49.) | 0.88 | 355 |
| 1-32 | N-(4-bromo-2-chlorobenzyl)[1,2,4]triazolo[4,3-a]pyridine-7-carboxamide<br>($^1$H NMR (400 MHz, d$_6$-DMSO) δ 4.59, 7.41-7.47, 7.62, 7.82, 8.43, 8.70, 9.41-9.47.) | 0.87 | 367 |
| 1-33 | N-(4-(trifluoromethoxy)benzyl]thieno[2,3-b]pyridine-2-carboxamide<br>($^1$H NMR (400 MHz, d$_6$-DMSO) δ 4.54, 7.33-7.39, 7.45-7.53, 8.13, 8.39, 8.67, 9.48.) | 1.04 | 353 |
| 1-34 | N-[4-(trifluoromethoxy)benzyl]-2-(trifluoromethyl)-5-pyrimidinecarboxamide<br>($^1$H NMR (400 MHz, d$_6$-DMSO) δ 4.58, 7.36, 7.51, 9.44, 9.60.) | 1.09 | 366 |
| 1-35 | 2,6-difluoro-N-[4-(trifluoromethoxy)benzyl]isonicotinamide<br>($^1$H NMR (400 MHz, d$_6$-DMSO) δ 4.53, 7.35, 7.47, 7.58, 9.51.) | 1.09 | 333 |
| 1-36 | N-[4-(trifluoromethoxy)benzyl]-6-quinoxalinecarboxamide | 0.96 | 348 |
| 1-37 | N-[2,4-bis(difluoromethoxy)benzyl]-4-[(methylsulfonyl)amino]benzamide<br>($^1$H NMR (400 MHz, d$_6$-DMSO) δ 3.07, 4.45, 7.05-7.08, 7.12-7.50, 7.88, 8.91, 10.14.) | 0.92 | 437 |

TABLE 1-continued

| Example No. | Compound name (NMR data) | Retention Time(min) | MS [M + 1]+ |
|---|---|---|---|
| 1-38 | N-[2,4-bis(difluoromethoxy)benzyl]-6-fluoronicotinamide ($^1$H NMR (400 MHz, d$_6$-DMSO) δ 4.49, 7.05-7.50, 8.42, 8.74, 9.19.) | 0.95 | 363 |
| 1-39 | 6-fluoro-N-[2-methoxy-4-(trifluoromethoxy)benzyl]nicotinamide ($^1$H NMR (400 MHz, d$_6$-DMSO) δ 3.87, 4.45, 6.92, 7.02, 7.33, 8.44, 8.76, 9.12.) | 0.99 | 345 |
| 1-40 | N-[2-methoxy-4-(trifluoromethoxy)benzyl]-4-[(methylsulfonyl)amino]benzamide ($^1$H NMR (400 MHz, d$_6$-DMSO) δ 3.07, 3.87, 4.42, 6.91, 7.00, 7.23-7.29, 7.89, 8.83, 10.13.) | 0.95 | 419 |
| 1-41 | N-[2-methoxy-4-(trifluoromethoxy)benzyl]imidazo[1,2-a]pyridine-6-carboxamide ($^1$H NMR (400 MHz, d$_6$-DMSO) δ 3.88, 4.46, 6.93, 7.02, 7.33, 7.61-7.72, 8.08, 8.99, 9.17.) | 0.81 | 366 |
| 1-42 | 6-oxo-N-[4-(trifluoromethoxy)benzyl]-1,6-dihydro-4-pyridazinecarboxamide ($^1$H NMR (400 MHz, d$_6$-DMSO) δ 4.48, 7.26, 7.32-7.39, 7.46, 8.14, 9.40, 13.32.) | 0.84 | 314 |
| 1-43 | N-[4-(trifluoromethoxy)benzyl]pyrazolo[1,5-a]pyrimidine-2-carboxamide ($^1$H NMR (400 MHz, d$_6$-DMSO) δ 4.57, 7.15, 7.25, 7.40, 7.52, 8.71, 9.19, 9.29.) | 0.92 | 337 |
| 1-44 | N-[4-(trifluoromethoxy)benzyl][1,2,4]triazolo[1,5-a]pyrimidine-2-carboxamide ($^1$H NMR (400 MHz, d$_6$-DMSO) δ 4.52, 7.34, 7.45-7.52, 9.00, 9.48, 9.65.) | 0.85 | 338 |
| 1-45 | N-[2-methyl-4-(trifluoromethoxy)benzyl][1,2,4]triazolo[4,3-a]pyridine-7-carboxamide | 0.89 | 351 |
| 1-46 | N-[2-methyl-4-(trifluoromethoxy)benzyl]pyrazolo[1,5-a]pyrimidine-2-carboxamide ($^1$H NMR (400 MHz, d$_6$-DMSO) δ 2.44, 4.54, 7.16-7.28, 7.42, 8.71, 9.14-9.22.) | 0.97 | 351 |
| 1-47 | N-(2-chloro-4-(trifluoromethyl)benzyl]pyrazolo[1,5-a]pyrimidine-2-carboxamide ($^1$H NMR (400 MHz, d$_6$-DMSO) δ 4.63, 7.13, 7.22, 7.56, 7.73, 7.90, 8.67, 9.17, 9.30.) | 0.96 | 355 |
| 1-48 | 6-fluoro-N-[2-methyl-4-(trifluoromethoxy)benzyl]nicotinamide ($^1$H NMR (400 MHz, d$_6$-DMSO) δ 2.38, 4.48, 7.17, 7.22, 7.33, 7.38, 8.44, 8.75, 9.16.) | 1.01 | 329 |
| 1-49 | N-[2-chloro-4-(trifluoromethyl)benzyl]-6-fluoronicotinamide | 1.00 | 333 |
| 1-50 | N-[2-fluoro-4-(trifluoromethoxy)benzyl]pyrazolo[1,5-a]pyrimidine-2-carboxamide ($^1$H NMR (400 MHz, d$_6$-DMSO) δ 4.55, 7.10, 7.18-7.22, 7.24, 7.39, 7.51, 8.66, 9.14, 9.19.) | 0.93 | 355 |
| 1-51 | N-[2-methoxy-4-(trifluoromethoxy)benzyl]pyrazolo[1,5-a]pyrimidine-2-carboxamide ($^1$H NMR (400 MHz, d$_6$-DMSO) δ 3.88, 4.46, 6.92, 7.01, 7.11, 7.18-7.23, 7.27, 8.66, 8.97, 9.15.) | 0.94 | 367 |
| 1-52 | N-[3-fluoro-4-(trifluoromethoxy)benzyl]pyrazolo[1,5-a]pyrimidine-2-carboxamide ($^1$H NMR (400 MHz, d$_6$-DMSO) δ 4.52, 7.10, 7.20, 7.29, 7.45, 7.54, 8.66, 9.14, 9.28.) | 0.92 | 355 |
| 1-53 | 2,6-difluoro-N-[2-fluoro-4-(trifluoromethoxy)benzyl]isonicotinamide ($^1$H NMR (400 MHz, d$_6$-DMSO) δ 4.55, 7.23-7.27, 7.42, 7.54-7.60, 9.49. | 1.08 | 351 |
| 1-54 | 2,6-difluoro-N-[2-methoxy-4-(trifluoromethoxy)benzyl]isonicotinamide- ($^1$H NMR (400 MHz, d$_6$-DMSO) δ 3.87, 4.45, 6.92, 7.03, 7.33, 7.58, 9.32.) | 1.09 | 363 |
| 1-55 | 2-6-difluoro-N-[2-methyl-4-(trifluorothoxy)benzyl]isonicotinamide | 1.11 | 347 |
| 1-56 | N-[2-fluoro-4-(trifluoromethoxy)benzyl]-6-oxo-1,6-dihydro-4-pyridazinecarboxamide | 0.84 | 332 |
| 1-57 | N-[2-methoxy-4-(trifluoromethoxy)benzyl]-6-oxo-1,6-dihydro-4-pyridazinecarboxamide ($^1$H NMR (400 MHz, d$_6$-DMSO) δ 3.86, 4.40, 6.92, 7.02, 7.27, 7.33, 8.14, 9.23, 13.32.) | 0.86 | 344 |
| 1-58 | N-[2-methyl-4-(trifluoromethoxy)benzyl]-6-oxo-1,6-dihydro-4-pyridazinecarboxamide | 0.88 | 328 |
| 1-59 | N-[2-fluoro-4-(trifluoromethoxy)benzyl][1,2,4]triazolo[1,5-a]pyrimadine-2-carboxamide | 0.85 | 356 |

TABLE 1-continued

| Example No. | Compound name (NMR data) | Retention Time(min) | MS [M + 1]+ |
|---|---|---|---|
| 1-60 | N-[2-methoxy-4-(trifluoromethoxy)benzyl][1,2,4]triazolo[1,5-a]pyrimidine-2-carboxamide<br>($^1$H NMR (400 MHz, d$_6$-DMSO) δ 3.88, 4.47, 6.92, 7.02, 7.27, 7.50, 9.01, 9.39, 9.49.) | 0.86 | 368 |
| 1-61 | N-[2-methyl-4-(trifluoromethoxy)benzyl][1,2,4]triazolo[1,5-a]pyrimidine-2-carboxamide | 0.88 | 352 |
| 1-62 | N-[2-fluoro-4-(trifluoromethoxy)benzyl]-4-[(methylsulfonyl)amino]benzamide<br>($^1$H NMR (400 MHz, d$_6$-DMSO) δ 3.03, 4.50, 7.20-7.25, 7.39, 7.48, 7.85, 8.95, 10.15.) | 0.94 | 407 |
| 1-63 | N-[2,4-bis(trifluoromethyl)benzyl][1,2,4]triazolo[1,5-a]pyridine-6-carboxamide<br>($^1$H NMR (400 MHz, d$_6$-DMSO) δ 4.77, 7.89, 7.97, 8.05-8.13, 8.67, 9.50, 9.56.) | 0.95 | 389 |
| 1-64 | N-[2,4-bis(trifluoromethyl)benzyl][1,2,4]triazolo[4,3-a]pyridine-7-carboxamide<br>($^1$H NMR (400 MHz, d$_6$-DMSO) δ 4.76, 7.38, 7.86, 8.06, 8.09, 8.41, 8.67, 9.39, 9.56.) | 0.91 | 389 |
| 1-65 | 4-[(methylsulfonyl)amino]-N-[2-methyl-4-(trifluoromethoxy)benzyl]benzamide<br>($^1$H NMR (400 MHz, d$_6$-DMSO) δ 2.37, 3.04, 4.44, 7.14-7.25, 7.33, 7.86, 8.85, 10.14.) | 0.96 | 403 |
| 1-66 | N-(4-bromo-2-chlorobenzyl)pyrazolo[1,5-a]pyrimidine-2-carboxamide | 0.94 | 367 |
| 1-67 | N-(4-bromo-2-chlorobenzyl)-6-oxo-1,6-dihydro-4-pyridazinecarboxamide | 0.80 | 344 |
| 1-68 | 6-fluoro-N-[4-(trifluoromethoxy)benzyl]nicotinamide | 0.91 | 315 |
| 1-69 | N-(4-bromo-2-chlorobenzyl)-3-fluoro-4-[(methylsulfonyl)amino]benzamide<br>($^1$H NMR (400 MHz, d$_6$-DMSO) δ 3.12, 4.49, 7.31, 7.51-7.57, 7.73-7.82, 9.12, 9.96.) | 0.94 | 435 |
| 1-70 | 4-amino-N-[2,4-bis(trifluoromethyl)benzyl]-3-fluorobenzamide<br>($^1$H NMR (400 MHz, d$_6$-DMSO) δ 4.67, 5.80, 6.79, 7.52-7.62, 7.73, 8.02, 8.07, 8.90.) | 0.98 | 381 |
| 1-71 | N-[4-(trifluoromethoxy)benzyl]-1H-indazole-5-carboxamide<br>($^1$H NMR (400 MHz, d$_6$-DMSO) δ 4.53, 7.34, 7.47, 7.59, 7.90, 8.22, 8.39, 9.10, 13.29.) | 0.92 | 336 |
| 1-72 | N-[4-(trifluoromethoxy)benzyl]-1H-benzimidazole-5-carboxamide<br>($^1$H NMR (400 MHz, d$_6$-DMSO) δ 4.52, 7.34, 7.47, 7.55-7.85, 8.05-8.40, 9.09, 12.62-12.79.) | 0.77 | 336 |
| 1-73 | N-(2,4-dichlorobenzyl)-1H-benzimidazole-5-carboxamide<br>($^1$H NMR (400 MHz, d$_6$-DMSO) δ 4.54, 7.36-7.47, 7.64, 7.69, 7.80, 8.15-8.39, 9.07, 12.60-12.82.) | 0.77 | 320 |
| 1-74 | N-[[2-methyl-4-(trifluoromethoxy)phenyl]methyl]-1H-benzotriazole-5-carboxamide;<br>($^1$H NMR (400 MHz, d$_6$-DMSO) δ 2.40, 4.51, 7.15-7.23, 7.40, 7.81-8.67, 9.10-9.22, 15.90-16.06.) | 0.87*$^1$ | 351 |
| 1-75 | N-[[2-fluoro-4-(trifluoromethoxy)phenyl]methyl]-1H-benzotriazole-5-carboxamido;<br>($^1$H NMR (400 MHz, d$_6$-DMSO) δ 4.57, 7.25, 7.40, 7.56, 7.87-8.08, 8.41-8.68, 9.26.) | 0.87*$^1$ | 355 |
| 1-76 | N-[(4-bromo-2-chlorophenyl)methyl]-1H-benzotriazole-5-carboxamide;<br>($^1$H NMR (400 MHz, d$_6$-DMSO) δ 4.55, 7.37, 7.56, 7.76, 7.99, 8.43-8.66, 9.26, 15.87-16.14.) | 0.88*$^1$ | 365 |
| 1-77 | 1-methyl-N-[[2-methyl-4-(trifluoromethoxy)phenyl]methyl]benzotriazole-5-carboxamide | 0.95*$^1$ | 365 |
| 1-78 | N-[[2-fluoro-4-trifluoromethoxy)phenyl]methyl]-1-methylbenzotriazole-5-carboxamide | 0.93*$^1$ | 369 |
| 1-79 | N-[(4-bromo-2-chlorophenyl)methyl]-1-methylbenzotriazole-5-carboxamide | 0.93*$^1$ | 379 |
| 1-80 | N-[[2-methyl-4-(trifluoromethoxy)phenyl]methyl]pyrazolo[1,5-a]pyrimidine-6-carboxamide;<br>($^1$H NMR (400 MHz, d$_6$-DMSO) δ 2.40, 4.51, 6.84, 7.17, 7.23, 7.45, 8.38, 8.95, 9.16, 9.60.) | 0.93*$^1$ | 351 |
| 1-81 | N-[[2-fluoro-4-(trifluoromethoxy)phenyl]methyl]pyrazolo[1,5-a]pyrimidine-6-carboxamide;<br>($^1$H NMR (400 MHz, d$_6$-DMSO) δ 4.57, 6.84, 7.26, 7.42, 7.61, 8.39, 8.94, 9.29, 9.59.) | 0.90*$^1$ | 355 |

TABLE 1-continued

| Example No. | Compound name (NMR data) | Retention Time(min) | MS [M + 1]+ |
|---|---|---|---|
| 1-82 | N-[(4-bromo-2-chlorophenyl)methyl]pyrazolo[1,5-a]pyrimidine-6-carboxamide; (¹H NMR (400 MHz, d₆-DMSO) δ 4.55, 6.85, 7.45, 7.56, 7.76, 8.39, 8.95, 9.29, 9.61.) | 0.91*¹ | 365 |
| 1-83 | 6-amino-N-[[2-methyl-4-(trifluoromethoxy)phenyl]methyl]pyridine-3-carboxamide | 0.75*¹ | 326 |
| 1-84 | N-[[2-methyl-4-(trifluoromethoxy)phenyl]methyl]-1,2,3-benzothiadiazole-5-carboxamide; (¹H NMR (400 MHz, d₆-DMSO) δ 2.42, 4.55, 7.19, 7.22-7.24, 7.44, 8.30, 8.52, 9.25 9.35.) | 1.03*¹ | 368 |
| 1-85 | N-[[2-fluoro-4-(trifluoromethoxy)phenyl]methyl]-1,2,3-benzothiadiazole-5-carboxamide | 1.01*¹ | 372 |
| 1-86 | N-[(4-bromo-2-chlorophenyl)methyl]-1,2,3-benzothiadiazole-5-carboxamide | 1.02*¹ | 382 |
| 1-87 | N-[[2-methyl-4-(trifluoromethoxy)phenyl]methyl]imidazo[1,2-a]pyridine-7-carboxamide | 0.75*¹ | 350 |
| 1-88 | N-[[2-bromo-4-(trifluoromethoxy)phenyl]methyl]-[1,2,4]triazolo[1,5-a]pyridine-6-carboxamide; (¹H NMR (400 MHz, d₆-DMSO) δ 4.57, 7.44, 7.58, 7.75, 7.95, 8.11, 8.65, 9.35, 9.54.) | 0.88*¹ | 415 |
| 1-89 | N-[[2-cyano-4-(trifluoromethoxy)phenyl]methyl]-[1,2,4]triazolo[1,5-a]pyridine-6-carboxamide (¹H NMR (400 MHz, d₆-DMSO) δ 4.71, 7.75, 7.95, 8.04, 8.09, 8.65, 9.47-9.53.) | 0.80*¹ | 362 |
| 1-90 | N-[[4-(difluoromethoxy)-2-fluorophenyl]methyl]-[1,2,4]triazolo[1,5-a]pyridine-6-carboxamide (¹H NMR (400 MHz, d₆-DMSO) δ 4.53, 7.01-7.07, 7.10-7.54, 7.93, 8.09, 8.64, 9.28, 9.49.) | 0.77*¹ | 337 |
| 1-91 | N-[2-bromo-4-(trifluoromethoxy)benzyl][1,2,4]triazolo[4,3-a]pyridine-7-carboxamide (¹H NMR (400 MHz, d₆-DMSO) δ 4.78, 7.18-7.22 7.28-7.31, 7.41, 7.50, 7.56, 8.19, 8.28, 8.89.) | 0.74 | 415 |
| 1-92 | N-[[2-chloro-4-(difluoromethoxy)phenyl]methyl]-[1,2,4]triazolo[1,5-a]pyridine-6-carboxamide; (¹H NMR (400 MHz, d₆-DMSO) δ 4.57, 7.11-7.55, 7.94, 8.20, 8.65, 9.30, 9.52.) | 0.82*¹ | 353 |

*¹the data were measured by Acidic standard LCMS method (1-2) as described above.

Example 2

N-[2-Methyl-4-(trifluoromethoxy)benzyl]-6-(1H-1,2,4-triazol-1-yl)nicotinamide

[Chem. 120]

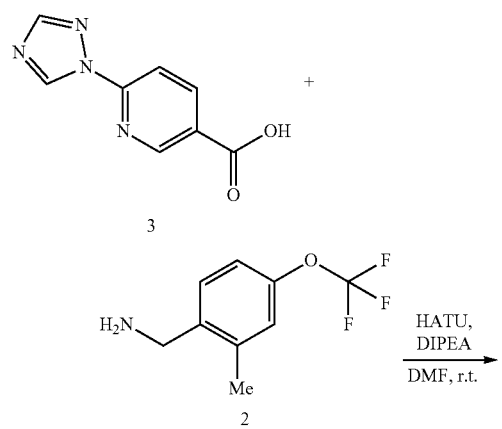

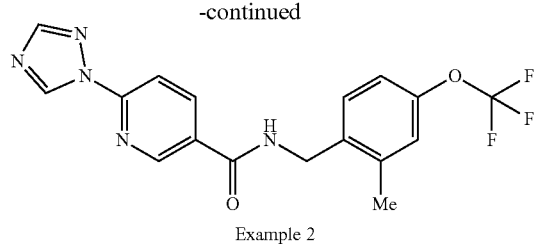

Example 2

To a screw-capped vial equipped with a magnetic stir bar were added 6-(1H-1,2,4-triazol-1-yl)nicotinic acid (CAS Number: 281232-20-0) (100 mg, 0.53 mmol), HATU (CAS Number: 148893-10-1) (199 mg, 0.53 mmol), N,N-diisopropylethylamine (182 μL, 1.05 mmol) and DMF (1 mL), followed by a solution of (2-methyl-4-(trifluoromethoxy)phenyl)methanamine (CAS Number: 771572-39-5) (107 mg, 0.53 mmol) in DMF (1 mL). This mixture was allowed to stir at room temperature for 7 hours. The reaction mixture was diluted with saturated aqueous sodium bicarbonate solution and extracted with EtOAc. The combined organic extracts were concentrated under a stream of air. The crude residue was purified by reverse-phase HPLC (eluting with 0.1% trifluoroacetic acid and acetonitrile) to afford the present invention compound (57 mg). LCMS: R$_T$=0.93 min*¹; m/z (M+1)⁺=378. ¹H NMR (400 MHz, d₆-DMSO) δ

9.47 (s, 1H), 9.23-9.26 (m, 1H), 9.01 (s, 1H), 8.52 (d, J=8.5 Hz, 1H), 8.37 (s, 1H), 7.99 (d, J=8.5 Hz, 1H), 7.40 (d, J=8.7 Hz, 1H), 7.22 (s, 1H), 7.17 (d, J=8.7 Hz, 1H), 4.51 (d, J=5.4 Hz, 2H), 2.39 (s, 3H). *[1]: the data were measured by Acidic standard LCMS method (1-2) as described above.

Example 2-1 to 2-51

The following compounds in Table 2 were prepared in same procedure as in Example 2 with the appropriate starting materials.

TABLE 2

| Example No. | Compound name (NMR data) | Retention Time (min) | MS [M + 1]+ |
| --- | --- | --- | --- |
| 2-1 | N-[2-methoxy-4-(trifluoromethoxy)benzyl]-4-(1H-1,2,4-triazol-1-yl)benzamide ($^1$H NMR (400 MHz, d$_6$-DMSO) δ 3.88, 4.46, 6.93, 7.02, 7.30, 7.99-8.03, 8.08-8.12, 8.30, 9.05, 9.42.) | 0.93 | 393 |
| 2-2 | N-[4-(pentafluoro-λ$^6$-sulfanyl)benzyl]-4-(1H-1,2,4-triazol-1-yl)benzamide ($^1$H NMR (400 MHz, d$_6$-DMSO) δ 4.58, 7.56, 7.89, 8.00-8.12, 8.30, 9.29, 9.42.) | 0.93 | 405 |
| 2-3 | N-[3-fluoro-4-(trifluoromethoxy)benzyl]-4-(1H-1,2,4-triazol-1-yl)benzamide | 0.94 | 381 |
| 2-4 | 4-(1H-pyrazol-1-yl)-N-[4-(trifluoromethoxy)benzyl]benzamide ($^1$H NMR (400 MHz, d$_6$-DMSO) δ 4.52, 6.60, 7.35, 7.46, 7.81, 7.95-8.05, 8.62, 9.16.) | 1.03 | 362 |
| 2-5 | 4-(1H-imidazol-1-yl)-N-[4-(trifluoromethoxy)benzyl]benzamide ($^1$H NMR (400 MHz, d$_6$-DMSO) δ 4.53, 7.15, 7.35, 7.46, 7.79-7.88, 8.04, 8.40, 9.19.) | 0.80 | 362 |
| 2-6 | 4-(1,3-oxazol-5-yl)-N-[4-(trifluoromethoxy)benzyl]benzamide | 0.99 | 363 |
| 2-7 | 4-(2-pyridinyl)-N-[4-(trifluoromethoxy)benzyl]benzamide ($^1$H NMR (400 MHz, d$_6$-DMSO) δ 4.53, 7.32-7.49, 7.93, 8.00-8.08, 8.21, 8.71, 9.19.) | 0.91 | 373 |
| 2-8 | 4-(1H-tetrazol-1-yl)-N)-[4-(trifluoromethoxy)benzyl]benzamide ($^1$H NMR (400 MHz, d$_6$-DMSO) δ 4.54, 7.35, 7.48, 8.05-8.09, 8.13-8.18, 9.30, 10.20.) | 0.93 | 364 |
| 2-9 | 4-(1,3-thiazol-2-yl)-N-+4-(trifluoromethoxy)benzyl+benzamide | 1.05 | 379 |
| 2-10 | 4-(1H-imidazol-5-yl)-N-[4-(trifluoromethoxy)benzyl]benzamide ($^1$H NMR (400 MHz, d$_6$-DMSO) δ 4.51, 7.31-7.36, 7.45, 7.75, 7.8-7.95, 9.04, 12.27.) | 0.84 | 362 |
| 2-11 | 4-(3-pyridinyl)-N-[4-(trifluoromethoxy)benzyl]benzamide ($^1$H NMR (400 MHz, d$_6$-DMSO) δ 4.54, 7.35, 7.44-7.55, 7.85-7.90, 8.01-8.06, 8.14-8.18, 8.62, 8.97, 9.20.) | 0.87 | 373 |
| 2-12 | 4-(1,3,4-oxadiazol-2-yl)-N-[4-(trifluoromethoxy)benzyl]benzamide ($^1$H NMR (400 MHz, d$_6$-DMSO) δ 4.53, 7.34, 7.47, 8.09-8.16, 9.32, 9.41.) | 1.00 | 364 |
| 2-13 | 4-(1H-1,2,4-triazol-3-yl)-N-[4-(trifluoromethoxy)benzyl]benzamide ($^1$H NMR (400 MHz, d$_6$-DMSO) δ 4.52, 7.35, 7.47, 7.95-8.04, 8.09-8.14, 8.43-8.65, 9.18, 14.11-14.51.) | 89 | 363 |
| 2-14 | 4-(4-pyridinyl)-N-[4-(trifluoromethoxy)benzyl]benzamide ($^1$H NMR (400 MHz, d$_6$-DMSO) δ 4.54, 7.35, 7.46, 7.79, 7.92-7.97, 8.02-8.07, 8.68, 9.23.) | 0.86 | 373 |
| 2-15 | N-[4-(difluoromethoxy)benzyl]-4-(1H-1,2,4-triazol-1-yl) benzamide ($^1$H NMR (400 MHz, d$_6$-DMSO) δ 4.49, 7.02-7.42, 7.98-8.03, 8.05-8.11, 8.30, 9.19, 9.41.) | 0.80 | 345 |
| 2-16 | N-[2-fluoro-4-(trifluoromethoxy)benzyl]-4-(1H-1,2,4-triazol-1-yl)benzamide ($^1$H NMR (400 MHz, d$_6$-DMSO) δ 4.55, 7.25, 7.41, 7.53, 7.99-8.11, 8.30, 9.20, 9.42.) | 0.92 | 381 |
| 2-17 | N-[3-chloro-4-(trifluoromethoxy)benzyl]-4-(1H-1,2,4-triazol-1-yl)benzamide ($^1$H NMR (400 MHz, d$_6$-DMSO) δ 4.53, 7.45, 7.56, 7.65, 7.99-8.12, 8.30, 9.25, 9.42.) | 0.96 | 397 |
| 2-18 | 4-(1H-1,2,4-triazol-1-yl)-N-{4-[(trifluoromethyl)thio]benzyl}benzamide ($^1$H NMR (400 MHz, d$_6$-DMSO) δ 4.57, 7.50, 7.71, 7.99-8.04, 8.07-8.12, 8.30, 9.27, 9.42.) | 0.95 | 379 |
| 2-19 | N-(2,4-dichlorobenzyl)-4-(1H-1,2,4-triazol-1-yl)benzamide ($^1$H NMR (400 MHz, d$_6$-DMSO) δ 4.54, 7.39-7.46, 7.65, 8.00-8.05, 8.07-8.13, 8.30, 9.20, 9.43.) | 0.94 | 347 |

TABLE 2-continued

| Example No. | Compound name (NMR data) | Retention Time (min) | MS [M + 1]+ |
|---|---|---|---|
| 2-20 | N-[4-(1,1-difluoroethyl)benzyl]-4-(1H-1,2,4-triazol-1-yl) benzamide<br>($^1$H NMR (400 MHz, d$_6$-DMSO) δ 1.95, 4.55, 7.45, 7.54, 7.98-8.03, 8.06-8.12, 8.30, 9.23, 9.42.) | 0.87 | 343 |
| 2-21 | 4-(5-pyrimidinyl)-N-[4-(trifluoromethoxy)benzyl]benzamide<br>($^1$H NMR (400 MHz, d$_6$-DMSO) δ 4.54, 7.35, 7.47, 7.97, 8.06, 9.21-9.25.) | 0.98 | 374 |
| 2-22 | N-[3-fluoro-4-(trifluoromethoxy)benzyl]-4-(1H-1,2,4-triazol-3-yl)benzamide<br>($^1$H NMR (400 MHz, d$_6$-DMSO) δ 4.51, 7.26-7.29, 7.42-7.46, 7.51-7.55, 7.94-8.00, 8.09-8.11, 8.50, 9.18.) | 0.90 | 381 |
| 2-23 | 4-(1H-1,2,4-triazol-3-yl)-N-{[5-trifluoromethyl)-2-pyridinyl]methyl}benzamide | 0.72 | 348 |
| 2-24 | N-[2-fluoro-4-(trifluoromethoxy)benzyl]-4-(1H-1,2,4-triazol-5-yl)benzamide<br>($^1$H NMR (400 MHz, d$_6$-DMSO) δ 4.54, 7.25, 7.40, 7.53, 7.96-8.02, 8.09-8.13, 8.46, 9.16.) | 0.93 | 381 |
| 2-25 | N-[2-methoxy-4-(trifluoromethoxy)benzyl]-4-(1H-1,2,4-triazol-3-yl)benzamide | 0.94 | 393 |
| 2-26 | N-[2-chloro-4-(trifluoromethyl)benzyl]-4-(1H-1,2,4-triazol-3-yl)benzamide | 0.95 | 381 |
| 2-27 | N-[2-methoxy-4-(trifluoromethoxy)benzyl]-4-(3-pyridinyl)benzamide<br>($^1$H NMR (400 MHz, d$_6$-DMSO) δ 3.89, 4.46, 6.91-6.96, 7.02, 7.29, 7.58-7.64, 7.87-7.93, 8.03-8.08, 8.26, 8.66, 8.99-9.06.) | 0.90 | 403 |
| 2-28 | N-[2-chloro-4-(trifluoromethyl)benzyl]-4-(3-pyridinyl)benzamide<br>($^1$H NMR (400 MHz, d$_6$-DMSO) δ 4.64, 7.60, 7.71-7.77, 7.90-7.97, 8.09, 8.42, 8.73, 9.10, 9.30.) | 0.90 | 391 |
| 2-29 | N-[2-methoxy-4-(trifluoromethoxy)benzyl]-2,2'-bipyridine-5-carboxamide<br>($^1$H NMR (400 MHz, d$_6$-DMSO) δδ 3.89, 4.48, 6.94, 7.03, 7.35, 7.52, 8.00, 8.39-8.51, 8.74, 9.15-9.21.) | 0.91 | 404 |
| 2-30 | N-[2-methoxy-4-(trifluoromethoxy)benzyl]-6-(1H-1,2,4-triazol-1-yl)nicotinamide<br>($^1$H NMR (400 MHz, d$_6$-DMSO) δ 3.88, 4.48, 6.93, 7.03, 7.35, 7.99, 8.38, 8.52, 9.02, 9.22, 9.48.) | 0.95 | 394 |
| 2-31 | 4-(1H-imidazol-2-yl)-N-[2-methoxy-4-(trifluoromethoxy)benzyl]benzamide<br>($^1$H NMR (400 MHz, d$_6$-DMSO) δ 3.88, 4.45, 6.93, 7.01, 7.08, 7.27-7.34, 7.96-8.05, 8.94, 12.67.) | 0.84 | 392 |
| 2-32 | 4-(2-pyridinyl)-N-[4-(trifluoromethoxy)benzyl]-1,3-thiazole-2-carboxamide | 1.01 | 380 |
| 2-33 | N-(1-benzofuran-2-ylmethyl)-4-(1H-1,2,4-triazol-1-yl) benzamide<br>($^1$H NMR (400 MHz, d$_6$-DMSO) δ 4.68, 6.79, 7.20-7.30, 7.55, 7.60, 7.99-8.04, 8.08-8.13, 8.30, 9.26, 9.42.) | 0.87 | 319 |
| 2-34 | N-[2-methyl-4-(trifluoromethoxy)benzyl]-4-(1H-1,2,4-triazol-5-yl)benzamide<br>($^1$H NMR (400 MHz, d$_6$-DMSO) δ 2.35-2.52, 4.54, 7.21-7.28, 7.43, 8.01-8.19, 8.54-8.80, 9.11, 14.17-14.43) | 0.96 | 377 |
| 2-35 | 4-(1H-imidazol-2-yl)-N-{[5-(trifluoromethyl)-2-pyridinyl]methyl}benzamide | 0.63 | 347 |
| 2-36 | N-[2-fluoro-4-(trifluoromethoxy)benzyl]-4-(1H-imidazol-2-yl)benzamide<br>($^1$H NMR (400 MHz, d$_6$-DMSO) δ 4.53, 7.07-7.32, 7.40, 7.53, 7.95-8.05, 9.10, 12.68.) | 0.81 | 380 |
| 2-37 | 4-(1H-pyrazol-1-yl)-N-{[5-(trifluoromethyl)-2-pyridinyl]methyl}benzamide<br>($^1$H NMR (400 MHz, d$_6$-DMSO) δ 4.68, 6.61, 7.59, 7.82, 7.97-8.09, 8.19, 8.64, 8.93, 9.31.) | 0.88 | 347 |
| 2-38 | N-[2-methyl-4-(trifluoromethoxy)benzyl]-4-(1H-pyrazol-1-yl)benzamide<br>($^1$H NMR (400 MHz, d$_6$-DMSO) δ 2.39, 4.48, 6.60, 7.15-7.23, 7.37, 7.81, 7.95-8.06, 8.62, 9.03.) | 1.09 | 376 |
| 2-39 | N-[2-chloro-4-(trifluoromethyl)benzyl]-4-(1H-pyrazol-1-yl)benzamide | 1.08 | 380 |
| 2-40 | N-[2-fluoro-4-(trifluoromethoxy)benzyl]-4-(1H-pyrazol-1-yl) benzamide<br>($^1$H NMR (400 MHz, d$_6$-DMSO) δ 4.59, 6.66, 7.31, 7.46, 7.58, 7.87, 8.01-8.11, 8.68, 9.20.) | 1.04 | 380 |

TABLE 2-continued

| Example No. | Compound name (NMR data) | Retention Time (min) | MS [M + 1]+ |
|---|---|---|---|
| 2-41 | N-[2-methoxy-4-(trifluoromethoxy)benzyl]-4-(1H-pyrazol-1-yl)benzamide<br>($^1$H NMR (400 MHz, d$_6$-DMSO) δ 3.94, 4.51, 6.66, 6.99, 7.07, 7.35, 7.87, 8.01-8.12, 8.68, 9.04.) | 1.05 | 392 |
| 2-42 | N-[2-fluoro-4-(trifluoromethoxy)benzyl]-4-(2-pyridinyl)benzamide<br>($^1$H NMR (400 MHz, d$_6$-DMSO) δ 4.60, 7.31, 7.44-7.49, 7.59, 7.99, 8.05-8.14, 8.27, 8.77, 9.23.) | 0.87 | 391 |
| 2-43 | N-[2-methoxy-4-(trifluoromethoxy)benzyl]-4-(2-pyridinyl)benzamide<br>($^1$H NMR (400 MHz, d$_6$-DMSO) δ 3.94, 4.52, 6.99, 7.07, 7.36, 7.47, 7.99, 8.06-8.14, 8.27, 8.77, 9.08.) | 0.88 | 403 |
| 2-44 | N-[2-chloro-4-(trifluoromethyl)benzyl]-4-(2-pyridinyl)benzamide<br>($^1$H NMR (400 MHz, d$_6$-DMSO) δ 4.69, 7.48, 7.66, 7.80, 7.93-8.03, 8.09-8.15, 8.29, 8.78, 9.33.) | 0.89 | 391 |
| 2-45 | N-(4-bromo-2-chlorobenzyl)-4-(1H-pyrazol-1-yl)benzamide<br>($^1$H NMR (400 MHz, d$_6$-DMSO) δ 4.52, 6.61, 7.34, 7.56, 7.75, 7.81, 7.96 - 8.07, 8.63, 9.14.) | 1.04 | 392 |
| 2-46 | N-(4-bromo-2-chlorobenzyl)-4-(2-pyrimidinyl)benzamide | 1.03 | 402 |
| 2-47 | 4-(2-pyrimidinyl)-N-[4-(trifluoromethoxy)benzyl]benzamide<br>($^1$H NMR (400 MHz, d$_6$-DMSO) δ 4.53, 7.35, 7.45-7.53, 8.03-8.08, 8.46-8.51, 8.96, 9.25.) | 0.99 | 374 |
| 2-48 | N-[2-fluoro-4-(trifluoromethoxy)benzyl]-6-(1H-1,2,4-triazol-1-yl)nicotinamide<br>($^1$H NMR (400 MHz, d$_6$-DMSO) δ 4.57, 7.25, 7.42, 7.57, 7.99, 8.37, 8.51, 9.01, 9.38, 9.48.) | 0.93 | 382 |
| 2-49 | N-(4-bromo-2-chlorobenzyl)-4-(1H-1,2,4-triazol-5-yl)benzamide;<br>($^1$H NMR (400 MHz, d$_6$-DMSO) δ 9.14 (br s, 1H), 8.67 (s, 1H), 8.00-8.13 (m, 4H), 7.75 (s, 1H), 7.56 (d, J = 8.0 Hz, 1H), 7.33 (d, J = 8.0 Hz, 1H), 4.51 (d, J = 5.8 Hz, 2H)) | 0.94 | 393 |
| 2-50 | 4-(3-bromo-1,2,4-triazol-1-yl)-N-[[2-methyl-4-(trifluoromethoxy)phenyl]methyl]benzamide;<br>($^1$H NMR (400 MHz, d$_6$-DMSO) δ 2.39, 4.49, 7.15-7.23, 7.37, 7.94-7.99, 8.04-8.15, 9.10, 9.43.) | 1.03*[1] | 455 |
| 2-51 | 6-(3-methyl-1,2,4-triazol-1-yl)-N-[[2-methyl-4-(trifluoromethoxy)phenyl]methyl]pyridine-3-carboxamide;<br>($^1$H NMR (400 MHz, d$_6$-DMSO) δ 2.39, 2.41, 4.51, 7.16-7.23, 7.40, 7.91, 8.49, 8.98, 9.23, 9.32.) | 0.94*[1] | 392 |

*[1] the data were measured by Acidic standard LCMS method (1-2) as described above.

Example 3

4-Cyano-N-[2-methoxy-4-(trifluoromethoxy)benzyl]benzamide

[Chem. 121]

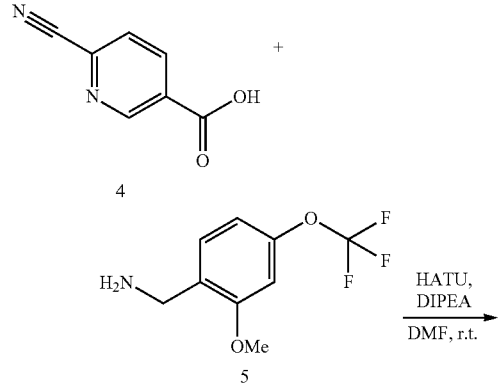

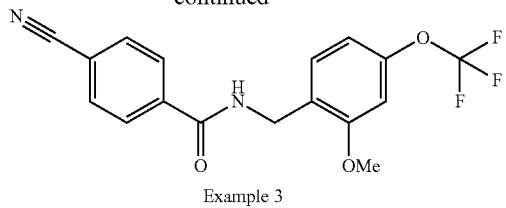

Example 3

To a screw-capped vial equipped with a magnetic stir bar were added 4-cyanobenzoic acid (CAS Number: 619-65-8) (100 mg, 0.68 mmol), HATU (CAS Number: 148893-10-1) (260 mg, 0.68 mmol), N,N-diisopropylethylamine (236 μL, 1.36 mmol) and DMF (0.5 mL), followed a solution of (2-methoxy-4-(trifluoromethoxy)phenyl)methanamine (CAS Number: 771582-58-2) (150 mg, 0.68 mmol) in DMF (0.5 mL). This mixture was allowed to stir at room temperature overnight. The reaction mixture was diluted with saturated aqueous sodium bicarbonate solution and extracted with EtOAc. The combined organic extracts were concentrated under a stream of air. The crude residue was purified by silica gel column chromatography (0-80% EtOAc in hexanes gradient) to afford the present invention compound (163 mg). LCMS: $R_T$=1.04 min; m/z (M+1)⁺=351. ¹H NMR (400 MHz, d₆-DMSO) δ 9.13-9.16 (m, 1H), 8.02-8.04 (m, 2H), 7.95-7.97 (m, 2H), 7.28 (d, J=8.4 Hz, 1H), 6.99 (s, 1H), 6.90 (d, J=8.4 Hz, 1H), 4.42-4.43 (m, 2H), 3.85 (s, 3H).

The overall synthesis scheme for the preparation of 8-methyl-[1,2,4]triazolo[1,5-a]pyridine-6-carboxylic acid (Intermediate 1) is shown below.

[Chem. 122]

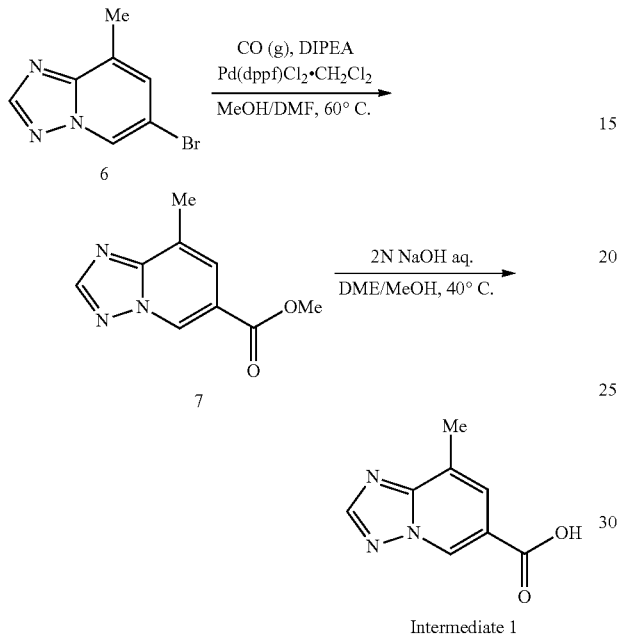

Intermediate 1

Methyl 8-methyl-[1,2,4]triazolo[1,5-a]pyridine-6-carboxylate (7)

A mixture of 6-bromo-8-methyl-[1,2,4]triazolo[1,5-a]pyridine (CAS Number: 899429-04-0) (200 mg, 0.94 mmol), N,N-diisopropylethylamine (492 μL, 2.82 mmol) and 1,1'-bis(diphenylphosphino)ferrocene palladium(II)dichloride dichloromethane complex (CAS Number: 95464-05-4) (77 mg, 0.09 mmol) in DMF/MeOH (2 mL/2 mL) was stirred at 60° C. for 3 hours under an atmosphere of carbon monoxide. The reaction mixture was filtered through a small pad of Celite (registered trademark) (eluting with EtOAc). The organic phase was washed with water and concentrated to afford the title compound (113 mg). LCMS: $R_T$=0.62 min; m/z (M+1)⁺=192.

8-Methyl-[1,2,4]triazolo[1,5-a]pyridine-6-carboxylic acid (Intermediate 1)

To a solution of methyl 8-methyl-[1,2,4]triazolo[1,5-a]pyridine-6-carboxylate (7) (113 mg, 0.59 mmol) in methanol/dimethoxyethane (1 mL/1 mL) was added 2 mol/L NaOH solution in water (1 mL). The reaction mixture was allowed to stir at 40° C. for 2 hours. After cooling to ambient temperature, the reaction mixture was neutralized with 1 mol/L HCl solution in water (2 mL) and extracted with EtOAc. The combined organic extracts were washed with water and concentrated to provide the title compound (73 mg). LCMS: $R_T$=0.43 min; m/z (M+1)⁺=178. ¹H NMR (400 MHz, d₆-DMSO) δ 9.49 (s, 1H), 8.61 (s, 1H), 7.88 (s, 1H), 2.59 (s, 3H).

The overall synthesis scheme for the preparation of 4-(methylsulfonyl)-3,4-dihydro-2H-benzo[b][1,4]oxazine-7-carboxylic acid (Intermediate 2) is shown below.

[Chem. 123]

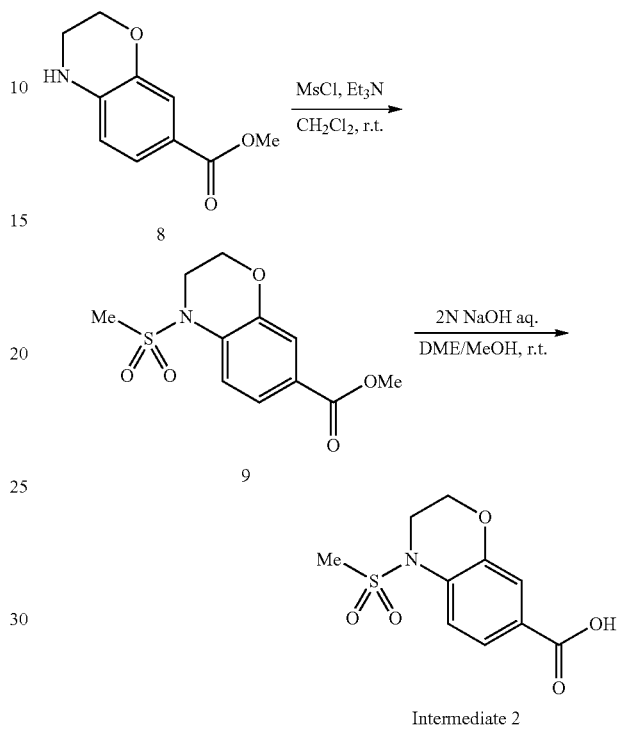

Intermediate 2

Methyl 4-(methylsulfonyl)-3,4-dihydro-2H-benzo[b][1,4]oxazine-7-carboxylate (9)

To a round-bottom flask equipped with a magnetic stir bar were added methyl 3,4-dihydro-2H-benzo[b][1,4]oxazine-7-carboxylate (CAS Number: 142166-01-6) (200 mg, 1.04 mmol), dichloromethane (2 mL), trimethylamine (120 μL, 1.55 mmol), methanesulfonyl chloride (435 μL, 3.12 mmol). This mixture was allowed to stir at room temperature overnight. The reaction mixture was diluted with water and extracted with EtOAc. The combined organic extracts were washed with water and concentrated to provide the title compound (229 mg). LCMS: $R_T$=0.74 min; m/z (M+1)⁺=272.

4-(Methylsulfonyl)-3,4-dihydro-2H-benzo[b][1,4] oxazine-7-carboxylic acid (Intermediate 2)

To a round-bottom flask equipped with a magnetic stir bar was added a solution of methyl 4-(methylsulfonyl)-3,4-dihydro-2H-benzo[b][1,4]oxazine-7-carboxylate (9) (229 mg, 0.84 mmol) in methanol/dimethoxyethane (2 mL/3 mL), followed by 2 mol/L NaOH solution in water (2.5 mL). This mixture was allowed to stir at room temperature overnight. The reaction mixture was neutralized with 2 mol/L HCl solution in water (2.5 mL) and extracted with EtOAc. The combined organic extracts were concentrated under reduced pressure to provide the title compound (218 mg). LCMS: $R_T$=0.61 min; m/z (M+1)⁺=258. ¹H NMR (400 MHz, $d_6$-DMSO) δ 7.69 (d, J=8.6 Hz, 1H), 7.48 (d, J=8.6 Hz, 1H), 7.40 (s, 1H), 4.27-4.30 (m, 2H), 3.83-3.85 (m, 2H), 3.18 (s, 3H).

Example 3-1 to 3-10

The following compounds in Table 3 were prepared in an analogous manner with the appropriate starting materials, such as intermediate 1, 2 or a compound prepared in same procedure as in scheme for intermediate 1 or 2.

TABLE 3

| Example No. | Compound name | Retention Time (min) | MS [M + 1]+ |
|---|---|---|---|
| 3-1 | 8-methyl-N-[2-methyl-4-(trifluoromethoxy)benzyl][1,2,4]triazolo[1,5-a]pyridine-6-carboxamide ($^1$H NMR (400 MHz, $d_6$-DMSO) δ 2.39, 2.59, 4.50, 7.17, 7.22-7.23, 7.42, 7.93, 8.59, 9.14, 9.35.) | 0.98 | 365 |
| 3-2 | N-(4-bromo-2-chlorobenzyl)-8-methyl[1,2,4]triazolo[1,5-a]pyridine-6-carboxamide ($^1$H NMR (400 MHz, $d_6$-DMSO) δ 2.59, 4.54, 7.41, 7.56, 7.76, 7.92, 8.60, 9.25, 9.36.) | 0.96 | 379 |
| 3-3 | N-[3-fluoro-4-(trifluoromethoxy)benzyl]-3-methyl[1,2,4]triazolo[4,3-a]pyridine-7-carboxamide ($^1$H NMR (400 MHz, $d_6$-DMSO) δ 2.74, 4.55, 7.31, 7.40, 7.50, 7.56, 8.32, 8.51, 9.44.) | 0.80 | 369 |
| 3-4 | 2-methyl-N-[2-methyl-4-(trifluoromethoxy)benzyl][1,2,4]triazolo[1,5-a]pyridine-6-carboxamide ($^1$H NMR (400 MHz, $d_6$-DMSO) δ 2.39, 2.46-2.55, 4.50, 7.15-7.24, 7.41, 7.78, 8.06, 9.16, 9.37.) | 0.90 | 365 |
| 3-5 | 3-methyl-N-[2-methyl-4-(trifluoromethoxy)benzyl][1,2,4]triazolo[4,3-a]pyridine-7-carboxamide ($^1$H NMR (400 MHz, $d_6$-DMSO) δ 2.39, 2.73, 4.50, 7.18, 7.22-7.25, 7.37, 7.40, 8.30, 8.45, 9.26.) | 0.88 | 365 |
| 3-6 | N-[2-methoxy-4-(trifluoromethoxy)benzyl]-4-(methylsulfonyl)-3,4-dihydro-2H-1,4-benzoxazine-7-carboxamide ($^1$H NMR (400 MHz, $d_6$-DMSO) δ 3.19, 3.84-3.88, 4.28-4.34, 4.41, 6.91, 7.00, 7.23, 7.49, 7.67, 8.87.) | 0.98 | 461 |
| 3-7 | 4-(methylsulfonyl)-N-[2-methyl-4-(trifluoromethoxy)benzyl]-3 4-dihydro-2H-1,4-benzoxazine-7-carboxamide ($^1$H NMR (400 MHz, $d_6$-DMSO) δ 2.36, 3.18, 3.82-3.88, 4.27-4.35, 4.44, 7.14-7.21, 7.32, 7.47-7.50, 7.67, 8.92) | 1.00 | 445 |
| 3-8 | N-[2-methoxy-4-(trifluoromethoxy)benzyl]-1-(methylsulfonyl)-5-indolinecarboxamide ($^1$H NMR (400 MHz, $d_6$-DMSO) δ 3.06, 3.16, 3.87, 4.00, 4.41, 6.91, 7.00, 7.24, 7.30, 7.80, 7.83, 8.81.) | 0.98 | 445 |
| 3-9 | 1-(methylsulfonyl)-N-[2-methyl-4-(trifluoromethoxy)benzyl]-5-indolinecarboxamide ($^1$H NMR (400 MHz, $d_6$-DMSO) δ 2.36, 3.06, 3.12-3.32, 4.00, 4.44, 7.13-7.22, 7.30, 7.32, 7.78-7.82, 8.86.) | 1.00 | 429 |
| 3-10 | N-(4-bromo-2-chlorobenzyl)-4-(methylsulfonyl)-3,4-dihydro-2H-1,4-benzoxazine-7-carboxamide ($^1$H NMR (400 MHz, $d_6$-DMSO) δ 3.19, 3.82-3.89, 4.28-4.35, 4.47, 7.27, 7.47-7.56, 7.68, 7.74, 9.03.) | 1.00 | 459 |

The overall synthesis scheme for the preparation of N-(2-methoxy-4-(trifluoromethoxy)benzyl)-4-(5-oxo-4,5-dihydro-1,2,4-oxadiazol-3-yl)benzamide (Example 4) is shown below.

[Chem. 124]

Example 3 →(NH$_2$OH·HCl, Et$_3$N / EtOH, r.t.)→

-continued

Example 4

4-(N'-Hydroxycarbamimidoyl)-N-(2-methoxy-4-(trifluoromethoxy)benzyl)benzamide (10)

To a screw-capped vial equipped with a magnetic stir bar were added 4-cyano-N-(2-methoxy-4-(trifluoromethoxy)benzyl)benzamide (Example 3) (50 mg, 0.14 mmol), trimethylamine (30 µL, 0.21 mmol), hydroxylamine hydrochloride (15 mg, 0.21 mmol) and ethanol (1 mL). This mixture was allowed to stir at room temperature for 5 hours. The reaction mixture was diluted with water and extracted with EtOAc. The combined organic extracts were concentrated under a stream of air to provide the title compound (62 mg). LCMS: $R_T$=0.89 min; m/z (M+1)$^+$=384.

Example 4

N-[2-Methoxy-4-(trifluoromethoxy)benzyl]-4-(5-oxo-4,5-dihydro-1,2,4-oxadiazol-3-yl)benzamide To a round-bottom flask equipped with a magnetic stir bar were added 4-(N-hydroxycarbamimidoyl)-N-(2-methoxy-4-(trifluoromethoxy)benzyl)benzamide (10) (20 mg, 0.05 mmol), 1,1'-carbonyldiimidazole (13 mg, 0.08 mmol), 1,8-diazabicyclo[5.4.0]undec-7-ene (12 µL, 0.08 mmol) and 1,4-dioxane (1 mL). This mixture was allowed to stir at 130° C. for 2.5 hours. After cooling to ambient temperature, the reaction mixture was diluted with 1 mol/L HCl solution in water and extracted with EtOAc. The combined organic extracts were concentrated under a stream of air. The crude residue was purified by reverse-phase HPLC (eluting with 0.1% trifluoroacetic acid and acetonitrile) to afford the present invention compound (12 mg). LCMS: $R_T$=0.98 min; m/z (M+1)$^+$=410. $^1$H NMR (400 MHz, d$_6$-DMSO) δ 9.05-9.08 (m, 1H), 8.04-8.06 (m, 2H), 7.89-7.91 (m, 2H), 7.28 (d, J=8.3 Hz, 1H), 6.99 (s, 1H), 6.91 (d, J=8.3 Hz, 1H), 4.42-4.44 (m, 2H), 3.85 (s, 3H).

Example 5

N-[2-Methoxy-4-(trifluoromethoxy)benzyl]-4-(1H-tetrazol-5-yl)benzamide

[Chem. 125]

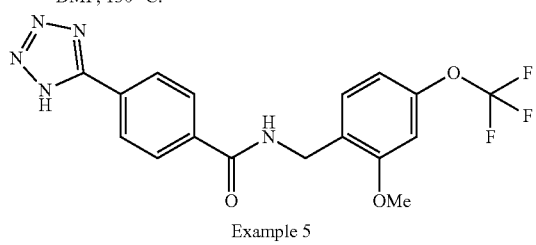

Example 5

To a round-bottom flask equipped with a magnetic stir bar were added 4-cyano-N-(2-methoxy-4-(trifluoromethoxy)benzyl)benzamide (Example 3) (20 mg, 0.06 mmol), ammonium chloride (5 mg, 0.09 mmol), sodium azide (6 mg, 0.09 mmol) and DMF (1 mL). This mixture was allowed to stir at 130° C. for 7 hours. After cooling to ambient temperature, the reaction mixture was diluted with water and extracted with EtOAc. The combined organic extracts were concentrated under a stream of air. The crude residue was purified by reverse-phase HPLC (eluting with 0.1% trifluoroacetic acid and acetonitrile) to afford the present invention compound (4 mg). LCMS: $R_T$=0.94 min; m/z (M+1)$^+$=394. $^1$H NMR (400 MHz, d$_6$-DMSO) δ 9.04-9.07 (m, 1H), 8.08-8.14 (m, 4H), 7.29 (d, J=8.4 Hz, 1H), 7.00 (s, 1H), 6.91 (d, J=8.4 Hz, 1H), 4.44-4.45 (m, 2H), 3.86 (s, 3H).

Example 6

2-[2-Fluoro-4-(trifluoromethoxy)phenyl]-N-([1,2,4]triazolo[1,5-a]pyridin-6-yl)acetamide

[Chem. 126]

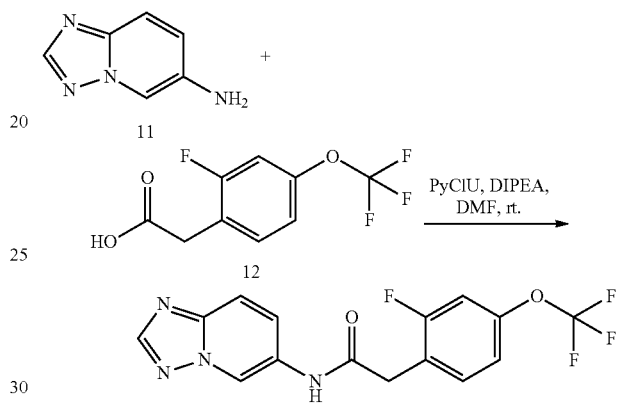

Example 6

To a round-bottom flask equipped with a magnetic stir bar were added [1,2,4]triazolo[1,5-a]pyridine-6-amine (CAS Number: 31052-94-5) (10 mg, 0.07 mmol), 2-fluoro-4-(trifluoromethoxy)phenylacetic acid (CAS Number: 1240256-95-4) (17 mg, 0.07 mmol), chlorodipyrrolidinocarbenium hexafluorophosphate (CAS Number: 135540-11-3) (23 mg, 0.07 mmol), N,N-diisopropylethylamine (48 µL, 0.28 mmol) and DMF (1 mL). This mixture was allowed to stir at room temperature for 2 hours. The reaction mixture was diluted with EtOAc and washed with saturated sodium chloride solution in water. The aqueous layer was then extracted with EtOAc. The combined organic extracts were dried over sodium sulfate and the filtrate was concentrated under a stream of air. The crude residue was purified by reverse-phase HPLC (eluting with 0.1% trifluoroacetic acid and acetonitrile) to afford the present invention compound (4 mg). LCMS: $R_T$=0.86 min; m/z (M+1)$^+$=355.

Example 6-1 and 6-2

The following compounds in Table 4 were prepared in same procedure as in Example 6 with the appropriate starting materials.

TABLE 4

| Example No. | Compound name | Retention Time (min) | MS [M + 1]+ |
|---|---|---|---|
| 6-1 | N-{4-[(methylsulfonyl)amino]phenyl}-2-[4-(trifluoromethoxy)phenyl]acetamide ($^1$H NMR(400 MHz, d$_6$-DMSO) δ 2.92, 3.68, 7.12-7.17, 7.33, 7.45, 7.55, 9.55, 10.21.) | 0.94 | 389 |

TABLE 4-continued

| Example No. | Compound name | Retention Time (min) | MS [M + 1]+ |
|---|---|---|---|
| 6-2 | 2-[4-(difluoromethoxy)phenyl]-N-{4-[(methylsulfonyl)amino]phenyl}acetamide | 0.82*[2] | 371 |

*[2]The dara was measured by Reversed-phase LCMS method (3).

The overall synthesis scheme for the preparation of (S)-4-((3-methylmorpholino)methyl)benzoic acid (Intermediate 3) is shown below.

[Chem. 127]

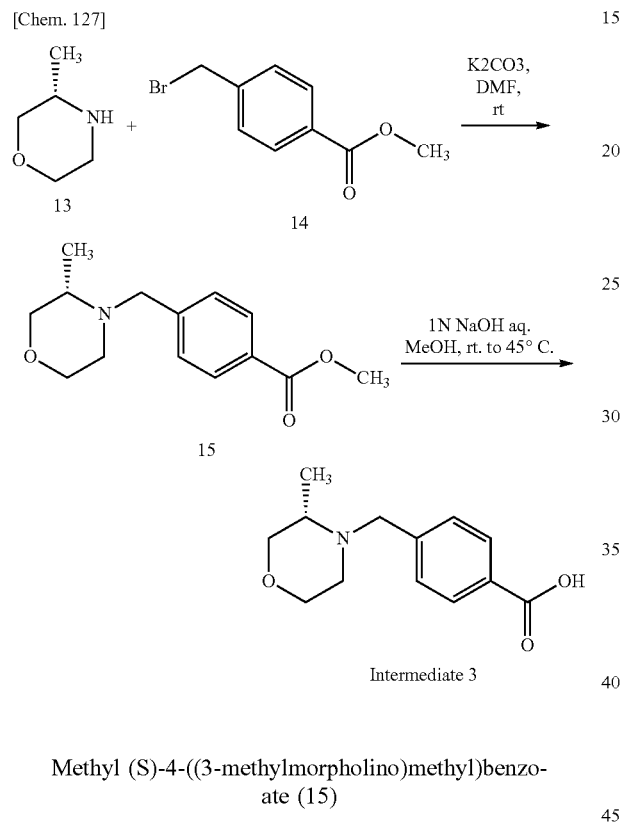

Intermediate 3

Methyl (S)-4-((3-methylmorpholino)methyl)benzoate (15)

To a round-bottom flask equipped with a magnetic stir bar were added (S)-3-metylmorpholine (CAS Number: 350595-57-2) (220 mg, 2.17 mmol), methyl 4-(bromomethyl)benzoate (CAS Number: 2417-72-3) (500 mg, 2.18 mmol), potassium carbonate (600 mg, 4.34 mmol) and DMF (5 mL). This mixture was allowed to stir at room temperature for 17.5 hours. The reaction mixture was diluted with water and extracted with EtOAc. The combined organic extracts were concentrated under a stream of air. The crude residue was purified by silica gel column chromatography (10-100% EtOAc in hexanes gradient) to afford the title compound (506 mg). LCMS: $R_T$=0.45 min; m/z $(M+1)^+$=250.

(S)-4-((3-Methylmorpholino)methyl)benzoic acid (Intermediate 3)

To a solution of methyl (S)-4-((3-methylmorpholino)methyl)benzoate (15) (506 mg, 2.02 mmol) in methanol (2 mL) was added 1 mol/L NaOH solution in water (2.0 mL). This mixture was allowed to stir at 45° C. overnight. The reaction mixture was neutralized with 1 mol/L HCl solution in water (2.0 mL) and then concentrated in vacuo to afford the title compound (329 mg). LCMS: $R_T$=0.16 min; m/z $(M+1)^+$=236.

The overall synthesis scheme for the preparation of N-(2,4-dichlorobenzyl)-4-formylbenzamide (Intermediate 4) is shown below.

[Chem. 128]

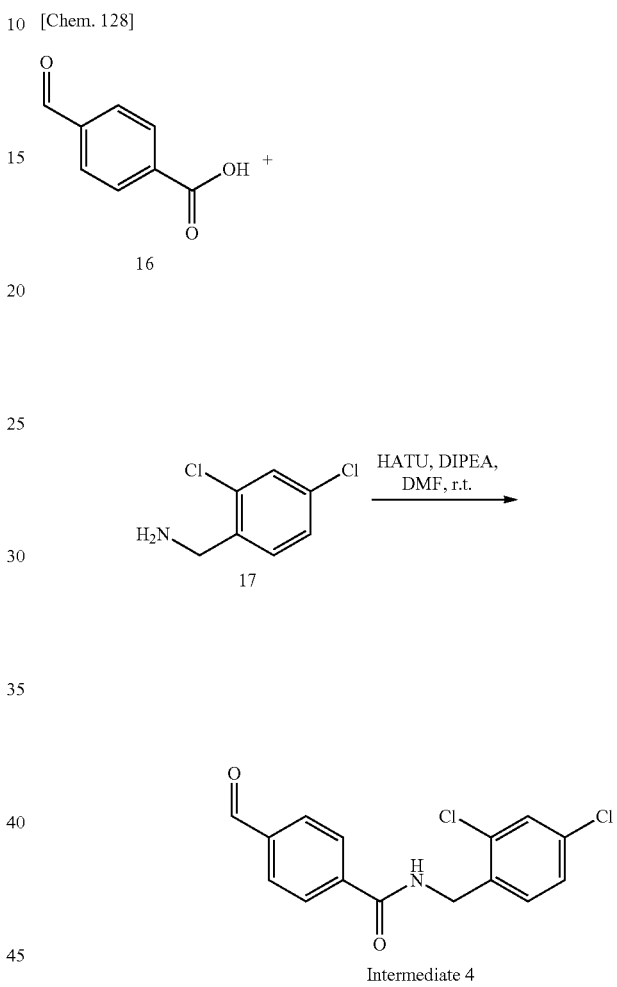

Intermediate 4

N-(2,4-Dichlorobenzyl)-4-formylbenzamide (Intermediate 4)

To a solution of 4-carboxybenzaldehyde (CAS Number: 619-66-9) (1.00 g, 6.66 mmol) in DMF (5 mL) were added HATU (CAS Number: 148893-10-1) (2.53 g, 6.66 mmol), N,N-diisopropylethylamine (2.3 mL, 13 mmol) at 0° C., followed by a solution of 2,4-dichlorobenzylamine (CAS Number: 95-00-1) in DMF (5 mL). This mixture was allowed to stir at room temperature overnight. The reaction mixture was diluted with water and extracted with EtOAc. The combined organic layer was washed with water, saturated NaCl solution in water, dried over anhydrous MgSO₄ and concentrated in vacuo. The residue was purified by silica gel column chromatography (20-100% EtOAc in hexanes gradient) to afford the title compound (1.82 g). LCMS: $R_T$=1.02 min; m/z $(M+1)^+$=308.

Example 7

N-(2,4-Dichlorobenzyl)-4-(4-morpholinomethyl)benzamide

[Chemical 129]

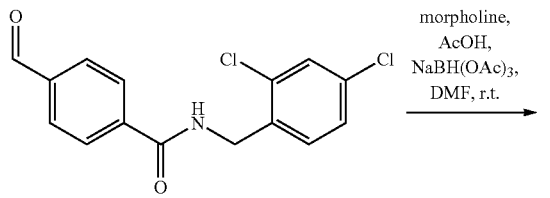

Intermediate 4

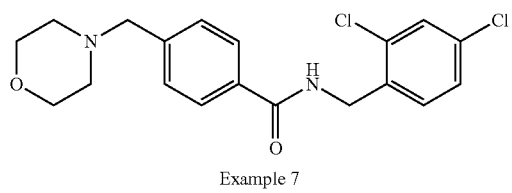

Example 7

To a screw-capped vial equipped with a magnetic stir bar were added N-(2,4-dichlorobenzyl)-4-formylbenzamide (Intermediate 4) (40 mg, 0.13 mmol), morpholine (12 mg, 0.14 mmol), AcOH (7 μL, 0.1 mmol) and DMF (1 mL). This mixture was allowed to stir at room temperature for 20 minutes, followed by sodium triacetoxyborohydride (27 mg, 0.13 mmol). This mixture was allowed to stir at room temperature overnight. The reaction mixture was diluted with saturated aqueous sodium bicarbonate solution in water and extracted with EtOAc. The combined organic extracts were concentrated under a stream of air. The crude residue was purified by silica gel column chromatography (20-100% EtOAc in hexanes gradient) to afford the present invention compound (13 mg). LCMS: $R_T$=0.81 min; m/z (M+1)$^+$=379. $^1$H NMR (400 MHz, d$_6$-DMSO) δ 2.32-2.47, 3.50-3.63, 4.51, 7.35-7.45, 7.63, 7.88, 9.04.

Example 7-1 to 7-9

The following compounds in Table 5 were prepared in an analogous manner with the appropriate starting materials.

TABLE 5

| Example No. | Compound name | Retention Time (min) | MS [M+1]+ |
|---|---|---|---|
| 7-1 | N-(2,4-dichlorobenzyl)-4-[(4,4-difluoro-1-piperidinyl)methyl]benzamide | 0.88 | 413 |
| 7-2 | N-(2,4-dichlorobenzyl)-4-[(4-fluoro-1-piperidinyl)methyl]benzamide | 1.28*3 | 395 |
| 7-3 | N-(2,4-dichlorobenzyl)-4-[(3,3-difluoro-1-pyrrolidinyl)methyl]benzamide ($^1$H NMR (400 MHz, d$_6$-DMSO) δ 2.20-2.34, 2.69-2.72, 2.83-2.90, 3.69, 4.51, 7.35-7.44, 7.63, 7.89, 9.05.) | 1.31*3 | 399 |
| 7-4 | N-(2,4-dichlorobenzyl)-4-[(1,1-dioxido-4-thiomorpholinyl)methyl]benzamide | 1.0*3 | 427 |
| 7-5 | 4-[(3,3-difluoro-1-pyrrolidinyl)methyl]-N-[3-fluoro-4-(trifluoromethoxy)benzyl]benzamide ($^1$H NMR (400 MHz, d$_6$-DMSO) δ 2.26-2.52, 2.72-2.79, 2.89-2.96, 3.74, 4.56, 7.33, 7.46-7.51, 7.60, 7.93, 9.16.) | 0.81 | 433 |

TABLE 5-continued

| Example No. | Compound name | Retention Time (min) | MS [M+1]+ |
|---|---|---|---|
| 7-6 | N-[3-fluoro-4-(trifluoromethoxy)benzyl]-4-{[(3S)-3-methyl-4-morpholinyl]methyl}benzamide | 0.80 | 427 |
| 7-7 | 4-[(3,3-difluoro-1-pyrrolidinyl)methyl]-N-[2-methoxy-4-(trifluoromethoxy)benzyl]benzamide($^1$H NMR (400 MHz, d$_6$-DMSO) δ 2.20-2.34, 2.67-2.73, 2.83-2.90, 3.68, 3.87, 4.43, 6.91, 7.00, 7.26, 7.41,7.88, 8.89.) | 0.83 | 445 |
| 7-8 | N-[2-methoxy-4-(trifluoromethoxy)benzyl]-4-{[(3R)-3-methyl-4-morpholinyl]methyl}benzamide | 0.81 | 439 |
| 7-9 | N-{2-methoxy-4-(trifluoromethoxy)benzyl]-4-{[(3S)-3-methyl-4-morpholinyl]methyl}benzamide | 0.80 | 439 |

*3the data were measured by Basic (high pH) LCMS method (2) as described above.

The overall synthesis scheme for the preparation of 3-fluoro-4-(methylsulfonamido)benzoic acid (Intermediate 5) is shown below.

[Chem. 130]

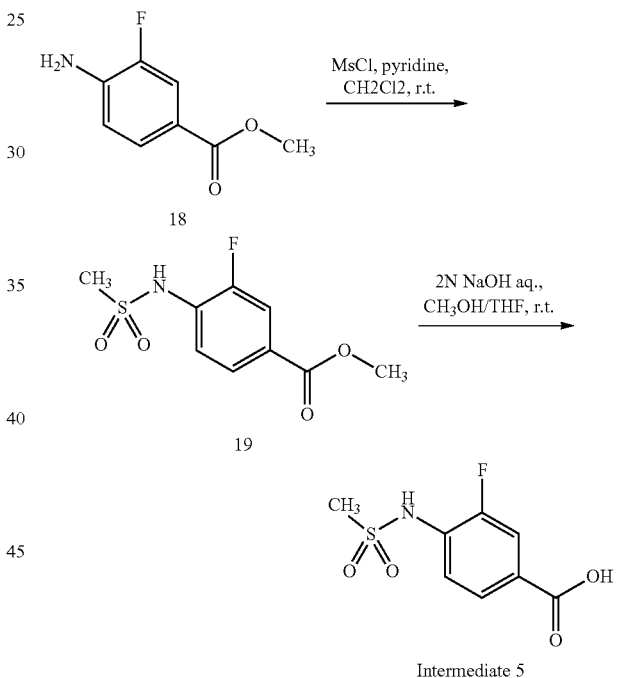

Methyl 3-fluoro-4-(methylsulfonamido)benzoate (19)

To a solution of methyl 4-amino-3-fluorobenzoate (CAS Number: 185629-32-7) (169 mg, 1.00 mmol) in dichloromethane (2 mL) were added pyridine (0.322 mL, 4.00 mmol) and methanesulfonyl chloride (85 μL, 1.1 mmol) at room temperature. This mixture was allowed to stir at room temperature for 5 hours. The reaction mixture was diluted with 1 mol/L HCl and extracted with dichloromethane twice. The combined organic extracts were concentrated under a stream of air. The residue was triturated with Et$_2$O and the liquid was removed by decantation to afford the title compound (crude 341 mg). LCMS: $R_T$=0.72 min; m/z (M+1)$^+$=248.

3-Fluoro-4-(methylsulfonamido)benzoic acid (Intermediate 5)

To a solution of methyl 3-fluoro-4-(methylsulfonamido)benzoate (19) (crude 341 mg) in methanol and tetrahydrofuran (1 mL/1 mL) was added 2 mol/L NaOH solution in water (3.0 mL). This mixture was allowed to stir at room temperature for 7.5 hours. The reaction mixture was neutralized with 2 mol/L HCl solution in water (3.0 mL) at 0° C. The precipitate was collected by filtration to produce the title compound (163 mg). TLC: $R_f$=0.04 (hexane/ethyl acetate=1/1).

The overall synthesis scheme for the preparation of (Intermediate 6) is shown below.

[Chem. 131]

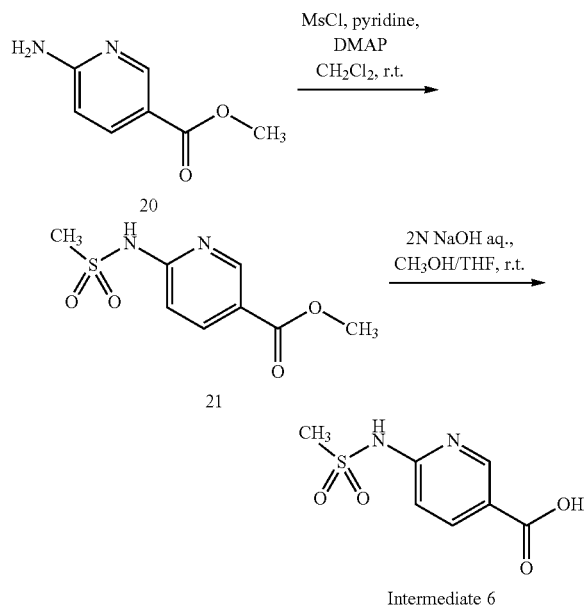

Methyl 6-(methylsulfonamido)nicotinate (21)

To a solution of methyl 6-aminonicotinate (CAS Number: 36052-24-1) (152 mg, 1.00 mmol) in dichloromethane (2 mL) were added pyridine (0.322 mL, 4.00 mmol) and methanesulfonyl chloride (85 μL, 1.1 mmol) at room temperature. This mixture was allowed to stir at room temperature for 2.5 hours and then heated to 50° C. for 3 hours. After cooling to ambient temperature, 4-dimethylaminopyridine (24 mg, 0.20 mmol) was added to the reaction mixture, and the resulting mixture was allowed to stir at room temperature for 7.5 hours. Methanesulfonyl chloride (85 μL, 1.1 mmol) was added to the reaction mixture, and the resulting mixture was allowed to stir at room temperature overnight. The reaction mixture was diluted with saturated aqueous sodium bicarbonate solution in water and dichlromethane. The insoluble solid was collected by filtration to produce the title compound (144 mg). LCMS: $R_T$=0.55 min; m/z $(M+1)^+$ =231.

6-(Methylsulfonamido)nicotinic acid (Intermediate 6)

To a suspension of methyl 6-(methylfulfonamido)nicotinate (21) (144 mg, 0.625 mmol) in methanol and tetrahydrofuran (1.2 mL/1.2 mL) was added 2 mol/L NaOH solution in water (1.2 mL). This mixture was allowed to stir at room temperature for 1 hours and then at 40° C. for 3 hours. The reaction mixture was neutralized with 2 mol/L HCl solution in water (1.3 mL) at 0° C. The precipitate was collected by filtration to afford the title compound (98 mg). TLC: $R_f$=0.12 (dichloromethane/methanol=5/1).

Example 8-1 to 8-6

The compounds shown in Table 6 were prepared in an analogous manner with the appropriate starting materials, such as intermediate 5, 6 or a compound prepared in same procedure as in the scheme for intermediate 5 or 6.

TABLE 6

| Example No. | Compound name | Retention Time (min) | MS [M + 1]+ |
|---|---|---|---|
| 8-1 | N-(2,4-dichlorobenzyl)-6-[(methylsulfonyl)amino]nicotinamide | 0.91 | 374 |
| 8-2 | N-[2-methoxy-4-(trifluoromethoxy)benzyl]-6-[(methylsulfonyl)amino]nicotinamide | 0.92 | 420 |
| 8-3 | N-[2-chloro-4-(trifluoromethyl)benzyl]-6-[(methylsulfonyl)amino]nicotinamide ($^1$H NMR (400 MHz, d$_6$-DMSO) δ 3.30-3.40, 4.60, 7.01-7.12, 7.60, 7.72, 7.89, 8.20, 8.72-8.87, 9.20, 10.89-11.25.) | 0.93 | 408 |
| 8-4 | 3-methoxy-4-[(methylsulfonyl)amino]-N-[2-methyl-4-(trifluoromethoxy)benzyl]benzamide ($^1$H NMR (400 MHz, d$_6$-DMSO) δ 2.38, 3.03, 3.89, 4.47, 7.14-7.23, 7.32-7.40, 7.52, 7.57, 8.94, 9.11.) | 0.97 | 433 |
| 8-5 | 3-fluoro-4-[(methylsulfonyl)amino]-N-[2-methyl-4-(trifluoromethoxy)benzyl]benzamide ($^1$H NMR (400 MHz, d$_6$-DMSO) δ 2.37, 3.11, 4.46, 7.16, 7.20-7.23, 7.34, 7.52, 7.74-7.82, 9.01, 9.94.) | 0.97 | 421 |
| 8-6 | 3-fluoro-N-[3-fluoro-4-(trifluoromethoxy)benzyl]-4-[(methylsulfonyl)amino]benzamide ($^1$H NMR (400 MHz, d$_6$-DMSO) δ 3.11, 4.50, 7.27, 7.44, 7.49-7.57, 7.72-7.82, 9.17, 9.96.) | 0.93 | 425 |

The overall synthesis scheme for the preparation of 1-[2-chloro-4-(trifluoromethoxy)phenyl]methanamine (Intermediate 7) is shown below.

[Chem. 132]

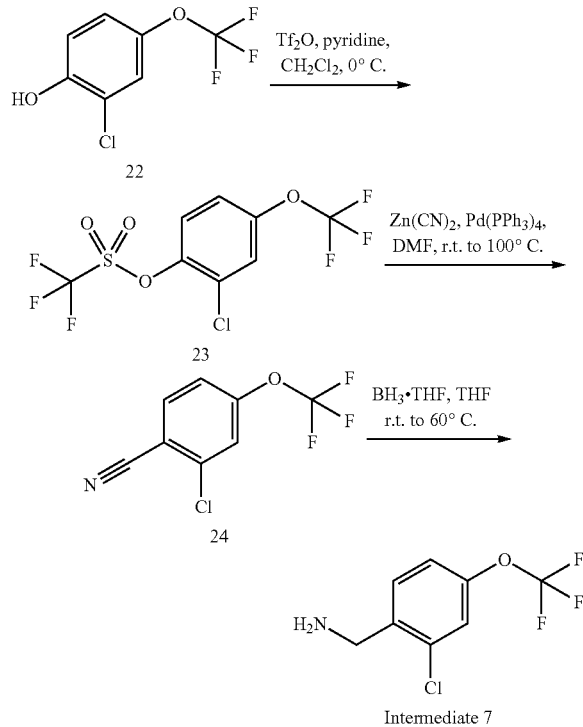

2-Chloro-4-(trifluoromethoxy)phenyl trifluoromethanesulfonate (23)

To a solution of 2-chloro-4-trifluoromethoxyphenol (CAS Number: 70783-75-4) (1.00 g, 4.70 mmol) and pyridine (1.14 mL, 14.1 mmol) in dichloromethane (10 mL) was added trifluoromethanesulfonic anhydride (0.950 mL, 5.65 mmol) at 0° C. This mixture was allowed to stir at 0° C. for 80 minutes. The reaction mixture was poured into 1 mol/L HCl solution in water and extracted with EtOAc twice. The combined organic extracts were washed with water, saturated aqueous sodium bicarbonate solution and NaCl solution in water and then dried over magnesium sulfate. The filtrate was concentrated under reduced pressure. To the residue was added tert-butyl methyl ether and the resulting solution was concentrated under reduced pressure to afford the title compound (1.61 g). TLC: $R_f$=0.74 (hexane/ethyl acetate=10/1).

2-Chloro-4-(trifluoromethoxy)benzonitrile (24)

To a solution of 2-chloro-4-(trifluoromethoxy)phenyl trifluoromethanesulfonate (23) (1.61 g, 4.66 mmol) in DMF (16 mL) were added $Zn(CN)_2$ (656 mg, 5.59 mmol) and $Pd(PPh_3)_4$ (538 mg, 0.47 mmol) at room temperature. This mixture was allowed to stir at 100° C. for 21 hours. The reaction mixture was poured into cold 0.2 mol/L NaOH solution in water and cold 5 mol/L NaOH solution in water was added to the mixture. The reaction mixture was extracted with tert-butyl methyl ether twice. Hexane was added to the combined organic extracts. The extracts were washed with water twice and NaCl solution in water and then dried over magnesium sulfate. The filtrate was concentrated under reduced pressure. The residue was purified by silica gel column chromatography (hexane/EtOAc). To the residue was added THF and the resulting solution was concentrated under reduced pressure to afford the title compound (crude 1.05 g, content c.a. 378 mg judged by $^1$H NMR). TLC: $R_f$=0.11 (hexane).

1-[2-Chloro-4-(trifluoromethoxy)phenyl]methanamine (Intermediate 7)

To a solution of 2-chloro-4-(trifluoromethoxy)benzonitrile (24) (crude 500 mg, content c.a. 180 mg, 0.81 mmol) in THF (5 mL) was added 1.0 mol/L borane tetrahydrofuran complex in THF (1.7 mL, 1.7 mmol) at room temperature. This mixture was allowed to stir at 60° C. for 14.5 hours. The reaction mixture was concentrated under reduced pressure up to c.a. 2 mL. After the reaction mixture was diluted with 1 mol/L HCl solution in water at 0° C., dichloromethane was added to the mixture. The mixture was extracted with 1 mol/L HCl solution in water twice. The combined aqueous extracts were washed with dichloromethane and then treated with 5 mol/L NaOH solution in water. The resulting basic aqueous solution was extracted with dichloromethane three times. The combined aqueous extracts were washed with water and NaCl solution in water and then dried over magnesium sulfate. The filtrate was concentrated under reduced pressure. To the residue was added tert-butyl methyl ether and the resulting solution was concentrated under reduced pressure to afford the title compound (crude 185 mg, content c.a. 97 mg judged by $^1$H NMR). TLC: $R_f$=0.50 (dichloromethane/methanol=5/1).

Example 9

N-[[2-Chloro-4-(trifluoromethoxy)phenyl]methyl]-[1,2,4]triazolo[4,3-a]pyridine-7-carboxamide

[Chem. 133]

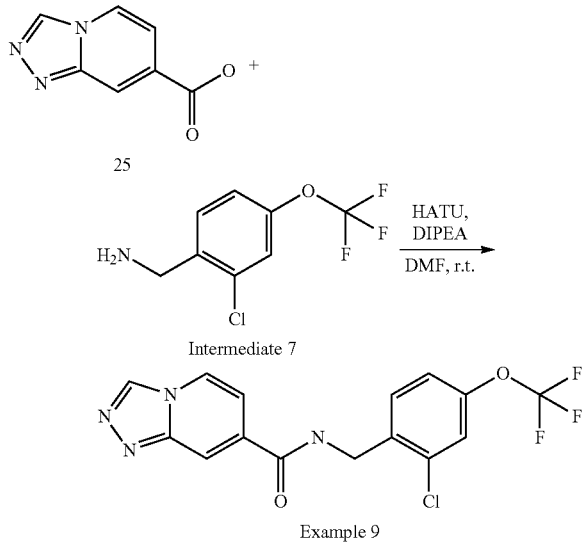

Example 9

To a solution of 1-[2-chloro-4-(trifluoromethoxy)phenyl]methanamine (Intermediate 7) (crude 57 mg, content c.a. 30 mg, 0.13 mmol) in DMF (0.4 mL) were added [1,2,4]Triazolo[4,3-a]pyridine-7-carboxylic acid (CAS Number: 1234616-66-0) (22 mg, 0.13 mmol), N,N-diisopropylethylamine (69 μL, 0.40 mmol) and then HATU (CAS Number: 148893-10-1) (76 mg, 0.20 mmol) at room temperature. This mixture was allowed to stir at room temperature for 5 hours. The reaction mixture was poured into cold 1 mol/L HCl solution in water and extracted with EtOAc twice. The combined organic extracts were washed with water, saturated aqueous sodium bicarbonate solution and NaCl solution in water and then dried over magnesium sulfate. The filtrate was concentrated under reduced pressure. The residue was triturated with (ethyl acetate/tert-butyl methyl ether=1/4) to afford the present invention compound (34 mg). LCMS: $R_T$=0.80 min[*1]; m/z (M+1)$^+$=371. $^1$H NMR (400 MHz, $d_6$-DMSO) δ 9.40 (t, J=6.0 Hz, 1H), 9.37 (d, J=1.0 Hz, 1H), 8.64 (dd, J=7.0, 1.0 Hz, 1H), 8.37 (s, 1H), 7.55-7.62 (m, 2H), 7.35-7.42 (m, 2H), 4.57 (d, J=6.0 Hz, 2H).

[*1]: the data were measured by Acidic standard LCMS method (1-2) as described above.

Example 9-1 to 9-20

The following compounds in Table 7 were prepared in same procedure as in Example 9 with the appropriate starting materials.

TABLE 7

| Example No. | Compound name | Retention Time (min) | MS [M + 1]+ |
|---|---|---|---|
| 9-1 | N-[[2-chloro-4-(trifluoromethoxy)phenyl]methyl]-4-(1,2,4-triazol-1-yl)benzamide; ($^1$H NMR (400 MHz, $d_6$-DMSO) δ 4.58, 7.40, 7.53, 7.61, 8.00-8.04, 8.08-8.13, 8.30, 9.22, 9.42.) | 0.94[*1] | 397 |
| 9-2 | N-[[2-chloro-4-(trifluoromethoxy)phenyl]methyl]-[1,2,4]triazolo[1,5-a]pyridine-6-carboxamide; ($^1$H NMR (400 MHz, $d_6$-DMSO) δ 4.59, 7.37-7.41, 7.58-7.63, 7.94, 8.09, 8.64, 9.33, 9.52.) | 0.88[*1] | 371 |
| 9-3 | N-[[2-chloro-4-(trifluoromethoxy)phenyl]methyl]-4-(1H-1,2,4-triazol-5-yl)benzamide | 0.87[*1] | 397 |
| 9-4 | N-[[2-chloro-4-(trifluoromethoxy)phenyl]methyl]-1-methylbenzotriazole-5-carboxamide; ($^1$H NMR (400 MHz, $d_6$-DMSO) δ 4.36, 4.60, 7.41, 7.56, 7.61, 7.96, 8.10, 8.65, 9.29.) | 0.97[*1] | 385 |
| 9-5 | N-[[2-chloro-4-(trifluoromethoxy)phenyl]methyl]-6-fluoropyridine-3-carboxamide; ($^1$H NMR (400 MHz, $d_6$-DMSO) δ 4.57, 7.32-7.41, 7.55, 7.61, 8.45, 8.77, 9.29.) | 1.00[*1] | 349 |
| 9-6 | N-[[2-chloro-4-(trifluoromethoxy)phenyl]methyl]-6-(1,2,4-triazol-1-yl)pyridine-3-carboxamide; ($^1$H NMR (400 MHz, $d_6$-DMSO) δ 4.60, 7.40, 7.58, 7.62, 8.01, 8.38, 8.53, 9.03, 9.39, 9.48.) | 0.97*1 | 398 |
| 9-7 | N-[[2-chloro-4-(trifluoromethoxy)phenyl]methyl]-1H-benzotriazole-5-carboxamide | 0.91[*1] | 371 |
| 9-8 | N-[[2-chloro-4-(trifluoromethoxy)phenyl]methyl]pyrazolo[1,5-a]pyrimidine-6-carboxamide | 0.87[*1] | 371 |
| 9-9 | N-[2-chloro-4-(trifluoromethoxy)benzyl]-1-cyclopropyl-1H-benzotriazole-5-carboxamide; ($^1$H NMR (400 MHz, $d_6$-DMSO) δ 1.27-1.31, 4.03-4.08, 4.59, 7.39, 7.54, 7.60, 7.95, 8.11, 8.64, 9.30.) | 0.89 | 411 |
| 9-10 | 2-bromo-N-[2-chloro-4-(trifluoromethoxy)benzyl][1,2,4]triazolo[1,5-a]pyridine-7-carboxamide; ($^1$H NMR (400 MHz, $d_6$-DMSO) δ 4.60, 7.40, 7.58, 7.62, 7.67, 8.36, 9.08, 9.52.) | 0.85 | 449 |
| 9-11 | N-[2-chloro-4-(trifluoromethoxy)benzyl]-3-methyl[1,2,4]triazolo[4,3-a]pyridine-7-carboxamide; ($^1$H NMR (400 MHz, $d_6$-DMSO) δ 2.71, 4.57, 7.33-7.35, 7.37-7.40, 7.54-7.56, 7.59-7.60, 8.29-8.30, 8.43-8.45, 9.37.) | 0.73 | 385 |
| 9-12 | N-[2-chloro-4-(trifluoromethoxy)benzyl][1,2,4]triazolo[1,5-a]pyridine-7-carboxamide; ($^1$H NMR (400 MHz, $d_6$-DMSO) δ 4.60, 7.40, 7.57-7.63, 8.42, 8.67, 9.09, 9.47.) | 0.82 | 371 |
| 9-13 | N-[2-chloro-4-(trifluoromethoxy)benzyl]-2-methyl[1,2,4]triazolo[1,5-a]pyridine-6-carboxamide; ($^1$H NMR (400 MHz, $d_6$-DMSO) δ 2.49, 4.59, 7.37-7.41, 7.59, 7.61, 7.79, 8.06, 9.31, 9.39.) | 0.89 | 385 |
| 9-14 | 7-amino-N-[2-chloro-4-(trifluoromethoxy)benzyl]pyrazolo[1,5-a]pyrimidine-6-carboxamide; ($^1$H NMR (400 MHz, $d_6$-DMSO) δ 4.56, 7.39, 7.55, 7.60, 8.20, 8.79, 8.50-9.10, 9.10.) | 0.81 | 386 |

TABLE 7-continued

| Example No. | Compound name | Retention Time (min) | MS [M + 1]+ |
|---|---|---|---|
| 9-15 | N-[2-chloro-4-(trifluoromethoxy)benzyl]-4-(1H-imidazol-2-yl)benzamide; ($^1$H NMR (400 MHz, d$_6$-DMSO) δ 4.54, 7.22, 7.37-7.39, 7.49-7.51, 7.58-7.59, 7.97-7.99, 8.02-8.04, 9.11.) | 0.78 | 396.3 |
| 9-16 | N-[2-chloro-4-(trifluoromethoxy)benzyl]tetrazolo[1,5-a]pyridine-6-carboxamide; ($^1$H NMR (400 MHz, d$_6$-DMSO) δ 4.62, 7.39-7.42, 7.60-7.63, 7.81, 8.74, 9.43, 9.60) | 0.93 | 372 |
| 9-17 | N-[2-chloro-4-(trifluoromethoxy)benzyl]tetrazolo[1,5-a]pyridine-7-carboxamide; ($^1$H NMR (400 MHz, d$_6$-DMSO) δ 4.55, 7.31-7.35, 7.55-7.58, 8.17, 8.24, 9.43, 9.77.) | 0.94 | 372 |
| 9-18 | 7-amino-N-[2-chloro-4-(trifluoromethoxy)benzyl]-2-methylpyrazolo[1,5-a]pyrimidine-6-carboxamide; ($^1$H NMR (400 MHz, d$_6$-DMSO) δ 2.42, 4.54, 6.33, 7.37-7.41, 7.54, 7.59, 8.72, 9.05.) | 0.78 | 400 |
| 9-19 | N-[2-chloro-4-(trifluoromethoxy)benzyl]-2-methylpyrazolo[1,5-a]pyrimidine-6-carboxamide; ($^1$H NMR (400 MHz, d$_6$-DMSO) δ 2.47, 4.59, 6.64, 7.37-7.41, 7.60-7.63, 8.89, 9.29, 9.48.) | 0.95 | 385 |
| 9-20 | 3-bromo-N-[2-chloro-4-(trifluoromethoxy)benzyl]pyrazolo[1,5-a]pyrimidine-6-carboxamide; ($^1$H NMR (400 MHz, d$_6$-DMSO) δ 4.77, 6.67, 7.15-7.19, 7.31-7.33, 7.56, 8.24, 8.84, 9.16.) | 0.97 | 449 |

*[1] the data were measured by Acidic standard LCMS method (1-2) as described above.

Example 10. Biological Activity (TREK Activity)

TREK activity of the present invention compounds are shown in Table 8.

TABLE 8

(thallium flux assay data)

| Example No. | TREK1 activation $R_{BL-1249}$ (%) | concentration of Example compound (μM) |
|---|---|---|
| 1 | 88 | 10 |
| 1-3 | 28 | 10 |
| 1-5 | 44 | 10 |
| 1-6 | 26 | 10 |
| 1-12 | 63 | 30 |
| 1-13 | 65 | 10 |
| 1-21 | 73 | 30 |
| 1-23 | 63 | 10 |
| 1-25 | 82 | 10 |
| 1-26 | 74 | 30 |
| 1-27 | 91 | 10 |
| 1-28 | 99 | 10 |
| 1-29 | 80 | 10 |
| 1-30 | 76 | 30 |
| 1-31 | 90 | 10 |
| 1-33 | 26 | 10 |
| 1-34 | 33 | 10 |
| 1-36 | 26 | 10 |
| 1-42 | 41 | 30 |
| 1-44 | 25 | 30 |
| 1-45 | 85 | 10 |
| 1-46 | 67 | 10 |
| 1-47 | 63 | 10 |
| 1-50 | 66 | 10 |
| 1-51 | 65 | 10 |
| 1-52 | 75 | 10 |
| 1-55 | 38 | 30 |
| 1-61 | 48 | 30 |
| 1-71 | 19 | 10 |
| 1-72 | 60 | 30 |
| 1-76 | 101 | 10 |
| 1-81 | 78 | 10 |
| 1-86 | 75 | 10 |
| 1-87 | 72 | 10 |
| 1-89 | 70 | 10 |
| 1-92 | 70 | 10 |
| 2 | 20 | 30 |
| 2-1 | 54 | 10 |
| 2-2 | 41 | 10 |
| 2-3 | 72 | 10 |
| 2-6 | 32 | 10 |
| 2-9 | 25 | 10 |
| 2-10 | 46 | 10 |
| 2-12 | 29 | 10 |
| 2-16 | 46 | 10 |
| 2-18 | 39 | 10 |
| 2-22 | 66 | 10 |
| 2-24 | 69 | 10 |
| 2-25 | 48 | 10 |
| 2-26 | 76 | 10 |
| 2-28 | 22 | 10 |
| 2-29 | 51 | 10 |
| 2-30 | 42 | 10 |
| 2-32 | 38 | 30 |
| 2-34 | 80 | 10 |
| 2-36 | 73 | 10 |
| 2-37 | 24 | 30 |
| 2-38 | 55 | 10 |
| 2-41 | 63 | 10 |
| 2-47 | 44 | 10 |
| 2-49 | 84 | 10 |
| 3-2 | 41 | 30 |
| 3-3 | 67 | 10 |
| 3-4 | 89 | 10 |
| 3-5 | 89 | 10 |
| 3-10 | 34 | 30 |
| 4 | 77 | 30 |
| 5 | 79 | 30 |
| 6 | 19 | 30 |
| 7 | 38 | 30 |
| 8-2 | 48 | 30 |
| 9 | 99 | 10 |
| 9-2 | 106 | 10 |
| 9-4 | 87 | 10 |

TABLE 8-continued (thallium flux assay data)

| Example No. | TREK1 activation $R_{BL-1249}$ (%) | concentration of Example compound (μM) |
|---|---|---|
| 9-7 | 125 | 10 |
| 9-8 | 106 | 10 |
| 9-11 | 126 | 10 |
| 9-14 | 79 | 10 |
| 9-15 | 59 | 10 |
| 9-16 | 95 | 10 |
| 9-17 | 78 | 10 |
| 9-19 | 68 | 10 |
| N-(2,4-dichlorobenzyl)-4-[(methylsulfonyl)amino]benzamide | 54 | 30 |
| 4-(1H-1,2,4-triazol-1-yl)-N-[4-(trifluoromethoxy)benzyl]benzamide | 63 | 10 |

The compounds of the present invention have TREK activation effects, so these compounds are useful for the disorders associated with TREK channel dysfunction.

Example 11. Biological Activity (Analgesic Effect in Acetic Acid Writhing Assay)

Analgesic effect of the present invention compounds are shown in the FIGURE. Example 1-25 at a dose of 3 mg/kg and Example 2 at a dose of 300 mg/kg significantly decreased the number of writhes. The inhibitory effects of Example 1-25 3 mg/kg and Example 2 300 mg/kg were the same degree as indomethacin 10 mg/kg. The present invention compounds have analgesic effect and are useful for pain.

Example 12. Formulation Example—1

The following components are mixed with each other in a usual method and punched out to obtain 10,000 tablets each containing 5 mg of the active ingredient.

N-[[2-chloro-4-(trifluoromethoxy)phenyl]methyl]-[1,2,4]triazolo[4,3-a]pyridine-7-carboxamide (50 g)

carboxymethylcellulose calcium (disintegrating agent) (20 g);
magnesium stearate (lubricant) (10 g);
microcrystalline cellulose (920 g).

Example 13. Formulation Example—2

The following components are mixed with each other in a usual method and punched out to obtain 10,000 tablets each containing 5 mg of the active ingredient.

N-[2-methyl-4-(trifluoromethoxy)benzyl]-6-(1H-1,2,4-triazol-1-yl)nicotinamide (50 g)

carboxymethylcellulose calcium (disintegrating agent) (20 g);
magnesium stearate (lubricant) (10 g);
microcrystalline cellulose (920 g).

The present compound has strong TREK activation, and thus is useful as a prophylactic and/or therapeutic agent for various disorders associated with TREK-1, TREK-2 or both TREK-1 and TREK-2 channel dysfunction, particulary pain, nasal inflammation, atrial fibrillation, acute respiratory distress syndrome, acute lung injury, overactive bladder, cerebral ischemia, epilepsy, amyotrophic lateral sclerosis, neuronal degenerative diseases (e.g. Alzheimer's disease), sepsis, pancreatic cancer, Cushing's syndrome, autosomal dominant polycystic kidney disease, bone fracture, osteoporosis, temporal lobe epilepsy, schizophrenia, colitis, or addiction.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

The invention claimed is:

1. A compound of formula (Id-1-1):

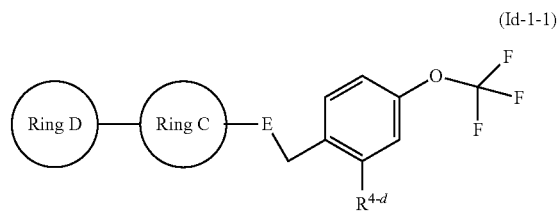

(Id-1-1)

wherein
E is —C(O)NR$^1$—;
R$^1$ is hydrogen, or C$_1$-C$_4$-alkyl;
R$^{4-d}$ is halo, SF$_5$, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio, or C$_1$-C$_4$-haloalkylthio;

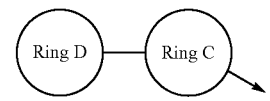

is

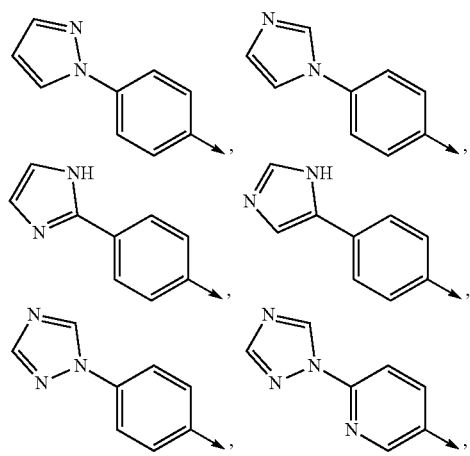

-continued

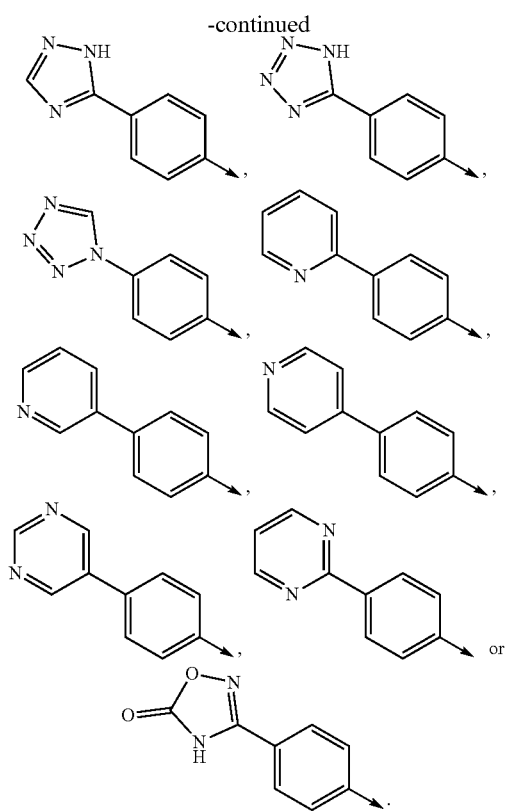

wherein arrow represents connecting position with E, each ring corresponding to ring C may be substituted independently with 1 to 3 $R^9$ groups which is selected from halogen, hydroxyl, $C_1$-$C_4$-alkyl, $C_1$-$C_4$-haloalkyl, $C_1$-$C_4$-alkoxy, or $C_1$-$C_4$-haloalkoxy, each ring corresponding to ring D may be substituted independently with 1 to 3 $R^{10}$ groups which is selected from halogen, hydroxyl, oxo, $C_1$-$C_4$-alkyl, $C_1$-$C_4$-haloalkyl, $C_1$-$C_4$-alkoxy, or $C_1$-$C_4$-haloalkoxy, or a pharmaceutically acceptable salt thereof.

2. The compound according to claim 1, wherein

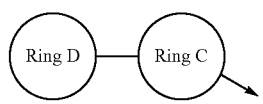

is

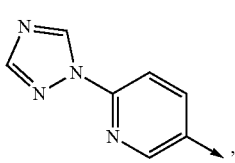

wherein arrow represents connecting position with E, each of ring corresponding to ring C may be optionally substituted with 1 to 3 $R^9$, each of ring corresponding to ring D may be optionally substituted with 1 to 3 $R^{10}$;

or a pharmaceutically acceptable salt thereof.

3. The compound according to claim 1, wherein the compound is (1) N-[2-methyl-4-(trifluoromethoxy)benzyl]-6-(1H-1,2,4-triazol-1-yl)nicotinamide, or (2)N-[2-methoxy-4-(trifluoromethoxy)benzyl]-4-(5-oxo-4,5-dihydro-1,2,4-oxadiazol-3-yl)benzamide, or a pharmaceutically acceptable salt thereof.

4. A pharmaceutical composition comprising a therapeutically effective amount of a compound according to claim 1, or a pharmaceutically acceptable salt thereof, and a pharmaceutically acceptable carrier.

* * * * *